(12) United States Patent
    Shelley

(10) Patent No.: US 10,746,739 B2
(45) Date of Patent: Aug. 18, 2020

(54) IDENTIFICATION OF NOVEL DIAGNOSTICS AND THERAPEUTICS BY MODULATING RHOH

(71) Applicant: Leukemia Therapeutics, LLC, Hull, MA (US)

(72) Inventor: Carl Simon Shelley, Hull, MA (US)

(73) Assignee: Leukemia Therapeutics, LLC, Hull, MA (US)

( * ) Notice: Subject to any disclaimer, the term of this patent is extended or adjusted under 35 U.S.C. 154(b) by 118 days.

(21) Appl. No.: 15/265,782

(22) Filed: Sep. 14, 2016

(65) Prior Publication Data

US 2017/0074883 A1  Mar. 16, 2017

Related U.S. Application Data

(60) Provisional application No. 62/218,512, filed on Sep. 14, 2015.

(51) Int. Cl.

| G01N 33/50 | (2006.01) |
|---|---|
| G01N 33/53 | (2006.01) |
| G01N 33/574 | (2006.01) |
| G01N 33/68 | (2006.01) |
| C12Q 1/6886 | (2018.01) |

(52) U.S. Cl.
    CPC ... *G01N 33/57426* (2013.01); *G01N 33/6893* (2013.01); *C12Q 1/6886* (2013.01); *G01N 2333/916* (2013.01); *G01N 2800/22* (2013.01)

(58) Field of Classification Search
    None
    See application file for complete search history.

(56) References Cited

U.S. PATENT DOCUMENTS

2008/0293661 A1   11/2008   Shelley et al.

FOREIGN PATENT DOCUMENTS

WO   WO 99/58669   11/1999

OTHER PUBLICATIONS

Cancer Genome Atlas Research Network et al., Integrated genomic and molecular characterization of cervical cancer. Nature. Mar. 16, 2017;543(7645):378-384. doi: 10.1038/nature21386. Epub Jan. 23, 2017.
Extended European Search Report for Application No. 16847251.2 dated Feb. 21, 2019.
Galiègue-Zouitina et al., Underexpression of RhoH in Hairy Cell Leukemia. Cancer Res. Jun. 15, 2008;68(12):4531-40. doi: 10.1158/0008-5472.CAN-07-5661.
Gundogdu et al., The haematopoietic GTPase RhoH modulates IL3 signalling through regulation of STAT activity and IL3 receptor expression. Mol Cancer. Aug. 25, 2010;9:225. doi: 10.1186/1476-4598-9-225.
Deckert et al., SAR650984, a novel humanized CD38-targeting antibody, demonstrates potent antitumor activity in models of multiple myeloma and other CD38+ hematologic malignancies. Clin Cancer Res. Sep. 1, 2014;20(17):4574-83.
Ishida et al., Defucosylated anti-CCR4 monoclonal antibody (KW-0761) for relapsed adult T-cell leukemia-lymphoma: a multicenter phase II study. J Clin Oncol. Mar. 10, 2012;30(8):837-42.
Kreitman et al., Phase I trial of anti-CD22 recombinant immunotoxin moxetumomab pasudotox (CAT-8015 or HA22) in patients with hairy cell leukemia. J Clin Oncol. May 20, 2012;30(15):1822-8.
Poret et al., CD38 in Hairy Cell Leukemia Is a Marker of Poor Prognosis and a New Target for Therapy. Cancer Res. Sep. 15, 2015;75(18):3902-11. doi: 10.1158/0008-5472.CAN-15-0893. Erratum in: Cancer Res. Dec. 1, 2015;75(23):5167.

*Primary Examiner* — Michail A Belyavskyi

(74) *Attorney, Agent, or Firm* — Wolf, Greenfield & Sacks, P.C.

(57) ABSTRACT

The disclosure relates to identifying novel therapeutic targets and/or diagnostic and/or prognostic markers by correcting abnormal RhoH expression in a hematopoietic cell.

2 Claims, 10 Drawing Sheets

Specification includes a Sequence Listing.

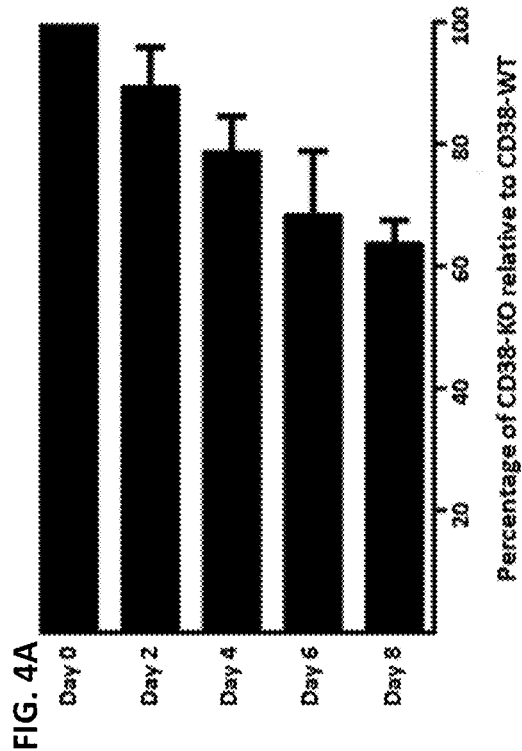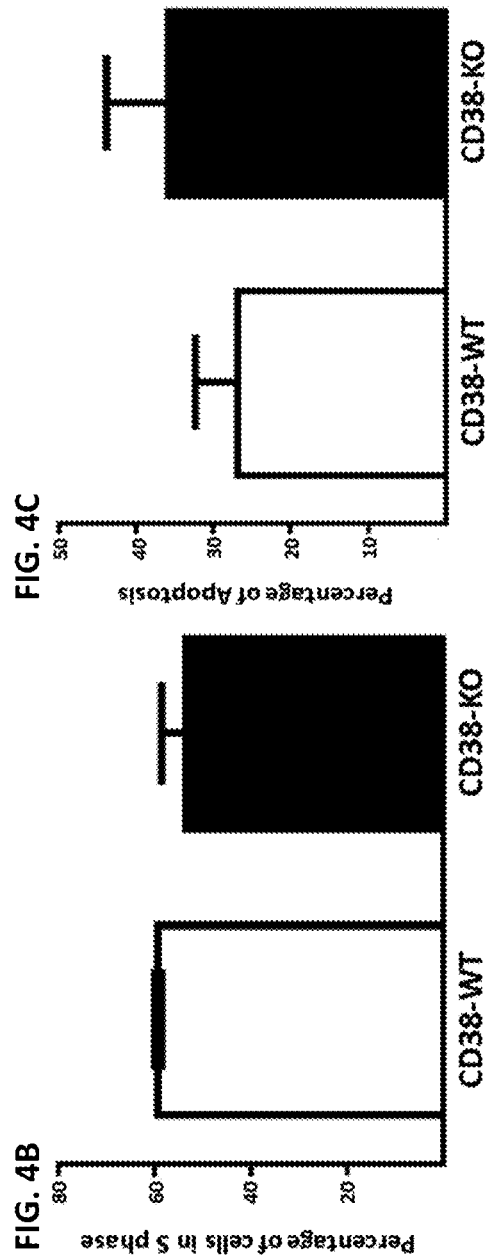

Fig. 8

SEQUENCE LISTING

<160> NUMBER OF SEQ ID NOS: 21

<210> SEQ ID NO 1
<211> LENGTH: 191
<212> TYPE: PRT
<213> ORGANISM: Artificial Sequence
<220> FEATURE:
<223> OTHER INFORMATION: Synthetic Polypeptide

<400> SEQUENCE: 1

Met Leu Ser Ser Ile Lys Cys Val Leu Val Gly Asp Ser Ala Val Gly
1               5                   10                  15

Lys Thr Ser Leu Leu Val Arg Phe Thr Ser Glu Thr Phe Pro Glu Ala

```
            20                  25                  30
Tyr Lys Pro Thr Val Tyr Glu Asn Thr Gly Val Asp Val Phe Met Asp
            35                  40                  45

Gly Ile Gln Ile Ser Leu Gly Leu Trp Asp Thr Ala Gly Asn Asp Ala
    50                  55                  60

Phe Arg Ser Ile Arg Pro Leu Ser Tyr Gln Gln Ala Asp Val Val Leu
65                  70                  75                  80

Met Cys Tyr Ser Val Ala Asn His Asn Ser Phe Leu Asn Leu Lys Asn
                85                  90                  95

Lys Trp Ile Gly Glu Ile Arg Ser Asn Leu Pro Cys Thr Pro Val Leu
            100                 105                 110

Val Val Ala Thr Gln Thr Asp Gln Arg Glu Met Gly Pro His Arg Ala
        115                 120                 125

Ser Cys Val Asn Ala Met Glu Gly Lys Lys Leu Ala Gln Asp Val Arg
    130                 135                 140

Ala Lys Gly Tyr Leu Glu Cys Ser Ala Leu Ser Asn Arg Gly Val Gln
145                 150                 155                 160

Gln Val Phe Glu Cys Ala Val Arg Thr Ala Val Asn Gln Ala Arg Arg
                165                 170                 175

Arg Asn Arg Arg Arg Leu Phe Ser Ile Asn Glu Cys Lys Ile Phe
            180                 185                 190

<210> SEQ ID NO 2
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 2
ctttcccgag accgtcct                                                   18

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
gatgcgtcaa gtacactgaa                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
caactctgtc ttggcgtcag                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
ggactcccta ctcagcacca                                                 20
```

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
caaaagagtg atggggtagg                                           20

<210> SEQ ID NO 7
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 7
tatttatagg caaggtgagg ac                                        22

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
ctggggaaac ctaagagatg                                           20

<210> SEQ ID NO 9
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 9
ggctcatgga agaaaactaa g                                         21

<210> SEQ ID NO 10
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 10
tctgctggga gtaggatgc                                            19

<210> SEQ ID NO 11
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 11
tgctaacaat gctgggtca                                            19

<210> SEQ ID NO 12
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 12
tatgtactgc ccaggtcaag    20

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13
tttttctttc tcacactgcc    20

<210> SEQ ID NO 14
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 14
cagtgagatg aggt    14

<210> SEQ ID NO 15
<211> LENGTH: 91
<212> TYPE: DNA
<213> ORGANISM: Artificial Sequence
<220> FEATURE:
<223> OTHER INFORMATION: Synthetic Polynucleotide

<400> SEQUENCE: 15
cagtggagcg gtccgggcac caccaagcgc tttcccgaga ccgtcctggc gcgatgcgtc    60
aagtacactg aaattcatcc tgagatgagg t    91

<210> SEQ ID NO 16
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 16
cagtggagcg gtccgggcac caccaagcgc ttttcatcct gagatgaggt    50

<210> SEQ ID NO 17
<211> LENGTH: 91
<212> TYPE: DNA
<213> ORGANISM: Artificial Sequence
<220> FEATURE:
<223> OTHER INFORMATION: Synthetic Polynucleotide

<400> SEQUENCE: 17
cagtggagcg gtccgggcac caccaagcgc tttcccgaga ccgtcctggc gcgatgcgtc    60
aagtacactg aaattcatcc tgagatgagg t    91

<210> SEQ ID NO 18
<211> LENGTH: 91
<212> TYPE: DNA
<213> ORGANISM: Artificial Sequence
<220> FEATURE:
<223> OTHER INFORMATION: Synthetic Polynucleotide

<400> SEQUENCE: 18

-continued

```
cagtggagcg tccgggcac caccaagcgc tttcccgaga ccgtcctggc gcgatgcgtc      60
aagtacactg aaattcatcc tgagatgagg t                                   91

<210> SEQ ID NO 19
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 19
aagcacattt ccc                                                       13

<210> SEQ ID NO 20
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 20
cagtggagcg gtccgggcac caccaagcgc tttcccgaga ccgtccgatg cgtcaagtac    60
actgaaattc atcctgagat gaggt                                          85

<210> SEQ ID NO 21
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 21
cagtggagcg g                                                         11
```

IDENTIFICATION OF NOVEL DIAGNOSTICS AND THERAPEUTICS BY MODULATING RHOH

RELATED APPLICATIONS

This application claims the benefit under 35 U.S.C. § 119(e) of U.S. Provisional Patent Application filed Sep. 14, 2015, entitled "IDENTIFICATION OF NOVEL DIAGNOSTICS AND THERAPEUTICS BY MODULATING RHOH", Ser. No. 62/218,512 the contents of which are incorporated by reference herein in their entirety.

FIELD

The disclosure relates to RhoH modulation for identifying therapeutic targets and diagnostic markers in hematopoietic disorders.

BACKGROUND

Aberrant expression of the intracellular signaling molecule Ras Homolog Family Member H (RhoH) occurs in a number of hematopoietic disorders, such as leukemias and lymphomas. In these disorders, abnormal expression of RhoH has been shown to be a marker of poor prognosis. However, directly using RhoH as a diagnostic marker or therapeutic target is difficult since it is expressed intracellularly.

SUMMARY

This disclosure is based, in part, on the discovery that correcting abnormal intracellular expression of RhoH in hematopoietic disorders (e.g., leukemia) ameliorates disease progression and identifies molecules in the cell (e.g., leukemia cell) that were dependent upon this abnormal expression. This discovery allows the identification of novel druggable targets that are dependent upon abnormal RhoH expression. These targets are also believed to represent potential new diagnostic and/or prognostic markers.

According to one aspect of the disclosure, a method of identifying a hematopoietic disorder-associated molecule in a hematopoietic cell is provided. The method comprises identifying a hematopoietic cell having abnormal RhoH level, restoring RhoH level in the cell to a control level, and measuring a level of a molecule in the cell before and after restoring the level of RhoH in the cell to the control level, wherein a decrease in the level of the molecule in the cell after restoring the RhoH level in the cell to the control level indicates that the molecule is a hematopoietic disorder-associated molecule.

In some embodiments, said molecule is on the surface of the hematopoietic cell. In some embodiments, said molecule is inside the hematopoietic cell. In some embodiments, said molecule is secreted by the hematopoietic cell. In some embodiments, said molecule is a polypeptide, protein, or RNA. In some embodiments, the RNA is messenger RNA (mRNA), microRNA (miRNA), or long non-coding RNAs (lncRNA).

In some embodiments, said hematopoietic disorder is a leukemia, a lymphoma, an immune deficiency disorder, an autoimmune disorder, an inflammatory disorder, polycythemia vera, multiple myeloma, aplastic anemia, thrombocytopenia, or ischemic reperfusion injury.

In some embodiments, said leukemia is Hairy-cell leukemia (HCL) acute lymphocytic leukemia (ALL), acute myelogenous leukemia (AML), chronic lymphocytic leukemia (CLL), chronic myelogenous leukemia (CML), adult T-cell leukemia/lymphoma (ATLL), T-cell or B-cell prolymphocytic leukemia (PLL), T-cell or B-cell large granular lymphocytic leukemia (LGLL), or aggressive natural killer cell leukemia.

In some embodiments, the leukemia is AML. In some embodiments, the hematopoietic disorder-associated molecule in AML is tescalcin (TESC), CD93, KCNN4, SLC4A2, or CDC42EP1.

In some embodiments, the leukemia is HCL. In some embodiments, the hematopoietic disorder-associated molecule in HCL is CD21, CD121b, CD150, CSF1R, GPR30, ITGB7, FCRL2, FCRL3 or CD22.

In some embodiments, the leukemia is ATLL. In some embodiments, the hematopoietic disorder-associated molecule in ATLL is CD54, CD82, CD83, CD123, CD252, or CD194.

According to another aspect of the disclosure, a method of treating a hematopoietic disorder in a subject is provided. The method comprises administering to a subject in need thereof subject an effective amount of an agent that targets a hematopoietic disorder-associated molecule identified above.

In some embodiments, said molecule is on the surface of the hematopoietic cell. In some embodiments, said molecule is inside the hematopoietic cell. In some embodiments, said molecule is secreted by the hematopoietic cell. In some embodiments, said molecule is a peptide, protein, or RNA. In some embodiments, the RNA is messenger RNA (mRNA), microRNA (miRNA), or long non-coding RNAs (lncRNA).

In some embodiments, said hematopoietic disorder is a leukemia, a lymphoma, an immune deficiency disorder, an autoimmune disorder, an inflammatory disorder, polycythemia vera, multiple myeloma, aplastic anemia, thrombocytopenia, ischemic reperfusion injury.

In some embodiments, said leukemia is Hairy-cell leukemia (HCL) acute lymphocytic leukemia (ALL), acute myelogenous leukemia (AML), chronic lymphocytic leukemia (CLL), chronic myelogenous leukemia (CML), adult T-cell leukemia/lymphoma (ATLL), T-cell or B-cell prolymphocytic leukemia (PLL), T-cell or B-cell large granular lymphocytic leukemia (LGLL), aggressive natural killer cell leukemia.

In some embodiments, the leukemia is AML. In some embodiments, the hematopoietic disorder-associated molecule in AML is tescalcin (TESC), CD93, KCNN4, SLC4A2, or CDC42EP1.

In some embodiments, the leukemia is HCL. In some embodiments, the hematopoietic disorder-associated molecule in HCL is CD21, CD121b, CD150, CSF1R, GPR30, ITGB7, FCRL2, FCRL3 or CD22.

In some embodiments, the leukemia is ATLL. In some embodiments, the hematopoietic disorder-associated molecule in ATLL is CD54, CD82, CD83, CD123, CD252, or CD194.

According to yet another aspect of the disclosure, a method of diagnosing a hematopoietic disorder in a subject is provided. The method comprises obtaining a cell from a subject having, suspected of having, or at increased risk of having, hematopoietic disorder, determining the presence one or more of the hematopoietic disorder-associated molecule identified above, thereby indicating that the subject has or is at risk of having hematopoietic disorder.

In some embodiments, said molecule is on the surface of the hematopoietic cell. In some embodiments, said molecule is inside the hematopoietic cell. In some embodiments, said molecule is secreted by the hematopoietic cell. In some embodiments, said molecule is a peptide, protein, or RNA. In some embodiments, the RNA is messenger RNA (mRNA), microRNA (miRNA), or long non-coding RNAs (lncRNA).

In some embodiments, said hematopoietic disorder is a leukemia, a lymphoma, an immune deficiency disorder, an autoimmune disorder, an inflammatory disorder, polycythemia vera, multiple myeloma, aplastic anemia, thrombocytopenia, ischemic reperfusion injury.

In some embodiments, said leukemia is Hairy-cell leukemia (HCL) acute lymphocytic leukemia (ALL), acute myelogenous leukemia (AML), chronic lymphocytic leukemia (CLL), chronic myelogenous leukemia (CML), adult T-cell leukemia/lymphoma (ATLL), T-cell or B-cell prolymphocytic leukemia (PLL), T-cell or B-cell large granular lymphocytic leukemia (LGLL), aggressive natural killer cell leukemia.

In some embodiments, the leukemia is AML. In some embodiments, the hematopoietic disorder-associated molecule in AML is tescalcin (TESC), CD93, KCNN4, SLC4A2, or CDC42EP1.

In some embodiments, the leukemia is HCL. In some embodiments, the hematopoietic disorder-associated molecule in HCL is CD21, CD121b, CD150, CSF1R, GPR30, ITGB7, FCRL2, FCRL3 or CD22.

In some embodiments, the leukemia is ATLL. In some embodiments, the hematopoietic disorder-associated molecule in ATLL is CD54, CD82, CD83, CD123, CD252, or CD194.

Each of the limitations of the disclosure can encompass various embodiments of the disclosure. It is, therefore, anticipated that each of the limitations of the disclosure involving any one element or combinations of elements can be included in each aspect of the disclosure. The disclosure is capable of other embodiments and of being practiced or of being carried out in various ways. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the disclosure, as well as various advantages and utilities will be apparent with reference to the Detailed Description of the Invention. Each aspect of the disclosure can encompass various embodiments as will be understood.

All documents identified in this application are incorporated in their entirety herein by reference.

BRIEF DESCRIPTION OF THE DRAWINGS

FIG. 1A is a quantitative RT-PCR analysis showing that when RhoH expression is induced in JOK-1 HCL cells (JOK-RhoH), CD38 mRNA levels are significantly reduced compared to JOK-1 HCL cells where RhoH expression is not induced (JOK-Empty) (Paired Student t-test: P=0.0026). Histograms represent the mean of four experiments performed in duplicate ±s.d. FIG. 1B is a Western blot analysis using an anti-CD38 mouse monoclonal antibody showing that when RhoH expression is induced in JOK-1 HCL cells (JOK-RhoH), CD38 protein levels in total protein lysates are lower than in JOK-1 where RhoH is not induced (JOK-Empty). An antibody against α-actin was used in the control analysis of lysates. FIG. 1C is a flow cytometric analysis showing that expression of CD38 on the surface of JOK-1 cells is lower when RhoH is induced (JOK-RhoH) compared to when RhoH is not induced (JOK-Empty). Analysis was performed using a FITC-conjugated antibody that specifically binds CD38 (CD38 Ab) or an isotype-matched control antibody (Isotype Ab). A representative example of the flow patterns acquired is depicted along with the mean percentages of FITC-positive cells calculated from 4 experiments ±s.d. After subtraction of the fluorescence intensity attributable to the control antibody, the mean fluorescence intensity attributable specifically to the CD38 antibody was 71.8±14.3 s.d. for JOK-Empty and significantly less at 19.7±9.0 s.d. for JOK-RhoH (Paired Student t-test: P=0.0006).

FIG. 2A is a Western blot analysis of total protein lysates showing that CD38 is expressed by the HCL cell lines JOK-1, HC-1, Hair-M and Eskol but not the HCL cell line EH/K. An antibody against GAPDH was used in the control analysis of lysates. FIG. 2B (Panels A-D) is an immunohistochemical analysis of CD38 expression in bone marrow biopsies taken from HCL and CLL patients. Eight HCL patients were examined in this way and two found to be CD38-positive. The analysis of one of these CD38-positive patients is depicted (Panel A). The analysis of one of the six HCL patients determined to be CD38-negative is depicted (Panel B). As a control for the analysis of HCL patients, bone marrow biopsies taken from two CLL patients were identically examined for CD38 expression. The diagnostic pathology record of one of these CLL patients indicated that the bone marrow was CD38-positive (Panel C). The pathology record of the second CLL patient indicated the bone marrow was CD38-negative (Panel D). All images were taken at a magnification of ×100.

FIG. 3A is a Kaplan-Meier plot showing the time between the end of first line therapy and the beginning of salvage therapy in 43 cases of HCL. This time interval was designated as the time to next treatment (TTNT). The 16 cases that were CD38-positive and the 27 cases that were CD38-negative are plotted separately with dotted and solid lines, respectively. The mean TTNT of the CD38-positive patients was significantly shorter than that of the patients who were CD38-negative (Gehan-Breslow-Wilcoxon test: P=0.0023). FIG. 3B is a Kaplan-Meier plot showing the TTNT only of the 23 patients within the total of 43 analyzed that suffered relapse. CD38-positive and CD38-negative cases are plotted separately with dotted and solid lines, respectively. The mean TTNT of 8 CD38-positive patients was significantly shorter than that of 15 patients who were CD38-negative (Gehan-Breslow-Wilcoxon test: P<0.0001). Within the CD38-positive group, four had first-line therapy with interferon and 4 had first-line therapy with purine analogs. Within the CD38-negative group, six were initially treated with interferon and nine with purine analogs.

FIGS. 4A-4C shows that CD38 promotes HCL growth. FIG. 4A shows day 0 cultures of JOK-CD38-KO and JOK-CD38-WT initiated at a density of 5×10$^5$ cells per ml. Thereafter, cells were counted at day 2, 4, 6 and 8. At each time point, the number of JOK-CD38-WT cells (CD38-WT) was assigned a value of 100 and the number of JOK-CD38-KO cells (CD38-KO) calculated as a percentage of this value. Histograms represent the mean±s.d. of three experiments. At day 4, 6 and 8 the number of JOK-CD38-KO cells was significantly fewer than the number of JOK-CD38-WT cells (Paired Student t-test: P=0.0257, 0.0342 and 0.0036, respectively). FIG. 4B shows the rate of cell division assessed by measuring the percentage of cells in culture that incorporated EdU and thus designated to be in the S phase of the cell cycle. Histograms represent the mean±s.d. of three experiments. There is no significant difference between cultures of JOK-CD38-WT (CD38-WT) and JOK-CD38-KO (CD38-KO) (Paired Student t-test: P=0.1571). FIG. 4C shows the rate of cell death assessed by determining the percentage of cells in 72 hour cultures that expressed annexin V and also stained with propidium iodide. These cells were designated to be undergoing apoptosis. Histograms represent the mean±s.d. of four experiments. The percentage of cells undergoing apoptosis was significantly higher in cultures of JOK-CD38-KO (CD38-KO) than in cultures of JOK-CD38-WT (CD38-WT) (Paired Student t-test: P=0.0091).

FIG. 6A shows eight mice of the strain NOD.Cg-Prkdc$^{scid}$ IL2rγ$^{tm1Wjl}$/SzJ were injected subcutaneously with 5×10$^6$ JOK-CD38-WT (CD38-WT) and seven mice of the same strain were identically injected with JOK-CD38-KO (CD38-KO). After 4 weeks, the resulting subcutaneous tumors were dissected and their volumes calculated from dimension measurements. The tumor volume in each mouse is presented as a filled square. Horizontal dotted lines show the mean tumor volumes produced by JOK-CD38-WT and JOK-CD38-KO. Vertical bars delineate the s.d. of these volumes. The mean volume of tumors produced by JOK-CD38-KO was significantly smaller than that of those produced by JOK-CD38-WT (Unpaired Student t-test: P=0.0525). FIG. 6B shows the weights of the same tumors where volume was calculated. The mean weight of tumors produced by JOK-CD38-KO was significantly less than that of those produced by JOK-CD38-WT (Unpaired Student t-test: P=0.0273).

FIG. 8 shows the DNA sequence of the wild-type CD38 gene in the HCL cell line JOK-1 aligned to the CD38 gene sequences in the six JOK-1 clones that were mixed to produce JOK-CD38-KO. Numbering of the wild-type CD38 gene is relative to the transcription start site at +1. The translation start site is at nucleotide +56. Nucleotides that are deleted in the clones comprising JOK-CD38-KO are indicated by dashes and nucleotides that are inserted are indicated by text within boxes. 173 nucleotides are deleted in JOK-CD38-KO.6. Each of the deletions or insertions into the CD38 gene shifted the reading-frame of the coding region so as to introduce premature translation stop codons into the mRNA. The nucleotides within the wild-type CD38 gene that ZFN was designed to bind to produce the frameshift mutations are indicated by bold lettering.

DETAILED DESCRIPTION

Figure 1B:
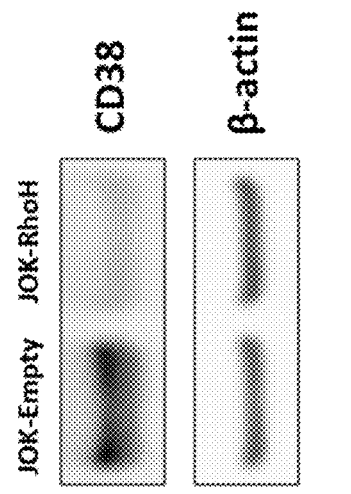
FIGS. 1A-1C show the induction of RhoH in HCL down-regulates CD38 expression.

Aspects of the disclosure relate to identifying a hematopoietic disorder-associated molecule in a hematopoietic cell. In some aspects, the disclosure is based on the finding that modulating the expression of the intracellular signaling molecule RhoH in a hematopoietic cell identifies novel diagnostics and therapeutic targets. As used herein, a hematopoietic cell refers to a blood cell derived from mesoderm, including mature cells and their respective immature precursors. Hematopoietic cells include the following: mesophilic myelocytes, basophils, B cells, burst-forming unit (BFU) cells (BFU-E and BFU-Mk), colony-forming unit (CFU) cells (CFU-bas, CFU-E, CFU-Eo, CFU-G, CFU-GEMM, CFU-GM, and CFU-Mk), common dendritic progenitors, common lymphoid progenitors, common myeloerythroid progenitors, common myeloid progenitors, common myelolymphoid progenitors, double-negative (DN) T cells (DN1, DN2, DN3, and DN4), double-positive (DP) T cells, eosinophilic myelocytes, eosinophils, erythrocytes, lymphoid stem cells, lymphoid-related dendritic cells, macrophages, mast cells, megakaryocytes, memory B cells, memory T cells, monoblasts, monocytes, myeloblast, myeloid stem cells, myeloid-related dendritic cells, neutrophilic myelocytes, neutrophils, natural killer (NK) cells, NK T-cells, platelets, pro-B lymphocytes (pro-B1 cells and pro- B2 cells), proerythrocytes, promonocytes, regulatory T cells, T cells, and T-helper cells (Th0, Th1, Th2, Th3, and Th17).

As used herein, Ras homolog family member H (RhoH), is a protein of the Ras superfamily of guanosine triphosphate (GTP)-metabolizing enzymes. It is expressed in hematopoietic cells, where it regulates cell growth and survival. Hypermutations or misexpressions of its gene have been implicated in some leukemias and lymphomas. The RhoH sequence is as follows:

```
                                             (SEQ ID NO: 1)
MLSSIKCVLVGDSAVGKTSLLVRFTSETFPEAYKPTVYENTGVDVFMDGI

QISLGLWDTAGNDAFRSIRPLSYQQADVVLMCYSVANHNSFLNLKNKWIG

EIRSNLPCTPVLVVATQTDQREMGPHRASCVNAMEGKKLAQDVRAKGYLE

CSALSNRGVQQVFECAVRTAVNQARRRNRRRLFSINECKIF
```

Some aspects of the disclosure involve identifying a hematopoietic cell having abnormal RhoH level. In some embodiments an abnormal RhoH level may be an increased level relative to a control level (e.g., in a control cell). By increased it means that the RhoH level in the cell has a statistically significant increase from the level in a control cell (control level). For example, a statistically significant increase may be a RhoH level in a cell is at least 10%, at least 25%, at least 50%, at least 100%, at least 250%, at least 500%, or at least 1000% higher than a control level. Similarly, a statistically significant increase may be a RhoH level that is at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100-fold, or more higher than a control level (e.g., in a control cell).

In some embodiments an abnormal RhoH level may be a decreased level relative to a control level (e.g., in a control cell). By decreased it means that the RhoH level in the cell has a statistically significant decrease from the level in a control level (e.g., in a control cell). For example, a statistically significant decrease may be a RhoH level in a cell is at least 10%, at least 25%, at least 50%, at least 75%, at least 90%, at least 95%, or undetectable as compared to the level that in a control cell. Similarly, a statistically significant decrease may be a RhoH level that is at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100-fold, or more low than that a control level. In some embodiments, the RhoH level is decreased to be undetectable or below a background/noise level obtained using standard methods of detection (e.g., Western blot, northern blot, quantitative RT-PCR, or immunohistochemistry).

A RhoH control level in a control cell is a level in a healthy hematopoietic cell or the average in a population of hematopoietic cells obtained from a healthy subject or a population of healthy subjects. A healthy subject is a subject that is apparently free of disease and has no history of disease, such as a hematopoietic disorder Statistically significance may be identified by using an appropriate statistical test. Tests for statistical significance are well known in the art and are exemplified in Applied Statistics for Engineers and Scientists by Petruccelli, Chen and Nandram 1999 Reprint Ed. In some embodiments, the differentially expressed biomarkers are selected using a criteria of false discovery rate <0.2.

Aspects of the disclosure involve restoring RhoH level to a control level. In some embodiments restoring RhoH level in a cell involves increasing a RhoH level (e.g., increasing RhoH expression) in a cell to a control level. Methods of increasing RhoH level include but are not limited to: introducing of recombinant RhoH protein, RhoH mRNA, RhoH encoding plasmids and viruses, micro-RNAs and/or small molecules and/or peptides and/or proteins that stabilize RhoH mRNA and/or protein, inhibiting molecular entities that destabilize RhoH mRNA and/or protein, genomic editing to inhibit endogenous RhoH gene inhibitory control elements and/or activating endogenous RhoH gene activator control elements and/or introducing into the RhoH gene recombinant activator control elements, epigenetic modifiers that activate the RhoH gene, inhibitors of epigenetic modifiers that inhibit the RhoH gene.

In some embodiments restoring RhoH level in a cell involves decreasing a RhoH level (e.g., decreasing RhoH expression) in a cell to a control level. Methods of decreasing RhoH level include but are not limited to: introducing anti-RhoH antibodies, RhoH anti-sense mRNA and/or oligonucleotides, anti-sense RhoH encoding plasmids and viruses, micro-RNAs and/or small molecules and/or peptides and/or proteins that destabilize RhoH mRNA and/or protein, inhibiting molecular entities that stabilize RhoH mRNA and/or protein, genomic editing to inhibit endogenous RhoH gene activator control elements and/or activating endogenous RhoH gene inhibitor control elements and/or introducing into the RhoH gene recombinant inhibitor control elements, epigenetic modifiers that inhibit the RhoH gene, inhibiting epigenetic modifiers that activate the RhoH gene.

Aspects of the disclosure relate to identifying a hematopoietic disorder-associated molecule. The hematopoietic disorder-associated molecule may be a protein, polypeptide, messenger RNA (mRNA), microRNA (miRNA), or long non-coding RNA (lncRNA).

As used herein, a protein refers to a biopolymer composed of amino acid or amino acid analog subunits, typically some or all of the 20 common amino acids found in biological proteins. The amino acid chain, polypeptide, can be of any length, including full-length proteins, wherein the amino acids are linked by covalent peptide bonds.

As used herein, a peptide refers to a molecule of 2 to 100 or more amino acids linked by covalent peptide bonds. Peptides may contain random and or flexible conformations, including random coils; and can lack the stable conformations observed in larger proteins or polypeptides, which are achieved via secondary and tertiary structures.

As used herein, RNA refers to ribonucleic acid, a polymeric molecule containing nucleotide bases, in either single-stranded or double-stranded form.

As used herein, a messenger RNA (mRNA) refers to any polynucleotide without intron segments, which is capable of being translated to produce a protein in vitro, in vivo, in situ, or ex vivo.

As used herein, a microRNA (miRNA) refers to a non-coding RNA molecule of 21 to 25 nucleotides that may function in RNA silencing and the post-translational regulation of gene expression.

As used herein, a lncRNA (long non-coding RNA) refers to a non-coding RNA molecule longer than 200 nucleotides that may be located separate from protein coding genes (long intergenic ncRNA) or reside near or within protein coding genes. The lncRNA includes many mRNA characteristics, including 5' capping, splicing, and polyadenylation, but does has little or no open reading frame.

Examples of hematopoietic disorder-associated molecules include, for example, those listed in the following table:

| Gene Symbol | Description | GenBank No. |
|---|---|---|
| | ALU2_HUMAN (P39189) Alu subfamily SB sequence contamination warning entry, partial (5%) [THC2302062] | XM_370835 |
| | ALU5_HUMAN (P39192) Alu subfamily SC sequence contamination warning entry, partial (6%) [THC2281591] | |
| | ALU7_HUMAN (P39194) Alu subfamily SQ sequence contamination warning entry, partial (9%) | |
| | apolipoprotein B48 receptor; *Homo sapiens* apolipoprotein B48 receptor (APOB48R), mRNA. | NM_182804 |
| | BIC transcript | NR_001458 |
| | C40201 artifact-warning sequence (translated ALU class C) - human {*Homo sapiens*;}, partial (11%) [THC2317149] | |
| | Carboxypeptidase, vitellogenic-like | |
| | caspase-1 dominant-negative inhibitor pseudo-ICE | NM_001017534 |
| | CBF1 interacting corepressor | NM_004882 |
| | CDNA FLJ30652 fis, clone DFNES2000011 | |
| | CDNA FLJ37310 fis, clone BRAMY2016706 | |
| | CDNA: FLJ23228 fis, clone CAE06654 | |
| | Clone FBA1 Cri-du-chat region mRNA | |
| | Clone pp6455 unknown mRNA | |
| | defective in sister chromatid cohesion homolog 1 (*S. cerevisiae*) | NM_024094 |
| | Ecotropic viral integration site 5 | |
| | Expressed Sequence Tag (EST) | BM819787 |
| | Expressed Sequence Tag (EST) | BG112935 |
| | Expressed Sequence Tag (EST) | BQ049338 |
| | extracellular active factor; neuronal death blocker of Alzheimer's disease insults; *Homo sapiens* Humanin (HN1) mRNA, complete cds. | |
| | FABE_HUMAN (Q01469) Fatty acid-binding protein, epidermal (E-FABP) (Psoriasis-associated fatty acid-binding protein homolog) (PA-FABP), partial (53%) [THC2302865] | |
| | FLJ35767 protein | NM_207459 |
| | full-length cDNA clone CS0DL009YB17 of B cells (Ramos cell line) Cot 25-normalized of *Homo sapiens* (human). [CR593568] | |
| | *H. sapiens* rearranged VDJ region (BEL14). [X81724] | XM_370973 |
| | *H. sapiens* TAFII105 mRNA, partial. [Y09321] | XM_290809 |
| | *Homo sapiens* adaptor-related protein complex 1, sigma 3 subunit (AP1S3), mRNA [NM_178814] | NM_178814 |
| | *Homo sapiens* androgen-induced proliferation inhibitor (APRIN), transcript variant 2, mRNA [NM_015928] | NM_015928 |
| | *Homo sapiens* aspartyl protease 3 mRNA, partial cds. [AF200344] | XR_000169 |
| | *Homo sapiens* cDNA FLJ27224 fis, clone SYN04819. [AK130734] | |
| | *Homo sapiens* cDNA FLJ31247 fis, clone KIDNE2005296, weakly similar to ACTIN, CYTOPLASMIC 1. [AK055809] | |
| | *Homo sapiens* cDNA FLJ31859 fis, clone NT2RP7001231. [AK056421] | |
| | *Homo sapiens* cDNA FLJ38080 fis, clone CTONG2016185. [AK095399] | |
| | *Homo sapiens* chordin (CHRD), transcript variant 2, mRNA [NM_177978] | NM_177978 |
| | *Homo sapiens* chromosome 20 open reading frame 35 (C20orf35), mRNA [NM_018478] | NM_018478 |
| | *Homo sapiens* chromosome 6 open reading frame 54 (C6orf54), mRNA [NM_014354] | NM_014354 |
| | *Homo sapiens* CSAG family, member 4 (CSAG4), mRNA [NM_001025306] | NM_001025306 |
| | *Homo sapiens* Fc receptor-like 2 (FCRL2), mRNA [NM_138739] | NM_138739 |
| | *Homo sapiens* Fc receptor-like and mucin-like 2 (FCRLM2), mRNA [NM_152378] | NM_152378 |
| | *Homo sapiens* HSPC053 mRNA, complete cds. [AF161538] | |
| | *Homo sapiens* hypothetical protein LOC90925 (LOC90925), mRNA [NM_175870] | NM_175870 |

-continued

| Gene Symbol | Description | GenBank No. |
|---|---|---|
| | *Homo sapiens* mRNA for KIAA1023 protein, partial cds. [AB028946] | |
| | *Homo sapiens* mRNA for KIAA1162 protein, partial cds. [AB032988] | |
| | *Homo sapiens* PHD finger protein 2 (PHF2), transcript variant 2, mRNA [NM_024517] | NM_024517 |
| | *Homo sapiens* zinc finger homeobox 2 (ZFHX2), mRNA [NM_033400] | NM_033400 |
| | *Homo sapiens*, clone IMAGE: 4285740, mRNA. [BC006008] | XM_113962 |
| | *Homo sapiens*, clone IMAGE: 4445372, mRNA | |
| | *Homo sapiens*, Similar to snail homolog 3 (*Drosophila*), clone IMAGE: 5209145, mRNA, partial cds. [BC041461] | XM_370995 |
| | human full-length cDNA clone CS0DL004YM19 of B cells (Ramos cell line) of *Homo sapiens* (human). [BX248300] | |
| | Human mRNA for T-cell receptor V beta gene segment V-beta-13, clone IGRb14. [X58809] | |
| | hypothetical gene supported by AK124333 | XM_379648 |
| | Hypothetical gene supported by AK128882 | XM_499014 |
| | hypothetical protein FLJ20186 | NM_017702 |
| | hypothetical protein FLJ22814 | |
| | hypothetical protein LOC134145 | NM_199133 |
| | hypothetical protein LOC283454 | |
| | hypothetical protein LOC643401 | |
| | hypothetical protein MGC14376 | NM_032895 |
| | Immunoglobulin heavy constant gamma 1 (G1m marker) | |
| | immunoglobulin kappa variable 1/OR2-108 (non-functional) [Source: HGNC Symbol; Acc: HGNC: 5767] | |
| | immunoglobulin kappa variable 1/OR9-2 (pseudogene) [Source: HGNC Symbol; Acc: HGNC: 49466] | |
| | KIAA1666 protein | XM_036936 |
| | KIAA1706 protein | NM_030636 |
| | LSM14B, SCD6 homolog B (*S. cerevisiae*) | |
| | macrophage expressed gene 1 | XM_166227 |
| | MEX3A protein | XM_044166 |
| | NOA1_HUMAN (Q9NY12) Nucleolar protein family A member 1 (snoRNP protein GAR1) (H/ACA ribonucleoprotein GAR1), partial (18%) [THC2314822] | |
| | O13102 (O13102) Activin type IIB receptor precursor, partial (5%) [THC2372182] | |
| | phospholysine phosphohistidine inorganic pyrophosphate phosphatase | NM_022126 |
| | plasma glutamate carboxypeptidase | NM_016134 |
| | predicted protein of HQ1995; *Homo sapiens* PRO1995 mRNA, complete cds. | |
| | PREDICTED: *Homo sapiens* similar to Ig heavy chain V-III region VH26 precursor (LOC390714), mRNA [XM_372632] | XM_372632 |
| | Q5VT28_HUMAN (Q5VT28) Family with sequence similarity 27, member B (Family with sequence similarity 27, member A) (Family with sequence similarity 27, member C), partial (85%) | |
| | Q69Z36 (Q69Z36) MKIAA2009 protein (Fragment), partial (8%) [THC2430293] | |
| | Q6DD14 (Q6DD14) MGC80451 protein, partial (40%) [THC2340803] | |
| | Q7Z5X4 (Q7Z5X4) Intermediate filament-like protein MGC: 2625, isoform 1, partial (12%) [THC2301370] | |
| | Q7ZX66 (Q7ZX66) RNPC7 protein (Fragment), partial (9%) [THC2309960] | |
| | Q9BYX7 (Q9BYX7) FKSG30, partial (41%) [THC2364880] | |
| | Q9F8M7 (Q9F8M7) DTDP-glucose 4,6-dehydratase (Fragment), partial (11%) [THC2406944] | |
| | Q9H1B6 (Q9H1B6) Xylosyltransferase I (Fragment), partial (8%) [THC2341118] | |
| | Similar to ATP-binding cassette, sub-family A (ABC1), member 17 | XM_498629 |

-continued

| Gene Symbol | Description | GenBank No. |
|---|---|---|
| | similar to common salivary protein 1 | NM_145252 |
| | Synthetic construct Homo sapiens gateway clone IMAGE: 100021072 3' read RPS3A mRNA | CU688199 |
| | telomerase reverse transcriptase; synonyms: TP2, TRT, EST2, TCS1, hEST2; isoform 1 is encoded by transcript variant 1; telomerase catalytic subunit; Homo sapiens telomerase reverse transcriptase (TERT), transcript variant 1, mRNA. | NM_003219 |
| | trophoblast-derived noncoding RNA UB30_HUMAN (Q70CQ3) Ubiquitin carboxyl-terminal hydrolase 30 (Ubiquitin thiolesterase 30) (Ubiquitin-specific processing protease 30) (Deubiquitinating enzyme 30), partial (4%) [THC2311946] yy53b06.r1 Soares_multiple_sclerosis_2NbHMSP Homo sapiens cDNA clone IMAGE: 277235 5', mRNA sequence. Zinc finger protein 718 | NR_002802 |
| ABCA1 | ATP-binding cassette, sub-family A (ABC1), member 1 | NM_005502 |
| ABTB2 | ankyrin repeat and BTB (POZ) domain containing 2 | NM_145804 |
| ACTC1 | actin, alpha, cardiac muscle 1 | NM_005159 |
| ACTG1 | actin, gamma 1 | NM_001614 |
| ACTG2 | actin, gamma 2, smooth muscle, enteric | NM_001615 |
| ACY3 | aspartoacylase (aminocyclase) 3 | NM_080658 |
| AEBP2 | AE binding protein 2 | NM_153207 |
| AICDA | activation-induced cytidine deaminase | NM_020661 |
| AKR1C1 | aldo-keto reductase family 1, member C1 (dihydrodiol dehydrogenase 1; 20-alpha (3-alpha)-hydroxysteroid dehydrogenase) | NM_001353 |
| ALPK3 | Homo sapiens alpha-kinase 3 (ALPK3), mRNA | NM_020778 |
| ANKRD25 | ankyrin repeat domain 25 | NM_015493 |
| ANKRD47 | ankyrin repeat domain 47 | NM_198471 |
| ANKRD55 | ankyrin repeat domain 55 | NM_024669 |
| ANXA1 | annexin A1 | NM_000700 |
| APOL3 | apolipoprotein L, 3 | NM_145641 |
| ARHGAP25 | Rho GTPase activating protein 25 | NM_001007231 |
| ARNTL | Homo sapiens aryl hydrocarbon receptor nuclear translocator-like (ARNTL), transcript variant 3, mRNA | NM_001030273 |
| ATAD2 | ATPase family, AAA domain containing 2 | NM_014109 |
| ATP10D | ATPase, Class V, type 10D | NM_020453 |
| BACE2 | beta-site APP-cleaving enzyme 2 | NM_012105 |
| BANK1 | B-cell scaffold protein with ankyrin repeats 1 | NM_017935 |
| BARX1 | Homo sapiens BARX homeobox 1 (BARX1), mRNA | NM_021570 |
| BCAS3 | breast carcinoma amplified sequence 3 | NM_017679 |
| BCHE | butyrylcholinesterase | NM_000055 |
| BCL2A1 | BCL2-related protein A1 | NM_004049 |
| BIRC3 | baculoviral IAP repeat-containing 3 | NM_001165 |
| BLK | B lymphoid tyrosine kinase | NM_001715 |
| BMF | Bcl2 modifying factor | NM_001003940 |
| BMP7 | bone morphogenetic protein 7 (osteogenic protein 1) | NM_001719 |
| BRDG1; STAP1 | BCR downstream signaling 1 | NM_012108 |
| BTG2 | BTG family, member 2 | NM_006763 |
| C10orf10 | chromosome 10 open reading frame 10 | NM_007021 |
| C10orf33 | chromosome 10 open reading frame 33 | NM_032709 |
| C11orf41 | chromosome 11 open reading frame 41 | XM_039515 |
| C11orf74 | Homo sapiens chromosome 11 open reading frame 74 (C11orf74), transcript variant 4, mRNA | NM_138787 |
| C14orf112 | chromosome 14 open reading frame 112 | NM_016468 |
| C16orf45 | Homo sapiens chromosome 16 open reading frame 45 (C16orf45), transcript variant 1, mRNA | NM_033201 |
| C18orf10 | chromosome 18 open reading frame 10 | NM_015476 |
| C19orf51 | chromosome 19 open reading frame 51 | NM_178837 |
| C1orf38 | chromosome 1 open reading frame 38 | NM_004848 |
| C1orf54 | chromosome 1 open reading frame 54 | NM_024579 |
| C20orf67 | chromosome 20 open reading frame 67 | NM_022104 |
| C21orf34 | chromosome 21 open reading frame 34 | NM_001005733 |

-continued

| Gene Symbol | Description | GenBank No. |
|---|---|---|
| C21orf34 | chromosome 21 open reading frame 34 | NM_001005732 |
| C3orf39 | chromosome 3 open reading frame 39 | NM_032806 |
| C4orf32 | chromosome 4 open reading frame 32 | NM_152400 |
| C6orf192 | chromosome 6 open reading frame 192 | NM_052831 |
| C8orf88 | *Homo sapiens* chromosome 8 open reading frame 88 (C8orf88), mRNA | NM_001190972 |
| CARD10 | caspase recruitment domain family, member 10 | NM_014550 |
| CARD11 | caspase recruitment domain family, member 11 | NM_032415 |
| CARD14 | caspase recruitment domain family, member 14 | NM_024110 |
| CARD6 | caspase recruitment domain family, member 6 | NM_032587 |
| CASP1 | caspase 1, apoptosis-related cysteine peptidase (interleukin 1, beta, convertase) | NM_033292 |
| CASP4 | caspase 4, apoptosis-related cysteine peptidase | NM_033306 |
| CASP5 | caspase 5, apoptosis-related cysteine peptidase | NM_004347 |
| CCDC104 | coiled-coil domain containing 104 | NM_080667 |
| CCDC3 | *Homo sapiens* coiled-coil domain containing 3 (CCDC3), transcript variant 1, mRNA | NM_031455 |
| CCL1 | chemokine (C-C motif) ligand 1 | NM_002981 |
| CCL3 | chemokine (C-C motif) ligand 3 | NM_002983 |
| CCL3L3 | chemokine (C-C motif) ligand 3-like 3 | NM_001001437 |
| CCL4 | chemokine (C-C motif) ligand 4 | NM_002984 |
| CCL5 | chemokine (C-C motif) ligand 5 | NM_002985 |
| CCNA1 | cyclin A1 | NM_003914 |
| CCNG2 | cyclin G2 | NM_004354 |
| CCR4 | chemokine (C-C motif) receptor 4 | NM_005508 |
| CCRL2 | chemokine (C-C motif) receptor-like 2 | NM_003965 |
| CD2 | CD2 molecule | NM_001767 |
| CD22 | CD22 molecule | NM_001771 |
| CD274 | CD274 molecule | NM_014143 |
| CD300A | CD300a molecule | NM_007261 |
| CD38 | CD38 molecule | NM_001775 |
| CD52 | CD52 molecule | NM_001803 |
| CD68 | CD68 molecule | NM_001251 |
| CD74 | CD74 molecule, major histocompatibility complex, class II invariant chain | NM_004355 |
| CD82 | CD82 molecule | NM_002231 |
| CD83 | CD83 molecule | NM_004233 |
| CD93 | *Homo sapiens* CD93 molecule (CD93), mRNA | NM_012072 |
| CDC42EP1 | *Homo sapiens* CDC42 effector protein (Rho GTPase binding) 1 (CDC42EP1), mRNA | NM_152243 |
| CDC42EP3 | *Homo sapiens* CDC42 effector protein (Rho GTPase binding) 3 (CDC42EP3), transcript variant 1, mRNA | NM_006449 |
| CDC42EP4 | CDC42 effector protein (Rho GTPase binding) 4 | NM_012121 |
| CDKN2C | *Homo sapiens* cyclin-dependent kinase inhibitor 2C (p18, inhibits CDK4) (CDKN2C), transcript variant 2, mRNA | NM_078626 |
| CEACAM1 | carcinoembryonic antigen-related cell adhesion molecule 1 (biliary glycoprotein) | NM_001712 |
| CEBPB | CCAAT/enhancer binding protein (C/EBP), beta | NM_005194 |
| CEP135 | centrosomal protein 135 kDa | NM_025009 |
| CFHR1 | complement factor H-related 1 | NM_002113 |
| CFTR | cystic fibrosis transmembrane conductance regulator (ATP-binding cassette sub-family C, member 7) | NM_000492 |
| CLCF1 | cardiotrophin-like cytokine factor 1 | NM_013246 |
| CLCN2 | chloride channel 2 | NM_004366 |
| CLIC4 | chloride intracellular channel 4 | NM_013943 |
| COL15A1 | *Homo sapiens* collagen, type XV, alpha 1 (COL15A1), mRNA | NM_001855 |
| COL6A2 | *Homo sapiens* collagen, type VI, alpha 2 (COL6A2), transcript variant 2C2a, mRNA | NM_058174 |
| CPNE5 | copine V | NM_020939 |
| CR2 | complement component (3d/Epstein Barr virus) receptor 2 | NM_001006658 |
| CRTAM | cytotoxic and regulatory T cell molecule | NM_019604 |
| CSAG1 | chondrosarcoma associated gene 1 | NM_153479 |
| CSAG2 | CSAG family, member 2 | NM_004909 |
| CSAG3A | CSAG family, member 3A | NM_203311 |
| CSF1R | colony stimulating factor 1 receptor, formerly | NM_005211 |

-continued

| Gene Symbol | Description | GenBank No. |
|---|---|---|
| | McDonough feline sarcoma viral (v-fms) oncogene homolog | |
| CSTA | cystatin A (stefin A) | NM_005213 |
| CTSS | cathepsin S | NM_004079 |
| CUTL2 | cut-like 2 (*Drosophila*) | NM_015267 |
| CX3CR1 | chemokine (C-X3-C motif) receptor 1 | NM_001337 |
| CXCR7 | chemokine (C-X-C motif) receptor 7 | NM_020311 |
| CXorf9 | chromosome X open reading frame 9 | NM_018990 |
| CXXC5 | CXXC finger 5 | NM_016463 |
| CYFIP1 | cytoplasmic FMR1 interacting protein 1 | NM_014608 |
| CYP1B1 | cytochrome P450, family 1, subfamily B, polypeptide 1 | NM_000104 |
| CYP2U1 | cytochrome P450, family 2, subfamily U, polypeptide 1 | NM_183075 |
| DEFB123 | defensin, beta 123 | NM_153324 |
| DERL1 | Der1-like domain family, member 1 | NM_024295 |
| DHDH | dihydrodiol dehydrogenase (dimeric) | NM_014475 |
| DHRS2 | dehydrogenase/reductase (SDR family) member 2 | NM_182908 |
| DISP2 | dispatched homolog 2 (*Drosophila*) | NM_033510 |
| DLGAP4 | discs, large (*Drosophila*) homolog-associated protein 4 | NM_014902 |
| DNMT3A | DNA (cytosine-5-)-methyltransferase 3 alpha | NM_175630 |
| DNMT3B | DNA (cytosine-5-)-methyltransferase 3 beta | NM_175850 |
| DOCK10 | dedicator of cytokinesis 10 | NM_014689 |
| DPP4 | dipeptidyl-peptidase 4 (CD26, adenosine deaminase complexing protein 2) | NM_001935 |
| DSTN | destrin (actin depolymerizing factor) | NM_001011546 |
| DUSP2 | dual specificity phosphatase 2 | NM_004418 |
| DUSP5P1 | *Homo sapiens* dual specificity phosphatase 5 pseudogene 1 (DUSP5P1), non-coding RNA | NR_002834 |
| EGR2 | early growth response 2 (Krox-20 homolog, *Drosophila*) | NM_000399 |
| EIF3S3 | eukaryotic translation initiation factor 3, subunit 3 gamma, 40 kDa | NM_003756 |
| ELL2 | elongation factor, RNA polymerase II, 2 | NM_012081 |
| EMID1 | EMI domain containing 1 | NM_133455 |
| EMP3 | epithelial membrane protein 3 | NM_001425 |
| EPS8L1 | EPS8-like 1 | NM_133180 |
| ERO1LB | ERO1-like beta (*S. cerevisiae*) | NM_019891 |
| EVL | Enah/Vasp-like | NM_016337 |
| EXO5 | *Homo sapiens* exonuclease 5 (EXO5), mRNA | NM_022774 |
| F2RL3 | coagulation factor II (thrombin) receptor-like 3 | NM_003950 |
| FAM129C | family with sequence similarity 129, member C | NM_173544 |
| FAM59A | family with sequence similarity 59, member A | NM_022751 |
| FAT1 | *Homo sapiens* FAT atypical cadherin 1 (FAT1), mRNA | NM_005245 |
| FBLN5 | fibulin 5 | NM_006329 |
| FCER2 | Fc fragment of IgE, low affinity II, receptor for (CD23) | NM_002002 |
| FCN1 | ficolin (collagen/fibrinogen domain containing) 1 | NM_002003 |
| FCRL2 | Fc receptor-like 2 | NM_138738 |
| FCRL3 | Fc receptor-like 3 | NM_052939 |
| FGF18 | fibroblast growth factor 18 | NM_003862 |
| FHOD3 | formin homology 2 domain containing 3 | NM_025135 |
| FNDC3B | fibronectin type III domain containing 3B | NM_022763 |
| FOSB | FBJ murine osteosarcoma viral oncogene homolog B | NM_006732 |
| FOXK1 | *Homo sapiens* forkhead box K1 (FOXK1), mRNA | NM_001037165 |
| FSD1 | fibronectin type III and SPRY domain containing 1 | NM_024333 |
| GADD45B | growth arrest and DNA-damage-inducible, beta | NM_015675 |
| GAS7 | growth arrest-specific 7 | NM_201433 |
| GATA2-AS1 | *Homo sapiens* cDNA: FLJ21000 fis, clone CAE03359. | AK024653 |
| GBP1 | guanylate binding protein 1, interferon-inducible, 67 kDa | NM_002053 |
| GCA | grancalcin, EF-hand calcium binding protein | NM_012198 |
| GDF15 | growth differentiation factor 15 | NM_004864 |
| GDPD5 | glycerophosphodiester phosphodiesterase domain containing 5 | NM_030792 |
| GIMAP1 | *Homo sapiens* GTPase, IMAP family member 1 (GIMAP1), mRNA | NM_130759 |

-continued

| Gene Symbol | Description | GenBank No. |
| --- | --- | --- |
| GIMAP2 | GTPase, IMAP family member 2 | NM_015660 |
| GLI1 | glioma-associated oncogene homolog 1 (zinc finger protein) | NM_005269 |
| GM2A | GM2 ganglioside activator | NM_000405 |
| GPNMB | glycoprotein (transmembrane) nmb | NM_001005340 |
| GPR109B | G protein-coupled receptor 109B | NM_006018 |
| GPR171 | G protein-coupled receptor 171 | NM_013308 |
| GPR179 | *Homo sapiens* G protein-coupled receptor 179 (GPR179), mRNA | NM_001004334 |
| GPR30 | G protein-coupled receptor 30 | NM_001505 |
| GPR56 | G protein-coupled receptor 56 | NM_201525 |
| GRB10 | growth factor receptor-bound protein 10 | NM_001001555 |
| GRIN2C | glutamate receptor, ionotropic, N-methyl D-aspartate 2C | NM_000835 |
| GRN | granulin | NM_002087 |
| GRTP1 | growth hormone regulated TBC protein 1 | NM_024719 |
| HAVCR2 | hepatitis A virus cellular receptor 2 | NM_032782 |
| HES6 | hairy and enhancer of split 6 (*Drosophila*) | NM_018645 |
| HHAT | hedgehog acyltransferase | NM_018194 |
| HIST1H2BK | histone cluster 1, H2bk | NM_080593 |
| HIVEP3 | human immunodeficiency virus type I enhancer binding protein 3 | NM_024503 |
| HLA-DMA | major histocompatibility complex, class II, DM alpha | NM_006120 |
| HLA-DOA | major histocompatibility complex, class II, DO alpha | NM_002119 |
| HLA-DQA2 | major histocompatibility complex, class II, DQ alpha 2 | NM_020056 |
| HLA-DRB1 | major histocompatibility complex, class II, DR beta 1 | NM_002124 |
| HLA-DRB3 | major histocompatibility complex, class II, DR beta 3 | NM_022555 |
| HLA-DRB5 | major histocompatibility complex, class II, DR beta 5 | NM_002125 |
| HM13 | histocompatibility (minor) 13 | NM_178582 |
| HRASLS2 | HRAS-like suppressor 2 | NM_017878 |
| HRK | harakiri, BCL2 interacting protein (contains only BH3 domain) | NM_003806 |
| HSH2D | *Homo sapiens* hematopoietic SH2 domain containing (HSH2D), transcript variant 1, mRNA | NM_032855 |
| HSPA4 | Heat shock 70 kDa protein 4 | |
| HSPA6 | heat shock 70 kDa protein 6 (HSP70B') | NM_002155 |
| ICAM1 | intercellular adhesion molecule 1 (CD54), human rhinovirus receptor | NM_000201 |
| IER5L | immediate early response 5-like | NM_203434 |
| IFI35 | interferon-induced protein 35 | NM_005533 |
| IGF1R | insulin-like growth factor 1 receptor | |
| IGHV1-69 | immunoglobulin heavy variable 1-69 | |
| IGJ | immunoglobulin J polypeptide, linker protein for immunoglobulin alpha and mu polypeptides | NM_144646 |
| IL13 | interleukin 13 | NM_002188 |
| IL17RC | *Homo sapiens* interleukin 17 receptor C (IL17RC), transcript variant 2, mRNA | NM_153461 |
| IL1R2 | interleukin 1 receptor, type II | NM_004633 |
| IL23A | interleukin 23, alpha subunit p19 | NM_016584 |
| IL26 | interleukin 26 | NM_018402 |
| IL3RA | interleukin 3 receptor, alpha (low affinity) | NM_002183 |
| IL4 | interleukin 4 | NM_000589 |
| IL4I1 | interleukin 4 induced 1 | NM_172374 |
| IL7R | interleukin 7 receptor | NM_002185 |
| INPP4B | inositol polyphosphate-4-phosphatase, type II, 105 kDa | NM_003866 |
| IQCG | IQ motif containing G | NM_032263 |
| IQSEC1 | IQ motif and Sec7 domain 1 | NM_014869 |
| ITGAX | integrin, alpha X (complement component 3 receptor 4 subunit) | NM_000887 |
| ITGB7 | integrin, beta 7 | NM_000889 |
| JAG1 | jagged 1 (Alagille syndrome) | NM_000214 |
| JUN | jun oncogene | NM_002228 |
| JUP | junction plakoglobin | NM_002230 |
| KATNAL2 | katanin p60 subunit A-like 2 | NM_031303 |
| KCNJ16 | potassium inwardly-rectifying channel, subfamily J, member 16 | NM_170741 |
| KCNMA1 | potassium large conductance calcium-activated channel, subfamily M, alpha member 1 | NM_002247 |

-continued

| Gene Symbol | Description | GenBank No. |
|---|---|---|
| KCNN4 | Homo sapiens potassium channel, calcium activated intermediate/small conductance subfamily N alpha, member 4 (KCNN4), mRNA | NM_002250 |
| KCNQ5-IT1 | Homo sapiens KCNQ5 intronic transcript 1 (non-protein coding) (KCNQ5-IT1), long non-coding RNA | NR_120503 |
| KIAA0196 | KIAA0196 | NM_014846 |
| KIR2DL2 | killer cell immunoglobulin-like receptor, two domains, long cytoplasmic tail, 2 | NM_014219 |
| KIR2DL4 | killer cell immunoglobulin-like receptor, two domains, long cytoplasmic tail, 4 | NM_002255 |
| KIR2DS1 | killer cell immunoglobulin-like receptor, two domains, short cytoplasmic tail, 1 | NM_014512 |
| KIR2DS2 | killer cell immunoglobulin-like receptor, two domains, short cytoplasmic tail, 2 | NM_012312 |
| KIR2DS4 | killer cell immunoglobulin-like receptor, two domains, short cytoplasmic tail, 4 | NM_178228 |
| KIR3DL1 | killer cell immunoglobulin-like receptor, three domains, long cytoplasmic tail, 1 | NM_013289 |
| KIR3DL2 | killer cell immunoglobulin-like receptor, three domains, long cytoplasmic tail, 2 | NM_006737 |
| KLRB1 | killer cell lectin-like receptor subfamily B, member 1 | NM_002258 |
| KRAS | v-Ki-ras2 Kirsten rat sarcoma viral oncogene homolog | NM_033360 |
| KYNU | kynureninase (L-kynurenine hydrolase) | NM_003937 |
| LAMB3 | laminin, beta 3 | NM_001017402 |
| LANCL1 | LanC lantibiotic synthetase component C-like 1 (bacterial) | NM_006055 |
| LAT | linker for activation of T cells | NM_014387 |
| LAT2 | linker for activation of T cells family, member 2 | NM_032464 |
| LAT2 | linker for activation of T cells family, member 2 | NM_032463 |
| LBH | limb bud and heart development homolog (mouse) | NM_030915 |
| LCK | lymphocyte-specific protein tyrosine kinase | NM_005356 |
| LGALS2 | lectin, galactoside-binding, soluble, 2 | NM_006498 |
| LHX1 | Homo sapiens LIM homeobox 1 (LHX1), mRNA | NM_005568 |
| LMAN1 | lectin, mannose-binding, 1 | NM_005570 |
| lnc-MYO10-1 | Homo sapiens cDNA FLJ43202 fis, clone FEBRA2008360. | AK125192 |
| LOC100130744 | Homo sapiens uncharacterized LOC100130744 (LOC100130744), long non-coding RNA | NR_046285 |
| LOC101927497 | Homo sapiens uncharacterized LOC101927497 (LOC101927497), transcript variant 1, long non-coding RNA | NR_110086 |
| LOC101927497 | Homo sapiens uncharacterized LOC101927497 (LOC101927497), transcript variant 1, long non-coding RNA | NR_110086 |
| LOC729860 | Homo sapiens cDNA FLJ41667 fis, clone FEBRA2028366. | AK123661 |
| LPHN3 | latrophilin 3 | NM_015236 |
| LPIN2 | lipin 2 | NM_014646 |
| LPP | LIM domain containing preferred translocation partner in lipoma | NM_005578 |
| LTA | lymphotoxin alpha (TNF superfamily, member 1) | NM_000595 |
| LTBP1 | latent transforming growth factor beta binding protein 1 | NM_206943 |
| LY6D | lymphocyte antigen 6 complex, locus D | NM_003695 |
| LYSMD2 | LysM, putative peptidoglycan-binding, domain containing 2 | NM_153374 |
| LZTS1 | leucine zipper, putative tumor suppressor 1 | NM_021020 |
| MAGEA9 | melanoma antigen family A, 9 | NM_005365 |
| MAGEB2 | melanoma antigen family B, 2 | NM_002364 |
| MARCH1 | membrane-associated ring finger (C3HC4) 1 | NM_017923 |
| MAT1A | methionine adenosyltransferase I, alpha | NM_000429 |
| MBD2 | methyl-CpG binding domain protein 2 | NM_003927 |
| MEI1 | Homo sapiens meiosis inhibitor 1 (MEI1), mRNA | NM_152513 |
| MEIS1 | Meis homeobox 1 | NM_002398 |
| MEOX1 | mesenchyme homeobox 1 | NM_004527 |
| MET | met proto-oncogene (hepatocyte growth factor receptor) | NM_000245 |

-continued

| Gene Symbol | Description | GenBank No. |
|---|---|---|
| METRNL | meteorin, glial cell differentiation regulator-like | NM_001004431 |
| MICALCL | MICAL C-terminal like | NM_032867 |
| MLLT3 | myeloid/lymphoid or mixed-lineage leukemia (trithorax homolog, Drosophila); translocated to, 3 | NM_004529 |
| MORC4 | Homo sapiens MORC family CW-type zinc finger 4 (MORC4), transcript variant 1, mRNA | NM_024657 |
| MPO | myeloperoxidase | NM_000250 |
| MREG | melanoregulin | NM_018000 |
| MRPL13 | mitochondrial ribosomal protein L13 | NM_014078 |
| MRPS12 | mitochondrial ribosomal protein S12 | NM_021107 |
| MTBP | Mdm2, transformed 3T3 cell double minute 2, p53 binding protein (mouse) binding protein, 104 kDa | NM_022045 |
| MYBPH | myosin binding protein H | NM_004997 |
| MYOM2 | Homo sapiens myomesin 2 (MYOM2), mRNA | NM_003970 |
| NAPG | N-ethylmaleimide-sensitive factor attachment protein, gamma | NM_003826 |
| NAPSA | napsin A aspartic peptidase | NM_004851 |
| NCOA7 | nuclear receptor coactivator 7 | NM_181782 |
| NCR1 | natural cytotoxicity triggering receptor 1 | NM_004829 |
| NCR3 | natural cytotoxicity triggering receptor 3 | NM_147130 |
| NFIX | nuclear factor I/X (CCAAT-binding transcription factor) | NM_002501 |
| NFKBIA | nuclear factor of kappa light polypeptide gene enhancer in B-cells inhibitor, alpha | NM_020529 |
| NKD2 | Homo sapiens naked cuticle homolog 2 (Drosophila) (NKD2), transcript variant 1, mRNA | NM_033120 |
| NMU | neuromedin U | NM_006681 |
| NPHP1 | nephronophthisis 1 (juvenile) | NM_000272 |
| NPY | Homo sapiens neuropeptide Y (NPY), mRNA | NM_000905 |
| NRXN3 | neurexin 3 | NM_004796 |
| NSMCE2 | non-SMC element 2, MMS21 homolog (S. cerevisiae) | NM_173685 |
| OASL | 2'-5'-oligoadenylate synthetase-like | NM_003733 |
| OSBPL5 | oxysterol binding protein-like 5 | NM_020896 |
| PASD1 | PAS domain containing 1 | NM_173493 |
| PBX4 | pre-B-cell leukemia homeobox 4 | NM_025245 |
| PCDH15 | protocadherin 15 | XM_373461 |
| PEX7 | Homo sapiens peroxisomal biogenesis factor 7 (PEX7), mRNA | NM_000288 |
| PFKM | Homo sapiens phosphofructokinase, muscle (PFKM), transcript variant 4, mRNA | NM_000289 |
| PICK1 | Homo sapiens protein interacting with PRKCA 1 (PICK1), transcript variant 1, mRNA | NM_012407 |
| PIF1 | PIF1 5'-to-3' DNA helicase homolog (S. cerevisiae) | NM_025049 |
| PIK3AP1 | phosphoinositide-3-kinase adaptor protein 1 | NM_152309 |
| PLAU | plasminogen activator, urokinase | NM_002658 |
| PLCG2 | phospholipase C, gamma 2 (phosphatidylinositol-specific) | NM_002661 |
| PLD3 | Homo sapiens phospholipase D family, member 3 (PLD3), transcript variant 2, mRNA | NM_012268 |
| PLEKHA5 | pleckstrin homology domain containing, family A member 5 | NM_019012 |
| PMAIP1 | phorbol-12-myristate-13-acetate-induced protein 1 | NM_021127 |
| POLK | polymerase (DNA directed) kappa | NM_016218 |
| POLR3G | Homo sapiens polymerase (RNA) III (DNA directed) polypeptide G (32 kD) (POLR3G), mRNA | NM_006467 |
| POLS | polymerase (DNA directed) sigma | NM_006999 |
| PPFIBP1 | PTPRF interacting protein, binding protein 1 (liprin beta 1) | NM_003622 |
| PPP1R3F | protein phosphatase 1, regulatory (inhibitor) subunit 3F | NM_033215 |
| PPP1R9A | protein phosphatase 1, regulatory (inhibitor) subunit 9A | NM_017650 |
| PPP2R2B | protein phosphatase 2 (formerly 2A), regulatory subunit B, beta isoform | NM_004576 |
| PRAM1 | Homo sapiens PML-RARA regulated adaptor molecule 1 (PRAM1), mRNA | NM_032152 |
| PRAME | preferentially expressed antigen in melanoma | NM_206956 |
| PRF1 | perforin 1 (pore forming protein) | NM_005041 |
| PRKCA | protein kinase C, alpha | NM_002737 |
| PRKCDBP | protein kinase C, delta binding protein | NM_145040 |

| Gene Symbol | Description | GenBank No. |
|---|---|---|
| PRKCE | *Homo sapiens* protein kinase C, epsilon (PRKCE), mRNA | NM_005400 |
| PRKCZ | *Homo sapiens* protein kinase C, zeta (PRKCZ), transcript variant 1, mRNA | NM_002744 |
| PRNP | prion protein (p27-30) (Creutzfeldt-Jakob disease, Gerstmann-Strausler-Scheinker syndrome, fatal familial insomnia) | NM_000311 |
| PSD3 | pleckstrin and Sec7 domain containing 3 | NM_015310 |
| PSTPIP1 | proline-serine-threonine phosphatase interacting protein 1 | NM_003978 |
| PTPN22 | protein tyrosine phosphatase, non-receptor type 22 (lymphoid) | NM_015967 |
| PTPN22 | protein tyrosine phosphatase, non-receptor type 22 (lymphoid), transcript variant 2 | NM_012411 |
| PTPRC | protein tyrosine phosphatase, receptor type, C | NM_002838 |
| PTPRE | protein tyrosine phosphatase, receptor type, E | NM_006504 |
| PVRIG | poliovirus receptor related immunoglobulin domain containing | NM_024070 |
| PYGB | phosphorylase, glycogen; brain | NM_002862 |
| RABGAP1L | RAB GTPase activating protein 1-like | NM_014857 |
| RAD21 | RAD21 homolog (*S. pombe*) | NM_006265 |
| RAGE | renal tumor antigen | NM_014226 |
| RALBP1 | ralA binding protein 1 | NM_006788 |
| RAMP1 | receptor (G protein-coupled) activity modifying protein 1 | NM_005855 |
| RARRES3 | retinoic acid receptor responder (tazarotene induced) 3 | NM_004585 |
| RBM38 | RNA binding motif protein 38 | NM_017495 |
| RDM1 | RAD52 motif 1 | NM_145654 |
| REEP2 | receptor accessory protein 2 | NM_016606 |
| REL | v-rel reticuloendotheliosis viral oncogene homolog (avian) | NM_002908 |
| RELB | v-rel reticuloendotheliosis viral oncogene homolog B, nuclear factor of kappa light polypeptide gene enhancer in B-cells 3 (avian) | NM_006509 |
| RFTN1 | raftlin, lipid raft linker 1 | NM_015150 |
| RGS3 | regulator of G-protein signalling 3 | NM_134427 |
| RGS9 | regulator of G-protein signalling 9 | NM_003835 |
| RHOV | ras homolog gene family, member V | NM_133639 |
| RIN1 | Ras and Rab interactor 1 | NM_004292 |
| RMRP | *Homo sapiens* RNA component of mitochondrial RNA processing endoribonuclease (RMRP), RNase MRP RNA | NR_003051 |
| RNASET2 | ribonuclease T2 | NM_003730 |
| RNF139 | ring finger protein 139 | NM_007218 |
| RNU2-1 | *Homo sapiens* RNA, U2 small nuclear 1 (RNU2-1), small nuclear RNA | NR_002716 |
| RPA4 | replication protein A4, 34 kDa | NM_013347 |
| RPS6KA2 | ribosomal protein S6 kinase, 90 kDa, polypeptide 2 | NM_021135 |
| RTP4 | receptor (chemosensory) transporter protein 4 | NM_022147 |
| S100A16 | S100 calcium binding protein A16 | NM_080388 |
| S100A4 | S100 calcium binding protein A4 | NM_002961 |
| S100P | S100 calcium binding protein P | NM_005980 |
| SAMSN1 | SAM domain, SH3 domain and nuclear localization signals 1 | NM_022136 |
| SCAMP5 | secretory carrier membrane protein 5 | NM_138967 |
| SCARNA2 | *Homo sapiens* small Cajal body-specific RNA 2 (SCARNA2), guide RNA | NR_003023 |
| SDC4 | syndecan 4 | NM_002999 |
| SEPT11 | *Homo sapiens* septin 11 (SEPT11), mRNA | NM_018243 |
| SERPINA9 | serpin peptidase inhibitor, clade A (alpha-1 antiproteinase, antitrypsin), member 9 | NM_175739 |
| SERPINB8 | serpin peptidase inhibitor, clade B (ovalbumin), member 8 | NM_198833 |
| SERPIND1 | serpin peptidase inhibitor, clade D (heparin cofactor), member 1 | NM_000185 |
| SETBP1 | SET binding protein 1 | NM_015559 |
| SH2D1B | SH2 domain containing 1B | NM_053282 |
| SH3BP5 | SH3-domain binding protein 5 (BTK-associated) | NM_004844 |
| SH3PXD2A | SH3 and PX domains 2A | NM_014631 |
| SIGLECP3 | sialic acid binding Ig-like lectin, pseudogene 3 | NR_002804 |
| SLA | Src-like-adaptor | NM_006748 |
| SLAMF1 | signaling lymphocytic activation molecule family member 1 | NM_003037 |

-continued

| Gene Symbol | Description | GenBank No. |
|---|---|---|
| SLC12A7 | solute carrier family 12 (potassium/chloride transporters), member 7 | NM_006598 |
| SLC16A10 | *Homo sapiens* solute carrier family 16 (aromatic amino acid transporter), member 10 (SLC16A10), mRNA | NM_018593 |
| SLC26A11 | solute carrier family 26, member 11 | NM_173626 |
| SLC2A14 | solute carrier family 2 (facilitated glucose transporter), member 14 | NM_153449 |
| SLC2A3 | solute carrier family 2 (facilitated glucose transporter), member 3 | NM_006931 |
| SLC41A2 | solute carrier family 41, member 2 | NM_032148 |
| SLC43A2 | solute carrier family 43, member 2 | NM_152346 |
| SLC45A3 | solute carrier family 45, member 3 | NM_033102 |
| SLC4A2 | *Homo sapiens* solute carrier family 4 (anion exchanger), member 2 (SLC4A2), transcript variant 1, mRNA | NM_003040 |
| SLCO2B1 | solute carrier organic anion transporter family, member 2B1 | NM_007256 |
| SMAD1 | SMAD family member 1 | NM_005900 |
| SMARCAD1 | SWI/SNF-related, matrix-associated actin-dependent regulator of chromatin, subfamily a, containing DEAD/H box 1 | NM_020159 |
| SMARCD3 | SWI/SNF related, matrix associated, actin dependent regulator of chromatin, subfamily d, member 3 | NM_003078 |
| SNHG5 | *Homo sapiens* small nucleolar RNA host gene 5 (non-protein coding) (SNHG5), long non-coding RNA | NR_003038 |
| SNORA73A | *Homo sapiens* small nucleolar RNA, H/ACA box 73A (SNORA73A), small nucleolar RNA | NR_002907 |
| SNORA73B | *Homo sapiens* small nucleolar RNA, H/ACA box 73B (SNORA73B), small nucleolar RNA | NR_004404 |
| SNORD3B-1 | *Homo sapiens* small nucleolar RNA, C/D box 3B-1 (SNORD3B-1), small nucleolar RNA | NR_003271 |
| SOX4 | SRY (sex determining region Y)-box 4 | NM_003107 |
| SPARCL1 | SPARC-like 1 (mast9, hevin) | NM_004684 |
| SPG7 | spastic paraplegia 7 (pure and complicated autosomal recessive) | NM_003119 |
| SQLE | squalene epoxidase | NM_003129 |
| SRF | *Homo sapiens* serum response factor (c-fos serum response element-binding transcription factor) (SRF), transcript variant 1, mRNA | NM_003131 |
| ST6GAL1 | ST6 beta-galactosamide alpha-2,6-sialyltranferase 1 | NM_173216 |
| STAT5A | signal transducer and activator of transcription 5A | NM_003152 |
| STAU2 | staufen, RNA binding protein, homolog 2 (*Drosophila*) | NM_014393 |
| STMN3 | stathmin-like 3 | NM_015894 |
| STMN4 | stathmin-like 4 | NM_030795 |
| SYNJ2BP | *Homo sapiens* synaptojanin 2 binding protein (SYNJ2BP), mRNA | NM_018373 |
| SYT17 | synaptotagmin XVII | NM_016524 |
| TAF2 | TAF2 RNA polymerase II, TATA box binding protein (TBP)-associated factor, 150 kDa | NM_003184 |
| TATDN1 | TatD DNase domain containing 1 | NM_032026 |
| TBL1X | *Homo sapiens* transducin (beta)-like 1X-linked (TBL1X), transcript variant 1, mRNA | NM_005647 |
| TBL1Y | *Homo sapiens* transducin (beta)-like 1, Y-linked (TBL1Y), transcript variant 1, mRNA | NM_033284 |
| TBX2 | T-box 2 | NM_005994 |
| TBXAS1 | thromboxane A synthase 1 (platelet, cytochrome P450, family 5, subfamily A) | NM_030984 |
| TEF | thyrotrophic embryonic factor | NM_003216 |
| TEKT5 | tektin 5 | NM_144674 |
| TESC | *Homo sapiens* tescalcin (TESC), transcript variant 1, mRNA | NM_017899 |
| TMEM121 | transmembrane protein 121 | NM_025268 |
| TMEM132A | *Homo sapiens* transmembrane protein 132A (TMEM132A), transcript variant 1, mRNA | NM_017870 |
| TMEM255A | *Homo sapiens* transmembrane protein 255A (TMEM255A), transcript variant 1, mRNA | NM_017938 |
| TMEM88 | transmembrane protein 88 | NM_203411 |
| TMTC2 | transmembrane and tetratricopeptide repeat containing 2 | NM_152588 |
| TNF | tumor necrosis factor (TNF superfamily, member 2) | NM_000594 |

| Gene Symbol | Description | GenBank No. |
|---|---|---|
| TNFRSF17 | tumor necrosis factor receptor superfamily, member 17 | NM_001192 |
| TNFRSF9 | tumor necrosis factor receptor superfamily, member 9 | NM_001561 |
| TNFSF4 | tumor necrosis factor (ligand) superfamily, member 4 (tax-transcriptionally activated glycoprotein 1, 34 kDa) | NM_003326 |
| TNN | Homo sapiens tenascin N (TNN), mRNA | NM_022093 |
| TNNI3 | troponin I type 3 (cardiac) | NM_000363 |
| TRAF1 | TNF receptor-associated factor 1 | NM_005658 |
| TRAM2 | translocation associated membrane protein 2 | NM_012288 |
| TRAα | T cell receptor alpha locus | |
| TREML2 | triggering receptor expressed on myeloid cells-like 2 | NM_024807 |
| TRIB1 | tribbles homolog 1 (Drosophila) | NM_025195 |
| TRIM34 | tripartite motif-containing 34 | NM_130390 |
| TRIM5 | tripartite motif-containing 5 | NM_033034 |
| TSPAN18 | tetraspanin 18 | NM_130783 |
| TSPAN32 | tetraspanin 32 | NM_139022 |
| TSPAN33 | tetraspanin 33 | NM_178562 |
| TXNDC10 | thioredoxin domain containing 10 | NM_019022 |
| TXNDC13 | thioredoxin domain containing 13 | NM_021156 |
| UBE1L | ubiquitin-activating enzyme E1-like | NM_003335 |
| UBE2E3 | ubiquitin-conjugating enzyme E2E 3 (UBC4/5 homolog, yeast) | NM_006357 |
| UBL4B | Homo sapiens ubiquitin-like 4B (UBL4B), mRNA | NM_203412 |
| VGLL3 | vestigial like 3 (Drosophila) | NM_016206 |
| VNN2 | vanin 2 | NM_004665 |
| VSIG9 | V-set and immunoglobulin domain containing 9 | NM_173799 |
| WASF3 | WAS protein family, member 3 | NM_006646 |
| WDR67 | WD repeat domain 67 | NM_145647 |
| WNT5A | wingless-type MMTV integration site family, member 5A | NM_003392 |
| ZBTB10 | zinc finger and BTB domain containing 10 | NM_023929 |
| ZBTB32 | zinc finger and BTB domain containing 32 | NM_014383 |
| ZDHHC11 | zinc finger, DHHC-type containing 11 | NM_024786 |
| ZHX1 | zinc fingers and homeoboxes 1 | NM_001017926 |
| ZNF425 | zinc finger protein 425 | NM_001001661 |
| ZNF572 | zinc finger protein 572 | NM_152412 |
| ZNF850 | Homo sapiens zinc finger protein 850 (ZNF850), transcript variant 1, mRNA | NM_001193552 |
| ZNF93 | Homo sapiens zinc finger protein 93 (ZNF93), mRNA | NM_031218 |

In some embodiments, the hematopoietic disorder is Acute Myeloid Leukemia (AML) and the hematopoietic disorder-associated molecule is one or more of:

| Gene Symbol | Description | GenBank No. |
|---|---|---|
| | ALU7_HUMAN (P39194) Alu subfamily SQ sequence contamination warning entry, partial (9%) | |
| | immunoglobulin kappa variable 1/OR2-108 (non-functional) [Source: HGNC Symbol; Acc: HGNC: 5767] | |
| | immunoglobulin kappa variable 1/OR9-2 (pseudogene) [Source: HGNC Symbol; Acc: HGNC: 49466] | |
| | Q5VT28_HUMAN (Q5VT28) Family with sequence similarity 27, member B (Family with sequence similarity 27, member A) (Family with sequence similarity 27, member C), partial (85%) | |
| | Synthetic construct Homo sapiens gateway clone IMAGE: 100021072 3' read RPS3A mRNA | CU688199 |
| ALPK3 | Homo sapiens alpha-kinase 3 (ALPK3), mRNA | NM_020778 |
| ARNTL | Homo sapiens aryl hydrocarbon receptor nuclear translocator-like (ARNTL), transcript variant 3, mRNA | NM_001030273 |

-continued

| Gene Symbol | Description | GenBank No. |
|---|---|---|
| BARX1 | *Homo sapiens* BARX homeobox 1 (BARX1), mRNA | NM_021570 |
| C11orf74 | *Homo sapiens* chromosome 11 open reading frame 74 (C11orf74), transcript variant 4, mRNA | NM_138787 |
| C16orf45 | *Homo sapiens* chromosome 16 open reading frame 45 (C16orf45), transcript variant 1, mRNA | NM_033201 |
| C8orf88 | *Homo sapiens* chromosome 8 open reading frame 88 (C8orf88), mRNA | NM_001190972 |
| CCDC3 | *Homo sapiens* coiled-coil domain containing 3 (CCDC3), transcript variant 1, mRNA | NM_031455 |
| CD93 | *Homo sapiens* CD93 molecule (CD93), mRNA | NM_012072 |
| CDC42EP1 | *Homo sapiens* CDC42 effector protein (Rho GTPase binding) 1 (CDC42EP1), mRNA | NM_152243 |
| CDC42EP3 | *Homo sapiens* CDC42 effector protein (Rho GTPase binding) 3 (CDC42EP3), transcript variant 1, mRNA | NM_006449 |
| CDKN2C | *Homo sapiens* cyclin-dependent kinase inhibitor 2C (p18, inhibits CDK4) (CDKN2C), transcript variant 2, mRNA | NM_078626 |
| COL15A1 | *Homo sapiens* collagen, type XV, alpha 1 (COL15A1), mRNA | NM_001855 |
| COL6A2 | *Homo sapiens* collagen, type VI, alpha 2 (COL6A2), transcript variant 2C2a, mRNA | NM_058174 |
| DUSP5P1 | *Homo sapiens* dual specificity phosphatase 5 pseudogene 1 (DUSP5P1), non-coding RNA | NR_002834 |
| EXO5 | *Homo sapiens* exonuclease 5 (EXO5), mRNA | NM_022774 |
| FAT1 | *Homo sapiens* FAT atypical cadherin 1 (FAT1), mRNA | NM_005245 |
| FOXK1 | *Homo sapiens* forkhead box K1 (FOXK1), mRNA | NM_001037165 |
| GATA2-AS1 | *Homo sapiens* cDNA: FLJ21000 fis, clone CAE03359. | AK024653 |
| GIMAP1 | *Homo sapiens* GTPase, IMAP family member 1 (GIMAP1), mRNA | NM_130759 |
| GPR179 | *Homo sapiens* G protein-coupled receptor 179 (GPR179), mRNA | NM_001004334 |
| HSH2D | *Homo sapiens* hematopoietic SH2 domain containing (HSH2D), transcript variant 1, mRNA | NM_032855 |
| IL17RC | *Homo sapiens* interleukin 17 receptor C (IL17RC), transcript variant 2, mRNA | NM_153461 |
| KCNN4 | *Homo sapiens* potassium channel, calcium activated intermediate/small conductance subfamily N alpha, member 4 (KCNN4), mRNA | NM_002250 |
| KCNQ5-IT1 | *Homo sapiens* KCNQ5 intronic transcript 1 (non-protein coding) (KCNQ5-IT1), long non-coding RNA | NR_120503 |
| LHX1 | *Homo sapiens* LIM homeobox 1 (LHX1), mRNA | NM_005568 |
| lnc-MYO10-1 | *Homo sapiens* cDNA FLJ43202 fis, clone FEBRA2008360. | AK125192 |
| LOC100130744 | *Homo sapiens* uncharacterized LOC100130744 (LOC100130744), long non-coding RNA | NR_046285 |
| LOC101927497 | *Homo sapiens* uncharacterized LOC101927497 (LOC101927497), transcript variant 1, long non-coding RNA | NR_110086 |
| LOC101927497 | *Homo sapiens* uncharacterized LOC101927497 (LOC101927497), transcript variant 1, long non-coding RNA | NR_110086 |
| LOC729860 | *Homo sapiens* cDNA FLJ41667 fis, clone FEBRA2028366. | AK123661 |
| MEI1 | *Homo sapiens* meiosis inhibitor 1 (MEI1), mRNA | NM_152513 |
| MORC4 | *Homo sapiens* MORC family CW-type zinc finger 4 (MORC4), transcript variant 1, mRNA | NM_024657 |
| MYOM2 | *Homo sapiens* myomesin 2 (MYOM2), mRNA | NM_003970 |
| NKD2 | *Homo sapiens* naked cuticle homolog 2 (*Drosophila*) (NKD2), transcript variant 1, mRNA | NM_033120 |
| NPY | *Homo sapiens* neuropeptide Y (NPY), mRNA | NM_000905 |
| PEX7 | *Homo sapiens* peroxisomal biogenesis factor 7 (PEX7), mRNA | NM_000288 |

| Gene Symbol | Description | GenBank No. |
| --- | --- | --- |
| PFKM | Homo sapiens phosphofructokinase, muscle (PFKM), transcript variant 4, mRNA | NM_000289 |
| PICK1 | Homo sapiens protein interacting with PRKCA 1 (PICK1), transcript variant 1, mRNA | NM_012407 |
| PLD3 | Homo sapiens phospholipase D family, member 3 (PLD3), transcript variant 2, mRNA | NM_012268 |
| POLR3G | Homo sapiens polymerase (RNA) III (DNA directed) polypeptide G (32 kD) (POLR3G), mRNA | NM_006467 |
| PRAM1 | Homo sapiens PML-RARA regulated adaptor molecule 1 (PRAM1), mRNA | NM_032152 |
| PRKCE | Homo sapiens protein kinase C, epsilon (PRKCE), mRNA | NM_005400 |
| PRKCZ | Homo sapiens protein kinase C, zeta (PRKCZ), transcript variant 1, mRNA | NM_002744 |
| RMRP | Homo sapiens RNA component of mitochondrial RNA processing endoribonuclease (RMRP), RNase MRP RNA | NR_003051 |
| RNU2-1 | Homo sapiens RNA, U2 small nuclear 1 (RNU2-1), small nuclear RNA | NR_002716 |
| SCARNA2 | Homo sapiens small Cajal body-specific RNA 2 (SCARNA2), guide RNA | NR_003023 |
| SEPT11 | Homo sapiens septin 11 (SEPT11), mRNA | NM_018243 |
| SLC16A10 | Homo sapiens solute carrier family 16 (aromatic amino acid transporter), member 10 (SLC16A10), mRNA | NM_018593 |
| SLC4A2 | Homo sapiens solute carrier family 4 (anion exchanger), member 2 (SLC4A2), transcript variant 1, mRNA | NM_003040 |
| SNHG5 | Homo sapiens small nucleolar RNA host gene 5 (non-protein coding) (SNHG5), long non-coding RNA | NR_003038 |
| SNORA73A | Homo sapiens small nucleolar RNA, H/ACA box 73A (SNORA73A), small nucleolar RNA | NR_002907 |
| SNORA73B | Homo sapiens small nucleolar RNA, H/ACA box 73B (SNORA73B), small nucleolar RNA | NR_004404 |
| SNORD3B-1 | Homo sapiens small nucleolar RNA, C/D box 3B-1 (SNORD3B-1), small nucleolar RNA | NR_003271 |
| SRF | Homo sapiens serum response factor (c-fos serum response element-binding transcription factor) (SRF), transcript variant 1, mRNA | NM_003131 |
| SYNJ2BP | Homo sapiens synaptojanin 2 binding protein (SYNJ2BP), mRNA | NM_018373 |
| TBL1X | Homo sapiens transducin (beta)-like 1X-linked (TBL1X), transcript variant 1, mRNA | NM_005647 |
| TBL1Y | Homo sapiens transducin (beta)-like 1, Y-linked (TBL1Y), transcript variant 1, mRNA | NM_033284 |
| TESC | Homo sapiens tescalcin (TESC), transcript variant 1, mRNA | NM_017899 |
| TMEM132A | Homo sapiens transmembrane protein 132A (TMEM132A), transcript variant 1, mRNA | NM_017870 |
| TMEM255A | Homo sapiens transmembrane protein 255A (TMEM255A), transcript variant 1, mRNA | NM_017938 |
| TNN | Homo sapiens tenascin N (TNN), mRNA | NM_022093 |
| UBL4B | Homo sapiens ubiquitin-like 4B (UBL4B), mRNA | NM_203412 |
| ZNF850 | Homo sapiens zinc finger protein 850 (ZNF850), transcript variant 1, mRNA | NM_001193552 |
| ZNF93 | Homo sapiens zinc finger protein 93 (ZNF93), mRNA | NM_031218 |

In some embodiments, the hematopoietic disorder-associated molecule in AML is tescalcin (TESC), CD93, KCNN4, SLC4A2, or CDC42EP1.

In some embodiments, the hematopoietic disorder is Hairy Cell Leukemia (HCL) and the hematopoietic disorder-associated molecule is one or more of:

| Gene Symbol | Description | GenBank No. |
| --- | --- | --- |
| | ALU2_HUMAN (P39189) Alu subfamily SB sequence contamination warning entry, partial (5%) [THC2302062] | XM_370835 |
| | BIC transcript | NR_001458 |
| | Carboxypeptidase, vitellogenic-like | |

| Gene Symbol | Description | GenBank No. |
|---|---|---|
| | caspase-1 dominant-negative inhibitor pseudo-ICE | NM_001017534 |
| | CBF1 interacting corepressor | NM_004882 |
| | CDNA FLJ30652 fis, clone DFNES2000011 | |
| | CDNA: FLJ23228 fis, clone CAE06654 | |
| | Clone FBA1 Cri-du-chat region mRNA | |
| | defective in sister chromatid cohesion homolog 1 (*S. cerevisiae*) | NM_024094 |
| | Ecotropic viral integration site 5 | |
| | *H. sapiens* rearranged VDJ region (BEL14). [X81724] | XM_370973 |
| | *H. sapiens* TAFII105 mRNA, partial. [Y09321] | XM_290809 |
| | *Homo sapiens* adaptor-related protein complex 1, sigma 3 subunit (AP1S3), mRNA [NM_178814] | NM_178814 |
| | *Homo sapiens* androgen-induced proliferation inhibitor (APRIN), transcript variant 2, mRNA [NM_015928] | NM_015928 |
| | *Homo sapiens* cDNA FLJ31247 fis, clone KIDNE2005296, weakly similar to ACTIN, CYTOPLASMIC 1. [AK055809] | |
| | *Homo sapiens* cDNA FLJ31859 fis, clone NT2RP7001231. [AK056421] | |
| | *Homo sapiens* chromosome 20 open reading frame 35 (C20orf35), mRNA [NM_018478] | NM_018478 |
| | *Homo sapiens* Fc receptor-like 2 (FCRL2), mRNA [NM_138739] | NM_138739 |
| | *Homo sapiens* Fc receptor-like and mucin-like 2 (FCRLM2), mRNA [NM_152378] | NM_152378 |
| | *Homo sapiens* HSPC053 mRNA, complete cds. [AF161538] | |
| | *Homo sapiens* hypothetical protein LOC90925 (LOC90925), mRNA [NM_175870] | NM_175870 |
| | *Homo sapiens* mRNA for KIAA1023 protein, partial cds. [AB028946] | |
| | *Homo sapiens* mRNA for KIAA1162 protein, partial cds. [AB032988] | |
| | *Homo sapiens* PHD finger protein 2 (PHF2), transcript variant 2, mRNA [NM_024517] | NM_024517 |
| | *Homo sapiens*, clone IMAGE: 4285740, mRNA. [BC006008] | XM_113962 |
| | *Homo sapiens*, clone IMAGE: 4445372, mRNA | |
| | human full-length cDNA clone CS0DL004YM19 of B cells (Ramos cell line) of *Homo sapiens* (human). [BX248300] | |
| | hypothetical gene supported by AK124333 | XM_379648 |
| | Hypothetical gene supported by AK128882 | XM_499014 |
| | hypothetical protein FLJ20186 | NM_017702 |
| | hypothetical protein FLJ22814 | |
| | hypothetical protein LOC134145 | NM_199133 |
| | hypothetical protein LOC283454 | |
| | hypothetical protein LOC643401 | |
| | Immunoglobulin heavy constant gamma 1 (G1m marker) | |
| | LSM14B, SCD6 homolog B (*S. cerevisiae*) | |
| | macrophage expressed gene 1 | XM_166227 |
| | MEX3A protein | XM_044166 |
| | NOA1_HUMAN (Q9NY12) Nucleolar protein family A member 1 (snoRNP protein GAR1) (H/ACA ribonucleoprotein GAR1), partial (18%) [THC2314822] | |
| | plasma glutamate carboxypeptidase | NM_016134 |
| | PREDICTED: *Homo sapiens* similar to Ig heavy chain V-III region VH26 precursor (LOC390714), mRNA [XM_372632] | XM_372632 |
| | Q69Z36 (Q69Z36) MKIAA2009 protein (Fragment), partial (8%) [THC2430293] | |
| | Q7Z5X4 (Q7Z5X4) Intermediate filament-like protein MGC: 2625, isoform 1, partial (12%) [THC2301370] | |
| | Q7ZX66 (Q7ZX66) RNPC7 protein (Fragment), partial (9%) [THC2309960] | |
| | Q9BYX7 (Q9BYX7) FKSG30, partial (41%) [THC2364880] | |
| | Q9F8M7 (Q9F8M7) DTDP-glucose 4,6-dehydratase (Fragment), partial (11%) [THC2406944] | |

| Gene Symbol | Description | GenBank No. |
|---|---|---|
| | Q9H1B6 (Q9H1B6) Xylosyltransferase I (Fragment), partial (8%) [THC2341118] telomerase reverse transcriptase; synonyms: TP2, TRT, EST2, TCS1, hEST2; isoform 1 is encoded by transcript variant 1; telomerase catalytic subunit; *Homo sapiens* telomerase reverse transcriptase (TERT), transcript variant 1, mRNA. | NM_003219 |
| | Expressed Sequence Tag (EST) | BM819787 |
| | Expressed Sequence Tag (EST) | BG112935 |
| | Expressed Sequence Tag (EST) | BQ049338 |
| | UB30_HUMAN (Q70CQ3) Ubiquitin carboxyl-terminal hydrolase 30 (Ubiquitin thiolesterase 30) (Ubiquitin-specific processing protease 30) (Deubiquitinating enzyme 30), partial (4%) [THC2311946] | |
| | Zinc finger protein 718 | |
| ABCA1 | ATP-binding cassette, sub-family A (ABC1), member 1 | NM_005502 |
| ACTG1 | actin, gamma 1 | NM_001614 |
| ACTG2 | actin, gamma 2, smooth muscle, enteric | NM_001615 |
| AEBP2 | AE binding protein 2 | NM_153207 |
| AICDA | activation-induced cytidine deaminase | NM_020661 |
| ANKRD25 | ankyrin repeat domain 25 | NM_015493 |
| APOL3 | apolipoprotein L, 3 | NM_145641 |
| ATAD2 | ATPase family, AAA domain containing 2 | NM_014109 |
| ATP10D | ATPase, Class V, type 10D | NM_020453 |
| BACE2 | beta-site APP-cleaving enzyme 2 | NM_012105 |
| BANK1 | B-cell scaffold protein with ankyrin repeats 1 | NM_017935 |
| BCAS3 | breast carcinoma amplified sequence 3 | NM_017679 |
| BCHE | butyrylcholinesterase | NM_000055 |
| BCL2A1 | BCL2-related protein A1 | NM_004049 |
| BMF | Bcl2 modifying factor | NM_001003940 |
| BMP7 | bone morphogenetic protein 7 (osteogenic protein 1) | NM_001719 |
| BRDG1; STAP1 | BCR downstream signaling 1 | NM_012108 |
| C11orf41 | chromosome 11 open reading frame 41 | XM_039515 |
| C18orf10 | chromosome 18 open reading frame 10 | NM_015476 |
| C19orf51 | chromosome 19 open reading frame 51 | NM_178837 |
| C1orf38 | chromosome 1 open reading frame 38 | NM_004848 |
| C1orf54 | chromosome 1 open reading frame 54 | NM_024579 |
| C20orf67 | chromosome 20 open reading frame 67 | NM_022104 |
| C21orf34 | chromosome 21 open reading frame 34, transcript variant 1 | NM_001005732 |
| C21orf34 | chromosome 21 open reading frame 34, transcript variant 2 | NM_001005733 |
| CARD6 | caspase recruitment domain family, member 6 | NM_032587 |
| CASP1 | caspase 1, apoptosis-related cysteine peptidase (interleukin 1, beta, convertase) | NM_033292 |
| CASP4 | caspase 4, apoptosis-related cysteine peptidase | NM_033306 |
| CASP5 | caspase 5, apoptosis-related cysteine peptidase | NM_004347 |
| CCL3 | chemokine (C-C motif) ligand 3 | NM_002983 |
| CCL3L3 | chemokine (C-C motif) ligand 3-like 3 | NM_001001437 |
| CCL4 | chemokine (C-C motif) ligand 4 | NM_002984 |
| CCL5 | chemokine (C-C motif) ligand 5 | NM_002985 |
| CD22 | CD22 molecule | NM_001771 |
| CD38 | CD38 molecule | NM_001775 |
| CEACAM1 | carcinoembryonic antigen-related cell adhesion molecule 1 (biliary glycoprotein) | NM_001712 |
| CEBPB | CCAAT/enhancer binding protein (C/EBP), beta | NM_005194 |
| CLCN2 | chloride channel 2 | NM_004366 |
| CR2 | complement component (3d/Epstein Barr virus) receptor 2 | NM_001006658 |
| CSF1R | colony stimulating factor 1 receptor, formerly McDonough feline sarcoma viral (v-fms) oncogene homolog | NM_005211 |
| CSTA | cystatin A (stefin A) | NM_005213 |
| CTSS | cathepsin S | NM_004079 |
| CUTL2 | cut-like 2 (*Drosophila*) | NM_015267 |
| CX3CR1 | chemokine (C-X3-C motif) receptor 1 | NM_001337 |
| CYP2U1 | cytochrome P450, family 2, subfamily U, polypeptide 1 | NM_183075 |
| DEFB123 | defensin, beta 123 | NM_153324 |
| DERL1 | Der1-like domain family, member 1 | NM_024295 |
| DLGAP4 | discs, large (*Drosophila*) homolog-associated protein 4 | NM_014902 |

| Gene Symbol | Description | GenBank No. |
|---|---|---|
| DNMT3B | DNA (cytosine-5-)-methyltransferase 3 beta | NM_175850 |
| DOCK10 | dedicator of cytokinesis 10 | NM_014689 |
| DSTN | destrin (actin depolymerizing factor) | NM_001011546 |
| EIF3S3 | eukaryotic translation initiation factor 3, subunit 3 gamma, 40 kDa | NM_003756 |
| EMP3 | epithelial membrane protein 3 | NM_001425 |
| EVL | Enah/Vasp-like | NM_016337 |
| FAM129C | family with sequence similarity 129, member C | NM_173544 |
| FAM59A | family with sequence similarity 59, member A | NM_022751 |
| FBLN5 | fibulin 5 | NM_006329 |
| FCER2 | Fc fragment of IgE, low affinity II, receptor for (CD23) | NM_002002 |
| FCN1 | ficolin (collagen/fibrinogen domain containing) 1 | NM_002003 |
| FCRL2 | Fc receptor-like 2 | NM_138738 |
| FCRL3 | Fc receptor-like 3 | NM_052939 |
| FGF18 | fibroblast growth factor 18 | NM_003862 |
| FHOD3 | formin homology 2 domain containing 3 | NM_025135 |
| FSD1 | fibronectin type III and SPRY domain containing 1 | NM_024333 |
| GAS7 | growth arrest-specific 7 | NM_201433 |
| GBP1 | guanylate binding protein 1, interferon-inducible, 67 kDa | NM_002053 |
| GCA | grancalcin, EF-hand calcium binding protein | NM_012198 |
| GDF15 | growth differentiation factor 15 | NM_004864 |
| GLI1 | glioma-associated oncogene homolog 1 (zinc finger protein) | NM_005269 |
| GM2A | GM2 ganglioside activator | NM_000405 |
| GPNMB | glycoprotein (transmembrane) nmb | NM_001005340 |
| GPR109B | G protein-coupled receptor 109B | NM_006018 |
| GPR30 | G protein-coupled receptor 30 | NM_001505 |
| GRIN2C | glutamate receptor, ionotropic, N-methyl D-aspartate 2C | NM_000835 |
| GRN | granulin | NM_002087 |
| HES6 | hairy and enhancer of split 6 (*Drosophila*) | NM_018645 |
| HHAT | hedgehog acyltransferase | NM_018194 |
| HIST1H2BK | histone cluster 1, H2bk | NM_080593 |
| HM13 | histocompatibility (minor) 13 | NM_178582 |
| HRASLS2 | HRAS-like suppressor 2 | NM_017878 |
| HRK | harakiri, BCL2 interacting protein (contains only BH3 domain) | NM_003806 |
| HSPA4 | Heat shock 70 kDa protein 4 | |
| HSPA6 | heat shock 70 kDa protein 6 (HSP70B') | NM_002155 |
| IFI35 | interferon-induced protein 35 | NM_005533 |
| IGF1R | insulin-like growth factor 1 receptor | |
| IGHV1-69 | immunoglobulin heavy variable 1-69 | |
| IGJ | immunoglobulin J polypeptide, linker protein for immunoglobulin alpha and mu polypeptides | NM_144646 |
| IL1R2 | interleukin 1 receptor, type II | NM_004633 |
| IL3RA | interleukin 3 receptor, alpha (low affinity) | NM_002183 |
| IL7R | interleukin 7 receptor | NM_002185 |
| INPP4B | inositol polyphosphate-4-phosphatase, type II, 105 kDa | NM_003866 |
| ITGAX | integrin, alpha X (complement component 3 receptor 4 subunit) | NM_000887 |
| ITGB7 | integrin, beta 7 | NM_000889 |
| JUP | junction plakoglobin | NM_002230 |
| KATNAL2 | katanin p60 subunit A-like 2 | NM_031303 |
| KCNMA1 | potassium large conductance calcium-activated channel, subfamily M, alpha member 1 | NM_002247 |
| KIAA0196 | KIAA0196 | NM_014846 |
| KRAS | v-Ki-ras2 Kirsten rat sarcoma viral oncogene homolog | NM_033360 |
| KYNU | kynureninase (L-kynurenine hydrolase) | NM_003937 |
| LANCL1 | LanC lantibiotic synthetase component C-like 1 (bacterial) | NM_006055 |
| LCK | lymphocyte-specific protein tyrosine kinase | NM_005356 |
| LGALS2 | lectin, galactoside-binding, soluble, 2 | NM_006498 |
| LMAN1 | lectin, mannose-binding, 1 | NM_005570 |
| LPIN2 | lipin 2 | NM_014646 |
| LPP | LIM domain containing preferred translocation partner in lipoma | NM_005578 |
| LYSMD2 | LysM, putative peptidoglycan-binding, domain containing 2 | NM_153374 |
| MARCH1 | membrane-associated ring finger (C3HC4) 1 | NM_017923 |
| MAT1A | methionine adenosyltransferase I, alpha | NM_000429 |
| MBD2 | methyl-CpG binding domain protein 2 | NM_003927 |
| MEIS1 | Meis homeobox 1 | NM_002398 |

-continued

| Gene Symbol | Description | GenBank No. |
|---|---|---|
| MET | met proto-oncogene (hepatocyte growth factor receptor) | NM_000245 |
| METRNL | meteorin, glial cell differentiation regulator-like | NM_001004431 |
| MREG | melanoregulin | NM_018000 |
| MRPL13 | mitochondrial ribosomal protein L13 | NM_014078 |
| MTBP | Mdm2, transformed 3T3 cell double minute 2, p53 binding protein (mouse) binding protein, 104 kDa | NM_022045 |
| MYBPH | myosin binding protein H | NM_004997 |
| NAPG | N-ethylmaleimide-sensitive factor attachment protein, gamma | NM_003826 |
| NMU | neuromedin U | NM_006681 |
| NRXN3 | neurexin 3 | NM_004796 |
| NSMCE2 | non-SMC element 2, MMS21 homolog (S. cerevisiae) | NM_173685 |
| PBX4 | pre-B-cell leukemia homeobox 4 | NM_025245 |
| PIF1 | PIF1 5'-to-3' DNA helicase homolog (S. cerevisiae) | NM_025049 |
| PIK3AP1 | phosphoinositide-3-kinase adaptor protein 1 | NM_152309 |
| PLEKHA5 | pleckstrin homology domain containing, family A member 5 | NM_019012 |
| PMAIP1 | phorbol-12-myristate-13-acetate-induced protein 1 | NM_021127 |
| POLK | polymerase (DNA directed) kappa | NM_016218 |
| POLS | polymerase (DNA directed) sigma | NM_006999 |
| PPP1R9A | protein phosphatase 1, regulatory (inhibitor) subunit 9A | NM_017650 |
| PRAME | preferentially expressed antigen in melanoma | NM_206956 |
| PRKCA | protein kinase C, alpha | NM_002737 |
| PRNP | prion protein (p27-30) (Creutzfeldt-Jakob disease, Gerstmann-Strausler-Scheinker syndrome, fatal familial insomnia) | NM_000311 |
| PSD3 | pleckstrin and Sec7 domain containing 3 | NM_015310 |
| PSTPIP1 | proline-serine-threonine phosphatase interacting protein 1 | NM_003978 |
| PTPN22 | protein tyrosine phosphatase, non-receptor type 22 (lymphoid), transcript variant 1 | NM_015967 |
| PTPN22 | protein tyrosine phosphatase, non-receptor type 22 (lymphoid), transcript variant 2 | NM_012411 |
| PTPRE | protein tyrosine phosphatase, receptor type, E | NM_006504 |
| PYGB | phosphorylase, glycogen; brain | NM_002862 |
| RABGAP1L | RAB GTPase activating protein 1-like | NM_014857 |
| RAD21 | RAD21 homolog (S. pombe) | NM_006265 |
| RALBP1 | ralA binding protein 1 | NM_006788 |
| RAMP1 | receptor (G protein-coupled) activity modifying protein 1 | NM_005855 |
| RARRES3 | retinoic acid receptor responder (tazarotene induced) 3 | NM_004585 |
| RBM38 | RNA binding motif protein 38 | NM_017495 |
| RFTN1 | raftlin, lipid raft linker 1 | NM_015150 |
| RGS9 | regulator of G-protein signalling 9 | NM_003835 |
| RNF139 | ring finger protein 139 | NM_007218 |
| RPS6KA2 | ribosomal protein S6 kinase, 90 kDa, polypeptide 2 | NM_021135 |
| RTP4 | receptor (chemosensory) transporter protein 4 | NM_022147 |
| SAMSN1 | SAM domain, SH3 domain and nuclear localization signals 1 | NM_022136 |
| SCAMP5 | secretory carrier membrane protein 5 | NM_138967 |
| SERPINA9 | serpin peptidase inhibitor, clade A (alpha-1 antiproteinase, antitrypsin), member 9 | NM_175739 |
| SERPINB8 | serpin peptidase inhibitor, clade B (ovalbumin), member 8 | NM_198833 |
| SETBP1 | SET binding protein 1 | NM_015559 |
| SH3BP5 | SH3-domain binding protein 5 (BTK-associated) | NM_004844 |
| SIGLECP3 | sialic acid binding Ig-like lectin, pseudogene 3 | NR_002804 |
| SLAMF1 | signaling lymphocytic activation molecule family member 1 | NM_003037 |
| SLC26A11 | solute carrier family 26, member 11 | NM_173626 |
| SLC45A3 | solute carrier family 45, member 3 | NM_033102 |
| SLCO2B1 | solute carrier organic anion transporter family, member 2B1 | NM_007256 |
| SMAD1 | SMAD family member 1 | NM_005900 |
| SMARCAD1 | SWI/SNF-related, matrix-associated actin-dependent regulator of chromatin, subfamily a, containing DEAD/H box 1 | NM_020159 |
| SMARCD3 | SWI/SNF related, matrix associated, actin dependent regulator of chromatin, subfamily d, member 3 | NM_003078 |
| SOX4 | SRY (sex determining region Y)-box 4 | |
| SPARCL1 | SPARC-like 1 (mast9, hevin) | NM_004684 |

-continued

| Gene Symbol | Description | GenBank No. |
|---|---|---|
| SQLE | squalene epoxidase | NM_003129 |
| ST6GAL1 | ST6 beta-galactosamide alpha-2,6-sialyltranferase 1 | NM_173216 |
| STAU2 | staufen, RNA binding protein, homolog 2 (*Drosophila*) | NM_014393 |
| SYT17 | synaptotagmin XVII | NM_016524 |
| TAF2 | TAF2 RNA polymerase II, TATA box binding protein (TBP)-associated factor, 150 kDa | NM_003184 |
| TATDN1 | TatD DNase domain containing 1 | NM_032026 |
| TBXAS1 | thromboxane A synthase 1 (platelet, cytochrome P450, family 5, subfamily A) | NM_030984 |
| TEKT5 | tektin 5 | NM_144674 |
| TMEM121 | transmembrane protein 121 | NM_025268 |
| TNFRSF17 | tumor necrosis factor receptor superfamily, member 17 | NM_001192 |
| TNNI3 | troponin I type 3 (cardiac) | NM_000363 |
| TRAM2 | translocation associated membrane protein 2 | NM_012288 |
| TREML2 | triggering receptor expressed on myeloid cells-like 2 | NM_024807 |
| TRIB1 | tribbles homolog 1 (*Drosophila*) | NM_025195 |
| TRIM34 | tripartite motif-containing 34 | NM_130390 |
| TRIM5 | tripartite motif-containing 5 | NM_033034 |
| TSPAN33 | tetraspanin 33 | NM_178562 |
| TXNDC10 | thioredoxin domain containing 10 | NM_019022 |
| TXNDC13 | thioredoxin domain containing 13 | NM_021156 |
| UBE1L | ubiquitin-activating enzyme E1-like | NM_003335 |
| UBE2E3 | ubiquitin-conjugating enzyme E2E 3 (UBC4/5 homolog, yeast) | NM_006357 |
| WASF3 | WAS protein family, member 3 | NM_006646 |
| WDR67 | WD repeat domain 67 | NM_145647 |
| WNT5A | wingless-type MMTV integration site family, member 5A | NM_003392 |
| ZBTB32 | zinc finger and BTB domain containing 32 | NM_014383 |
| ZHX1 | zinc fingers and homeoboxes 1 | NM_001017926 |
| ZNF572 | zinc finger protein 572 | NM_152412 |

In some embodiments, the hematopoietic disorder-associated molecule in HCL is CD21, CD121b, CD150, CSF1R, GPR30, ITGB7, FCRL2, FCRL3 or CD22.

In some embodiments, the hematopoietic disorder is adult T-cell leukemia/lymphoma (ATLL) and the hematopoietic disorder-associated molecule is one or more of:

| Gene Symbol | Description | GenBank No. |
|---|---|---|
| | Clone pp6455 unknown mRNA | |
| | *Homo sapiens* aspartyl protease 3 mRNA, partial cds. [AF200344] | XR_000169 |
| | KIAA1706 protein | NM_030636 |
| | *Homo sapiens* cDNA FLJ38080 fis, clone CTONG2016185. [AK095399] | |
| | FLJ35767 protein | NM_207459 |
| | Similar to ATP-binding cassette, sub-family A (ABC1), member 17 | XM_498629 |
| | *Homo sapiens* Fc receptor-like and mucin-like 2 (FCRLM2), mRNA [NM_152378] | NM_152378 |
| | *Homo sapiens* chordin (CHRD), transcript variant 2, mRNA [NM_177978] | NM_177978 |
| | *Homo sapiens*, Similar to snail homolog 3 (*Drosophila*), clone IMAGE: 5209145, mRNA, partial cds. [BC041461] | XM_370995 |
| | KIAA1666 protein | XM_036936 |
| | *Homo sapiens* chromosome 6 open reading frame 54 (C6orf54), mRNA [NM_014354] | NM_014354 |
| | Human mRNA for T-cell receptor V beta gene segment V-beta-13, clone IGRb14. [X58809] | |
| | apolipoprotein B48 receptor; *Homo sapiens* apolipoprotein B48 receptor (APOB48R), mRNA. | NM_182804 |
| | similar to common salivary protein 1 | NM_145252 |
| | phospholysine phosphohistidine inorganic pyrophosphate phosphatase | NM_022126 |
| | *Homo sapiens* cDNA FLJ27224 fis, clone SYN04819. [AK130734] | |
| | extracellular active factor; neuronal death blocker of Alzheimer's disease insults; *Homo sapiens* Humanin (HN1) mRNA, complete cds. | |
| | full-length cDNA clone CS0DL009YB17 of B cells | |

| Gene Symbol | Description | GenBank No. |
|---|---|---|
| | (Ramos cell line) Cot 25-normalized of *Homo sapiens* (human). [CR593568] | |
| | O13102 (O13102) Activin type IIB receptor precursor, partial (5%) [THC2372182] | |
| | FABE_HUMAN (Q01469) Fatty acid-binding protein, epidermal (E-FABP) (Psoriasis-associated fatty acid-binding protein homolog) (PA-FABP), partial (53%) [THC2302865] | |
| | Transcribed locus | |
| | *Homo sapiens* zinc finger homeobox 2 (ZFHX2), mRNA [NM_033400] | NM_033400 |
| | trophoblast-derived noncoding RNA | NR_002802 |
| | predicted protein of HQ1995; *Homo sapiens* PRO1995 mRNA, complete cds. | |
| | hypothetical protein MGC14376 | NM_032895 |
| | BIC transcript | NR_001458 |
| | yy53b06.r1 Soares_multiple_sclerosis_2NbHMSP *Homo sapiens* cDNA clone IMAGE: 277235 5', mRNA sequence. | |
| | CDNA FLJ37310 fis, clone BRAMY2016706 | |
| | C40201 artifact-warning sequence (translated ALU class C) - human {*Homo sapiens*;}, partial (11%) [THC2317149] | |
| | Q6DD14 (Q6DD14) MGC80451 protein, partial (40%) [THC2340803] | |
| | *Homo sapiens* CSAG family, member 4 (CSAG4), mRNA [NM_001025306] | NM_001025306 |
| | ALU5_HUMAN (P39192) Alu subfamily SC sequence contamination warning entry, partial (6%) [THC2281591] | |
| ABTB2 | ankyrin repeat and BTB (POZ) domain containing 2 | NM_145804 |
| ACTC1 | actin, alpha, cardiac muscle 1 | NM_005159 |
| ACY3 | aspartoacylase (aminocyclase) 3 | NM_080658 |
| AKR1C1 | aldo-keto reductase family 1, member C1 (dihydrodiol dehydrogenase 1; 20-alpha (3-alpha)-hydroxysteroid dehydrogenase) | NM_001353 |
| ANKRD47 | ankyrin repeat domain 47 | NM_198471 |
| ANKRD55 | ankyrin repeat domain 55 | NM_024669 |
| ANXA1 | annexin A1 | NM_000700 |
| ARHGAP25 | Rho GTPase activating protein 25 | NM_001007231 |
| BCHE | butyrylcholinesterase | NM_000055 |
| BIRC3 | baculoviral IAP repeat-containing 3 | NM_001165 |
| BLK | B lymphoid tyrosine kinase | NM_001715 |
| BMF | Bcl2 modifying factor | NM_001003940 |
| BTG2 | BTG family, member 2 | NM_006763 |
| C10orf10 | chromosome 10 open reading frame 10 | NM_007021 |
| C10orf33 | chromosome 10 open reading frame 33 | NM_032709 |
| C14orf112 | chromosome 14 open reading frame 112 | NM_016468 |
| C19orf51 | chromosome 19 open reading frame 51 | NM_178837 |
| C1orf38 | chromosome 1 open reading frame 38 | NM_004848 |
| C3orf39 | chromosome 3 open reading frame 39 | NM_032806 |
| C4orf32 | chromosome 4 open reading frame 32 | NM_152400 |
| C6orf192 | chromosome 6 open reading frame 192 | NM_052831 |
| CARD10 | caspase recruitment domain family, member 10 | NM_014550 |
| CARD11 | caspase recruitment domain family, member 11 | NM_032415 |
| CARD14 | caspase recruitment domain family, member 14 | NM_024110 |
| CASP1 | caspase 1, apoptosis-related cysteine peptidase (interleukin 1, beta, convertase) | NM_033292 |
| CCDC104 | coiled-coil domain containing 104 | NM_080667 |
| CCL1 | chemokine (C-C motif) ligand 1 | NM_002981 |
| CCL3L3 | chemokine (C-C motif) ligand 3-like 3 | NM_001001437 |
| CCNA1 | cyclin A1 | NM_003914 |
| CCNG2 | cyclin G2 | NM_004354 |
| CCR4 | chemokine (C-C motif) receptor 4 | NM_005508 |
| CCRL2 | chemokine (C-C motif) receptor-like 2 | NM_003965 |
| CD2 | CD2 molecule | NM_001767 |
| CD274 | CD274 molecule | NM_014143 |
| CD300A | CD300a molecule | NM_007261 |
| CD52 | CD52 molecule | NM_001803 |
| CD68 | CD68 molecule | NM_001251 |
| CD74 | CD74 molecule, major histocompatibility complex, class II invariant chain | NM_004355 |
| CD82 | CD82 molecule | NM_002231 |
| CD83 | CD83 molecule | NM_004233 |
| CDC42EP4 | CDC42 effector protein (Rho GTPase binding) 4 | NM_012121 |
| CEP135 | centrosomal protein 135 kDa | NM_025009 |

-continued

| Gene Symbol | Description | GenBank No. |
|---|---|---|
| CFHR1 | complement factor H-related 1 | NM_002113 |
| CFTR | cystic fibrosis transmembrane conductance regulator (ATP-binding cassette sub-family C, member 7) | NM_000492 |
| CLCF1 | cardiotrophin-like cytokine factor 1 | NM_013246 |
| CLIC4 | chloride intracellular channel 4 | NM_013943 |
| CPNE5 | copine V | NM_020939 |
| CRTAM | cytotoxic and regulatory T cell molecule | NM_019604 |
| CSAG1 | chondrosarcoma associated gene 1 | NM_153479 |
| CSAG2 | CSAG family, member 2 | NM_004909 |
| CSAG3A | CSAG family, member 3A | NM_203311 |
| CXCR7 | chemokine (C-X-C motif) receptor 7 | NM_020311 |
| CXorf9 | chromosome X open reading frame 9 | NM_018990 |
| CXXC5 | CXXC finger 5 | NM_016463 |
| CYFIP1 | cytoplasmic FMR1 interacting protein 1 | NM_014608 |
| CYP1B1 | cytochrome P450, family 1, subfamily B, polypeptide 1 | NM_000104 |
| DHDH | dihydrodiol dehydrogenase (dimeric) | NM_014475 |
| DHRS2 | dehydrogenase/reductase (SDR family) member 2 | NM_182908 |
| DISP2 | dispatched homolog 2 (*Drosophila*) | NM_033510 |
| DNMT3A | DNA (cytosine-5-)-methyltransferase 3 alpha | NM_175630 |
| DPP4 | dipeptidyl-peptidase 4 (CD26, adenosine deaminase complexing protein 2) | NM_001935 |
| DUSP2 | dual specificity phosphatase 2 | NM_004418 |
| EGR2 | early growth response 2 (Krox-20 homolog, *Drosophila*) | NM_000399 |
| ELL2 | elongation factor, RNA polymerase II, 2 | NM_012081 |
| EMID1 | EMI domain containing 1 | NM_133455 |
| EPS8L1 | EPS8-like 1 | NM_133180 |
| ERO1LB | ERO1-like beta (*S. cerevisiae*) | NM_019891 |
| F2RL3 | coagulation factor II (thrombin) receptor-like 3 | NM_003950 |
| FNDC3B | fibronectin type III domain containing 3B | NM_022763 |
| FOSB | FBJ murine osteosarcoma viral oncogene homolog B | NM_006732 |
| GADD45B | growth arrest and DNA-damage-inducible, beta | NM_015675 |
| GCA | grancalcin, EF-hand calcium binding protein | NM_012198 |
| GDPD5 | glycerophosphodiester phosphodiesterase domain containing 5 | NM_030792 |
| GIMAP2 | GTPase, IMAP family member 2 | NM_015660 |
| GPR171 | G protein-coupled receptor 171 | NM_013308 |
| GPR30 | G protein-coupled receptor 30 | NM_001505 |
| GPR56 | G protein-coupled receptor 56 | NM_201525 |
| GRB10 | growth factor receptor-bound protein 10 | NM_001001555 |
| GRTP1 | growth hormone regulated TBC protein 1 | NM_024719 |
| HAVCR2 | hepatitis A virus cellular receptor 2 | NM_032782 |
| HIVEP3 | human immunodeficiency virus type I enhancer binding protein 3 | NM_024503 |
| HLA-DMA | major histocompatibility complex, class II, DM alpha | NM_006120 |
| HLA-DOA | major histocompatibility complex, class II, DO alpha | NM_002119 |
| HLA-DQA2 | major histocompatibility complex, class II, DQ alpha 2 | NM_020056 |
| HLA-DRB1 | major histocompatibility complex, class II, DR beta 1 | NM_002124 |
| HLA-DRB3 | major histocompatibility complex, class II, DR beta 3 | NM_022555 |
| HLA-DRB5 | major histocompatibility complex, class II, DR beta 5 | NM_002125 |
| ICAM1 | intercellular adhesion molecule 1 (CD54), human rhinovirus receptor | NM_000201 |
| IER5L | immediate early response 5-like | NM_203434 |
| IL13 | interleukin 13 | NM_002188 |
| IL23A | interleukin 23, alpha subunit p19 | NM_016584 |
| IL26 | interleukin 26 | NM_018402 |
| IL3RA | interleukin 3 receptor, alpha (low affinity) | NM_002183 |
| IL4 | interleukin 4 | NM_000589 |
| IL4I1 | interleukin 4 induced 1 | NM_172374 |
| IQCG | IQ motif containing G | NM_032263 |
| IQSEC1 | IQ motif and Sec7 domain 1 | NM_014869 |
| JAG1 | jagged 1 (Alagille syndrome) | NM_000214 |
| JUN | jun oncogene | NM_002228 |
| KCNJ16 | potassium inwardly-rectifying channel, subfamily J, member 16 | NM_170741 |
| KIR2DL2 | killer cell immunoglobulin-like receptor, two domains, long cytoplasmic tail, 2 | NM_014219 |

| Gene Symbol | Description | GenBank No. |
|---|---|---|
| KIR2DL4 | killer cell immunoglobulin-like receptor, two domains, long cytoplasmic tail, 4 | NM_002255 |
| KIR2DS1 | killer cell immunoglobulin-like receptor, two domains, short cytoplasmic tail, 1 | NM_014512 |
| KIR2DS2 | killer cell immunoglobulin-like receptor, two domains, short cytoplasmic tail, 2 | NM_012312 |
| KIR2DS4 | killer cell immunoglobulin-like receptor, two domains, short cytoplasmic tail, 4 | NM_178228 |
| KIR3DL1 | killer cell immunoglobulin-like receptor, three domains, long cytoplasmic tail, 1 | NM_013289 |
| KIR3DL2 | killer cell immunoglobulin-like receptor, three domains, long cytoplasmic tail, 2 | NM_006737 |
| KLRB1 | killer cell lectin-like receptor subfamily B, member 1 | NM_002258 |
| LAMB3 | laminin, beta 3 | NM_001017402 |
| LAT | linker for activation of T cells | NM_014387 |
| LAT2 | linker for activation of T cells family, member 2, transcript variant 1 | NM_032464 |
| LAT2 | linker for activation of T cells family, member 2, transcript variant 2 | NM_032463 |
| LBH | limb bud and heart development homolog (mouse) | NM_030915 |
| LPHN3 | latrophilin 3 | NM_015236 |
| LTA | lymphotoxin alpha (TNF superfamily, member 1) | NM_000595 |
| LTBP1 | latent transforming growth factor beta binding protein 1 | NM_206943 |
| LY6D | lymphocyte antigen 6 complex, locus D | NM_003695 |
| LZTS1 | leucine zipper, putative tumor suppressor 1 | NM_021020 |
| MAGEA9 | melanoma antigen family A, 9 | NM_005365 |
| MAGEB2 | melanoma antigen family B, 2 | NM_002364 |
| MEOX1 | mesenchyme homeobox 1 | NM_004527 |
| MICALCL | MICAL C-terminal like | NM_032867 |
| MLLT3 | myeloid/lymphoid or mixed-lineage leukemia (trithorax homolog, *Drosophila*); translocated to, 3 | NM_004529 |
| MPO | myeloperoxidase | NM_000250 |
| MRPS12 | mitochondrial ribosomal protein S12 | NM_021107 |
| NAPSA | napsin A aspartic peptidase | NM_004851 |
| NCOA7 | nuclear receptor coactivator 7 | NM_181782 |
| NCR1 | natural cytotoxicity triggering receptor 1 | NM_004829 |
| NCR3 | natural cytotoxicity triggering receptor 3 | NM_147130 |
| NFIX | nuclear factor I/X (CCAAT-binding transcription factor) | NM_002501 |
| NFKBIA | nuclear factor of kappa light polypeptide gene enhancer in B-cells inhibitor, alpha | NM_020529 |
| NMU | neuromedin U | NM_006681 |
| NPHP1 | nephronophthisis 1 (juvenile) | NM_000272 |
| OASL | 2'-5'-oligoadenylate synthetase-like | NM_003733 |
| OSBPL5 | oxysterol binding protein-like 5 | NM_020896 |
| PASD1 | PAS domain containing 1 | NM_173493 |
| PCDH15 | protocadherin 15 | XM_373461 |
| PIF1 | PIF1 5'-to-3' DNA helicase homolog (*S. cerevisiae*) | NM_025049 |
| PLAU | plasminogen activator, urokinase | NM_002658 |
| PLCG2 | phospholipase C, gamma 2 (phosphatidylinositol-specific) | NM_002661 |
| PPFIBP1 | PTPRF interacting protein, binding protein 1 (liprin beta 1) | NM_003622 |
| PPP1R3F | protein phosphatase 1, regulatory (inhibitor) subunit 3F | NM_033215 |
| PPP2R2B | protein phosphatase 2 (formerly 2A), regulatory subunit B, beta isoform | NM_004576 |
| PRF1 | perforin 1 (pore forming protein) | NM_005041 |
| PRKCDBP | protein kinase C, delta binding protein | NM_145040 |
| PSD3 | pleckstrin and Sec7 domain containing 3 | NM_015310 |
| PTPRC | protein tyrosine phosphatase, receptor type, C | NM_002838 |
| PVRIG | poliovirus receptor related immunoglobulin domain containing | NM_024070 |
| RAGE | renal tumor antigen | NM_014226 |
| RDM1 | RAD52 motif 1 | NM_145654 |
| REEP2 | receptor accessory protein 2 | NM_016606 |
| REL | v-rel reticuloendotheliosis viral oncogene homolog (avian) | NM_002908 |
| RELB | v-rel reticuloendotheliosis viral oncogene homolog B, nuclear factor of kappa light polypeptide gene enhancer in B-cells 3 (avian) | NM_006509 |
| RGS3 | regulator of G-protein signalling 3 | NM_134427 |
| RHOV | ras homolog gene family, member V | NM_133639 |

-continued

| Gene Symbol | Description | GenBank No. |
|---|---|---|
| RIN1 | Ras and Rab interactor 1 | NM_004292 |
| RNASET2 | ribonuclease T2 | NM_003730 |
| RPA4 | replication protein A4, 34 kDa | NM_013347 |
| S100A16 | S100 calcium binding protein A16 | NM_080388 |
| S100A4 | S100 calcium binding protein A4 | NM_002961 |
| S100P | S100 calcium binding protein P | NM_005980 |
| SAMSN1 | SAM domain, SH3 domain and nuclear localization signals 1 | NM_022136 |
| SDC4 | syndecan 4 | NM_002999 |
| SERPIND1 | serpin peptidase inhibitor, clade D (heparin cofactor), member 1 | NM_000185 |
| SH2D1B | SH2 domain containing 1B | NM_053282 |
| SH3PXD2A | SH3 and PX domains 2A | NM_014631 |
| SIGLECP3 | sialic acid binding Ig-like lectin, pseudogene 3 | NR_002804 |
| SLA | Src-like-adaptor | NM_006748 |
| SLC12A7 | solute carrier family 12 (potassium/chloride transporters), member 7 | NM_006598 |
| SLC2A14 | solute carrier family 2 (facilitated glucose transporter), member 14 | NM_153449 |
| SLC2A3 | solute carrier family 2 (facilitated glucose transporter), member 3 | NM_006931 |
| SLC41A2 | solute carrier family 41, member 2 | NM_032148 |
| SLC43A2 | solute carrier family 43, member 2 | NM_152346 |
| SLC45A3 | solute carrier family 45, member 3 | NM_033102 |
| SPG7 | spastic paraplegia 7 (pure and complicated autosomal recessive) | NM_003119 |
| STAT5A | signal transducer and activator of transcription 5A | NM_003152 |
| STMN3 | stathmin-like 3 | NM_015894 |
| STMN4 | stathmin-like 4 | NM_030795 |
| TBX2 | T-box 2 | NM_005994 |
| TBXAS1 | thromboxane A synthase 1 (platelet, cytochrome P450, family 5, subfamily A) | NM_030984 |
| TEF | thyrotrophic embryonic factor | NM_003216 |
| TMEM121 | transmembrane protein 121 | NM_025268 |
| TMEM88 | transmembrane protein 88 | NM_203411 |
| TMTC2 | transmembrane and tetratricopeptide repeat containing 2 | NM_152588 |
| TNF | tumor necrosis factor (TNF superfamily, member 2) | NM_000594 |
| TNFRSF9 | tumor necrosis factor receptor superfamily, member 9 | NM_001561 |
| TNFSF4 | tumor necrosis factor (ligand) superfamily, member 4 (tax-transcriptionally activated glycoprotein 1, 34 kDa) | NM_003326 |
| TNNI3 | troponin I type 3 (cardiac) | NM_000363 |
| TRAα | T cell receptor alpha locus | |
| TRAF1 | TNF receptor-associated factor 1 | NM_005658 |
| TRIB1 | tribbles homolog 1 (Drosophila) | NM_025195 |
| TSPAN18 | tetraspanin 18 | NM_130783 |
| TSPAN32 | tetraspanin 32 | NM_139022 |
| TSPAN33 | tetraspanin 33 | NM_178562 |
| VGLL3 | vestigial like 3 (Drosophila) | NM_016206 |
| VNN2 | vanin 2 | NM_004665 |
| VSIG9 | V-set and immunoglobulin domain containing 9 | NM_173799 |
| ZBTB10 | zinc finger and BTB domain containing 10 | NM_023929 |
| ZDHHC11 | zinc finger, DHHC-type containing 11 | NM_024786 |
| ZNF425 | zinc finger protein 425 | NM_001001661 |

In some embodiments, the hematopoietic disorder-associated molecule in ATLL is CD54, CD82, CD83, CD123, CD252, or CD194.

In some embodiments, a hematopoietic disorder-associated molecule is a protein, peptide or RNA (e.g., mRNA, miRNA, lncRNA) that is expressed in quantitatively and/or qualitatively altered manner by the hematopoietic cell and/or the cells with which the hematopoietic cell interacts and/or communicates compared to how it is expressed in a control cell (e.g., a healthy the hematopoietic cell)

In some embodiments, for example in the therapeutic context, a hematopoietic disorder-associated molecule is a target or a likely target ("druggable target") for binding an agent that reduces or inhibits the pathophysiological effects of the target. In some embodiments, binding of the agent to the target modifies the function of the target, providing a therapeutic benefit to the subject (e.g., patient).

In some embodiments, for example in the diagnostic context, a hematopoietic disorder-associated molecule is a marker/biomarker of disease. In some embodiments, the marker/biomarker is an indicator of a biological processes, pathologic processes, or pharmacologic response. The marker/biomarker may measure cell, tissue, or organ function or another indicator(s) of health.

Hematopoietic disorders encompassed by this disclosure include but are not limited to: leukemias, lymphomas, immune deficiency disorders, autoimmune disorders, inflammatory disorders, polycythemia vera, multiple myeloma, aplastic anemia, thrombocytopenia, and ischemic reperfusion injury.

Leukemias include but are not limited to: Hairy-cell leukemia (HCL) acute lymphocytic leukemia (ALL), acute myelogenous leukemia (AML), chronic lymphocytic leukemia (CLL), chronic myelogenous leukemia (CML), adult T-cell leukemia/lymphoma (ATLL), T-cell or B-cell prolymphocytic leukemia (PLL), T-cell or B-cell large granular lymphocytic leukemia (LGLL), aggressive natural killer cell leukemia.

Lymphomas include but are not limited to: Hodgkin lymphoma or a non-Hodgkin lymphoma such as an immunodeficiency-associated lymphoproliferative disorder, primary central nervous system lymphoma, a precursor lymphoid neoplasm such as B-lymphoblastic leukemia/lymphoma not otherwise specified, B-lymphoblastic leukemia/lymphoma with recurrent genetic abnormalities, T-lymphoblastic leukemia/lymphoma, mature T cell and natural killer cell neoplasms such as extranodal natural killer/T-cell lymphoma-nasal type, enteropathy-associated T-cell lymphoma, hepatosplenic T-cell lymphoma, blastic natural killer cell lymphoma, mycosis fungoides/Sezary syndrome, primary cutaneous anaplastic large cell lymphoma, lymphomatoid papulosis, peripheral T-cell lymphoma not otherwise specified, angioimmunoblastic T-cell lymphoma, anaplastic large cell lymphoma, lymphoplasmacytic lymphoma such as Waldenström macroglobulinemia, splenic marginal zone lymphoma, plasmacytoma, monoclonal immunoglobulin deposition diseases, heavy chain diseases, extranodal marginal zone B-cell lymphoma (MALT lymphoma), nodal marginal zone B-cell lymphoma, follicular lymphoma, primary cutaneous follicle center lymphoma, mantle cell lymphoma, diffuse large-B-cell lymphoma (DLBCL)-not otherwise specified, DLBCL associated with chronic inflammation, Epstein-Barr virus positive DLBCL of the elderly, lymphomatoid granulomatosis, primary mediastinal (thymic) large B-cell lymphoma, intravascular large B-cell lymphoma, ALK+ large B-cell lymphoma, plasmablastic lymphoma, primary effusion lymphoma, large B-cell lymphoma arising in HHV8-associated multicentric Castleman's disease, Burkitt lymphoma/leukemia.

Immune deficiency disorders include but are not limited to: Wiskott-Aldrich syndrome, acquired immunodeficiency syndrome (AIDS), Ataxia-Telangiectasia, Chronic Granulomatous Disease, Chronic Mucocutaneous Candidiasis, Common Variable Immunodeficiency, DiGeorge Syndrome, Hyperimmunoglobulinemia E Syndrome, Selective Immunoglobulin Deficiency, Selective Antibody Deficiency With Normal Immunoglobulins, Severe Combined Immunodeficiency, Spleen Disorders and Immunodeficiency, Transient Hypogammaglobulinemia of Infancy, X-Linked Agammaglobulinemia, immune deficiency induced by radiation, chemotherapy, viral infection or drugs such as immunosuppressants and anticonvulsants.

Autoimmune disorders include but are not limited to: Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Chronic Lyme disease, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis *nodosa*, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (now termed Granulomatosis with Polyangiitis (GPA).

Inflammatory disorders include but are not limited to: atherosclerosis, obesity, periodontitis, Alzheimer's disease, chronic obstructive pulmonary disease (COPD), irritable/inflammatory bowel disease, transplant rejection, appendicitis, bursitis, colitis, cystitis, dermatitis, phlebitis, rhinitis, tendonitis, hypersensitivities, pelvic inflammatory disease, tonsillitis, acne vulgaris, asthma, autoinflammatory diseases, chronic prostatitis, complex regional pain syndrome (CRPS) reflex sympathetic dystrophy (RSD).

Aspects of the disclosure relate to a method of treating a hematopoietic disorder. In some embodiments, the method comprises administering to a subject (e.g., a subject having a hematopoietic disorder) an effective amount of an agent that targets a hematopoietic disorder-associated molecule identified according to the methods described herein.

As used herein, "treat" or "treatment" of hematopoietic disorder includes, but is not limited to, preventing, reducing, halting the development of the hematopoietic disorder, reducing or eliminating the symptoms of a hematopoietic disorder, and/or promoting or inducing regression of the hematopoietic disorder. Any of the hematopoietic disorders described herein is contemplated.

An effective amount of an agent is an amount that is sufficient to provide a medically desirable result, such as treatment of hematopoietic disorder. The effective amount will vary with the particular disorder being treated, the age and physical condition of the subject being treated, the severity of the condition, the duration of the treatment, the nature of any concurrent therapy, the specific route of administration and the like factors within the knowledge and expertise of the health practitioner. For administration to a subject a dosage of from about 0.001, 0.01, 0.1, or 1 mg/kg up to 50, 100, 150, or 500 mg/kg or more can typically be employed.

In some embodiments, the agent is a small molecule, an antisense oligonucleotide, a small interfering RNA (siRNA), a microRNA (miRNA), a genomic DNA editing methodology such as CRISPR, or an antibody. Methods of making such agents are known in the art. The antibody may be a full-length antibody or an antigen-binding fragment thereof, such as a Fab, F(ab)2, Fv, single chain antibody, Fab or sFab fragment, F(ab')2, Fd fragments, scFv, or dAb fragments. Methods for producing antibodies and antigen-binding fragments thereof are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, N.Y. (1989), WO2006/040153, WO2006/122786, and WO2003/002609). The small molecule may be, in some embodiments, an organic compound having a molecular weight of below 900, below 800, below 700, below 600, or below 500 daltons. Methods of making such small molecules are known in the art. Antisense oligonucleotides may be modified or unmodified single-stranded DNA molecules of less than 50 nucleotides in length (e.g., 13-25 nucleotides in length). siRNAs may be double-stranded RNA molecules of about 19-25 base pairs in length with optional 3' dinucleotide overhangs on each strand. Antisense oligonucleotides and siRNAs are generally made by chemical synthesis methods that are known in the art. MicroRNAs (miRNAs) may be transcribed and then processed from a primary-microRNA (pri-miRNA) to a progenitor-microRNA (pro-miRNA) to a pre-microRNA (pre-miRNA), and finally to a mature miRNA. miRNAs may be produced in a subject by delivering a gene that encodes the pri-miRNA, which is then processed in the subject to a mature miRNA. The genomic DNA editing methodologies may be, in some embodiments, be based on zinc finger nucleases or, in other embodiments, be based on Cas9, the RNA-guided endonuclease derived from the type II CRISPR-Cas bacterial adaptive immune system.

The agent and compositions thereof can be formulated for a variety of modes of administration, including systemic, topical or localized administration. A variety of administration routes are available. The particular mode selected will depend upon the type of hematopoietic disorder being treated and the dosage required for therapeutic efficacy. The methods of the disclosure, generally speaking, may be practiced using any mode of administration that is medically acceptable, meaning any mode that produces effective levels of the active compounds without causing clinically unacceptable adverse effects. Such modes of administration include, but are not limited to, oral, rectal, topical, nasal, intradermal, or parenteral routes. The term "parenteral" includes subcutaneous, intravenous, intramuscular, or infusion. The pharmaceutical compositions described herein are also suitably administered by intratumoral, peritumoral, intralesional or perilesional routes, to exert local as well as systemic effects.

Techniques and formulations generally can be found in Remington: The Science and Practice of Pharmacy, Pharmaceutical Press; 22nd edition and other similar references. When administered, an agent or inhibitor as described herein may be applied in pharmaceutically-acceptable amounts and in pharmaceutically-acceptable compositions. Pharmaceutical compositions and pharmaceutically-acceptable carriers are also described herein. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the disclosure. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Some aspects of the disclosure involve methods for diagnosing a hematopoietic disorder in a subject. The method comprises obtaining a cell from a subject having, suspected of having, or at increased risk of having hematopoietic disorder and determining the presence one or more of the hematopoietic disorder-associated molecule (inside a cell, on the surface of a cell, or secreted by the cell) identified according to the methods described herein, wherein the presence of the hematopoietic disorder-associated molecule indicates that the subject has or is at risk of having hematopoietic disorder.

In some embodiments the cell from the subject is in a sample derived from the subject (e.g., a patient). Non-limiting examples of the sample include blood, serum, urine, tissue, and cerebrospinal fluid. In some embodiments, multiple samples of the subject are collected over a period of time. A "period of time" is intended to include a period of days, weeks, months or even years. Multiple samples of the subject may be obtained over a period of time, i.e., a sample is obtained periodically over time at various intervals. A sample can be obtained at any interval. For example, a sample can be taken every day for weeks, months or years. Alternatively, a sample can be obtained once a week, or six times a week for a period of weeks, months or years. In one embodiment, a sample is obtained once a week over a period of three months. In one embodiment, a sample is obtained once a month for a period of months, or years.

Obtaining a sample of a subject means taking possession of a sample of the subject. Obtaining a sample from a subject means removing a sample from the subject. Therefore, the person obtaining a sample of a subject and determining a level of the hematopoietic disorder-associated molecule in the sample does not necessarily obtain the biological sample from the subject. In some embodiments, the sample may be removed from the subject by a medical practitioner (e.g., a doctor, nurse, or a clinical laboratory practitioner), and then provided to the person determining a level of the hematopoietic disorder-associated molecule. The sample may be provided to the person determining a level of the hematopoietic disorder-associated molecule by the subject or by a medical practitioner (e.g., a doctor, nurse, or a clinical laboratory practitioner). In some embodiments, the person determining a level of the hematopoietic disorder-associated molecule obtains a biological sample from the subject by removing the sample from the subject.

It is to be understood that sample may be processed in any appropriate manner to facilitate measuring a level of the hematopoietic disorder-associated molecule. For example, biochemical, mechanical and/or thermal processing methods may be appropriately used to isolate the molecule of interest from a biological sample. The level of the hematopoietic disorder-associated molecule may also be determined in a sample directly.

As used herein, determining the presence of the hematopoietic disorder-associated molecule refers to determining the amount or concentration of the hematopoietic disorder-associated molecule in the sample. "Determining" may refer to ascertaining, calculating, computing, measuring, perceiving and/or a combination thereof the level of the hematopoietic disorder-associated molecule. In some embodiments, determining refers to performing an assay to measure the level of the hematopoietic disorder-associated molecule. In some embodiments, "determining" includes, for example, determining the expression level or activity level of the hematopoietic disorder-associated molecule in the sample. In some embodiments, the expression level of the mRNA encoded by the hematopoietic disorder-associated molecule gene (or a cDNA reverse transcribed therefrom) is determined. In some embodiments, the expression level of the protein encoded is determined.

The level of the hematopoietic disorder-associated molecule may be measured by performing an assay. "Performing an assay" means testing a sample to quantify a level of the hematopoietic disorder-associated molecule described herein. Examples of assays used include, but are not limited to, mass spectroscopy, gas chromatography (GC-MS), HPLC liquid chromatography (LC-MS), immunoassays, Northern blots, Western blots, Reverse phase protein arrays (RPPA), microarrays for the detection of RNA, flow cytometry, and Reverse transcription polymerase chain reaction (RT-PCR). Other appropriate methods for determining a level of biomarkers will be apparent to the skilled artisan.

Mass Spectrometry

The level of the hematopoietic disorder-associated molecule may be determined using Mass Spectrometry such as MALDI/TOF (time-of-flight), SELDI/TOF, liquid chromatography-mass spectrometry (LC-MS), iTRAQ LC/LC/MS/MS, gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). see, e.g., U.S. Publication Nos. 20030199001, 20030134304, and 20030077616.

Mass spectrometry methods are well known in the art and have been used to quantify and/or identify proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4th ed. Vol. 15 (John Wiley & Sons, New York 1995), pp. 1071-1094.

Detection of the presence of the hematopoietic disorder-associated molecule will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Any person skilled in the art understands, any of the components of a mass spectrometer (e.g., desorption source, mass analyzer, detect, etc.) and varied sample preparations can be combined with other suitable components or preparations described herein, or to those known in the art.

Immunoassays

"Radioimmunoassay" is a technique for detecting and measuring the concentration of an antigen using a labeled (e.g., radioactively labeled) form of the antigen. Examples of radioactive labels for antigens include $^{3}H$, $^{14}C$, and $^{125}I$. The concentration of one or more hematopoietic disorder-associated molecule in a sample is measured by having the antigen in the biological sample compete with the labeled (e.g., radioactively) antigen for binding to an antibody to the antigen.

The most common enzyme immunoassay is the "Enzyme-Linked Immunosorbent Assay (ELISA)." ELISA is a technique for detecting and measuring the concentration of an antigen using a labeled (e.g., enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem. 22:895-904.

In a "sandwich ELISA", an antibody (e.g., antibody to a hematopoietic disorder-associated molecule) is linked to a solid phase (i.e., a microtiter plate) and exposed to a biological sample containing antigen (e.g., hematopoietic disorder-associated molecule). The solid phase is then washed to remove unbound antigen. A labeled antibody (e.g., enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and β-galactosidase. The enzyme linked antibody reacts with a substrate to generate a colored reaction product that can be measured.

In a "competitive ELISA", antibody (e.g., antibody to a hematopoietic disorder-associated molecule) is incubated with a sample containing antigen (i.e., hematopoietic disorder-associated molecule). The antigen-antibody mixture is then contacted with a solid phase (e.g., a microtiter plate) that is coated with antigen (i.e., MUC3, PGA3, and/or β2M). The more antigen present in the sample, the less free antibody that will be available to bind to the solid phase. A labeled (e.g., enzyme linked) secondary antibody is then added to the solid phase to determine the amount of primary antibody bound to the solid phase.

In a "immunohistochemistry assay" a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or β-galactosidase), or chemical methods (e.g., DAB/Substrate chromagen).

Other techniques may be used to detect the hematopoietic disorder-associated molecule, according to a practitioner's preference, and based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Detectably labeled antibodies that preferentially bind the hematopoietic disorder-associated molecule described herein. Levels can be quantitated, for example by densitometry.

RNA Detection Techniques

Detection of RNA transcripts may be achieved by Northern blotting, for example, wherein a preparation of RNA is run on a denaturing agarose gel, and transferred to a suitable support, such as activated cellulose, nitrocellulose or glass or nylon membranes. Radiolabeled cDNA or RNA is then hybridized to the preparation, washed and analyzed by autoradiography.

Detection of RNA transcripts can further be accomplished using known amplification methods. For example, it is within the scope of the present disclosure to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994).

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; and target mediated amplification, as described by PCT Publication WO 9322461.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with haematoxylin to demonstrate the histological composition of the sample, and dark field imaging with a suitable light filter shows the developed emulsion. Non-radioactive labels such as digoxigenin may also be used.

In some embodiments, the methods disclosed herein are performed in combination with other methods known in the art for diagnosing a hematopoietic disorder.

In some embodiments, a report summarizing the results of the analysis, i.e. the diagnosis of the subject, and any other information pertaining to the analysis could optionally be generated as part of the analysis (which may be interchangeably referred to herein as "providing" a report, "producing" a report, or "generating" a report). Examples of reports may include, but are not limited to, reports in paper (such as computer-generated printouts of test results) or equivalent formats and reports stored on computer readable medium (such as a CD, computer hard drive, or computer network server, etc.). Reports, particularly those stored on computer readable medium, can be part of a database (such as a database of patient records, which may be a "secure database" that has security features that limit access to the report, such as to allow only the patient and the patient's medical practitioners to view the report, for example). In addition to, or as an alternative to, generating a tangible report, reports can also be displayed on a computer screen (or the display of another electronic device or instrument). A report can further be transmitted, communicated or reported (these terms may be used herein interchangeably), such as to the individual who was tested, a medical practitioner (e.g., a doctor, nurse, clinical laboratory practitioner, genetic counselor, etc.), a healthcare organization, a clinical laboratory, and/or any other party intended to view or possess the report. The act of 'transmitting' or 'communicating' a report can be by any means known in the art, based on the form of the report, and includes both oral and non-oral transmission. Furthermore, "transmitting" or "communicating" a report can include delivering a report ("pushing") and/or retrieving ("pulling") a report. For example, non-oral reports can be transmitted/communicated by such means as being physically transferred between parties (such as for reports in paper format), such as by being physically delivered from one party to another, or by being transmitted electronically or in signal form (e.g., via e-mail or over the internet, by facsimile, and/or by any wired or wireless communication methods known in the art), such as by being retrieved from a database stored on a computer network server, etc.

The present disclosure is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1

CD38 in Hairy Cell Leukemia is a Marker of Poor Prognosis and a New Target for Therapy Hairy cell leukemia (HCL) is characterized by underexpression of the intracellular signaling molecule RhoH.

Reconstitution of RhoH expression limits HCL pathogenesis in a mouse model indicating this could represent a new therapeutic strategy. However, while RhoH reconstitution is theoretically possible as a therapy, it is technically immensely challenging as RhoH protein that is appropriately functional needs to be specifically targeted. Because of this problem, identification of druggable proteins on the HCL surface that were dependent upon RhoH under-expression was undertaken. One such protein was identified as CD38. Analysis of 51 HCL patients demonstrated that 18 were CD38-positive. Interrogation of the clinical record of 23 relapsed HCL patients demonstrated those that were CD38-positive had a mean time to salvage therapy 71 months shorter than patients who were CD38-negative. Knockout of the CD38 gene in HCL cells increased apoptosis, inhibited adherence to endothelial monolayers, and compromised ability to produce tumors in vivo. Furthermore, an anti-CD38 antibody proved effective against pre-existing HCL tumors. Taken together, the data indicate that CD38 expression in HCL drives poor prognosis by promoting survival and heterotypic adhesion. The data also indicate that CD38-positive HCL patients might benefit from treatments based on CD38 targeting.

Hairy-cell leukemia (HCL) is an indolent lymphoproliferative disease characterized by pancytopenia, hepatomegaly, splenomegaly, leukocytosis and neoplastic mononuclear cells in the peripheral blood, bone marrow, liver and spleen (1). Complete remission rates approaching 95% can be achieved by front-line treatment with the purine nucleoside analogues pentostatin or cladribine and second-line treatments that include rituximab or vemurafenib (2, 3). However, despite these impressive statistics, a significant proportion of HCL patients either fail to respond to therapy or develop resistant disease (3). In addition, approximately 48% of patients relapse within 15 years and as time progresses the incidence of relapse increases (4). Since HCL usually presents in late middle-age, countries with aging populations can expect an increasing need for new treatments.

One of the diagnostic markers of HCL is abnormal expression of the gene encoding CD11c (5). Normally, this gene is transcribed only in cells of the myeloid lineage (6). However, in HCL it is also transcribed in the neoplastic lymphocytes. This aberrant transcription is driven by constitutive binding of the proto-oncogene JunD to the CD11c gene promoter (7). Tracking back along a cascade of molecular events, we demonstrated that this activation of JunD is caused by constitutive signaling through the intracellular Ras pathway (7).

Signaling by members of the Ras super-family has been shown to be inhibited by high quantitative levels of RhoH (8). It was found that HCL is characterized by chronic under-expression of RhoH (9). Consequently, the low level of RhoH found in HCL likely allows members of Ras family to be active and drive disease pathogenesis. In vitro reconstitution of RhoH expression inhibits the aberrant expression of CD11c as well as the adhesion and trans-endothelial migration that are hallmarks of HCL (9). In a xenograft mouse model, RhoH reconstitution severely limits HCL pathogenesis and protects against mortality (9).

Pre-clinical studies indicate that RhoH reconstitution could be a new therapy for HCL. However, the transition of this therapy from the laboratory bench to the hospital bedside is technically extremely difficult. First, it requires a recombinant protein to be introduced inside hairy cells. Second, it requires this protein to be specifically targeted only to hairy cells. Third, it requires the protein to be functionally and appropriately active when inside the cells. Because of these challenges, a protein was sought that was dependent upon RhoH under-expression but produced on the cell surface and so easily targeted.

In order to identify a cell-surface protein dependent upon RhoH under-expression, differential microarray analysis was utilized to compare the transcriptome of HCL reconstituted with RhoH with the transcriptome of non-reconstituted HCL. This analysis indicated that the mRNA encoding the cell-surface protein CD38 was dependent upon RhoH under-expression. Subsequently, this dependence was confirmed at the protein level. These findings led to a hypothesis that CD38 could be involved in the pathogenesis of HCL and its targeting might be therapeutic. In order to test this hypothesis, functional analyses on HCL where the CD38 gene had been knocked out were performed. These studies indicated that CD38 promotes HCL survival, heterotypic adhesion, and the growth of xenografts in mice. That CD38 contributes to HCL pathogenesis was further demonstrated by the finding that CD38-positive patients relapsed dramatically sooner than patients who were CD38-negative. Analysis of 51 HCL patients by flow cytometry or immunohistochemistry demonstrated 18 were CD38-positive. Testing of the humanized anti-CD38 antibody SAR650984 in a mouse model indicated that this approximate one-third of HCL patients could benefit from the development of anti-CD38 treatments.

Results

CD38 Expression in HCL is Dependent Upon Low-Level RhoH

Figure 1A:
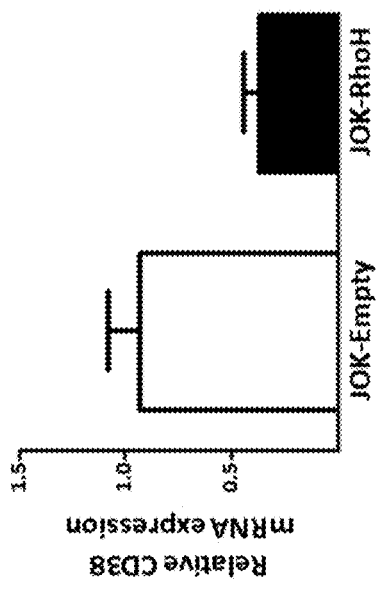
Figure 1C:
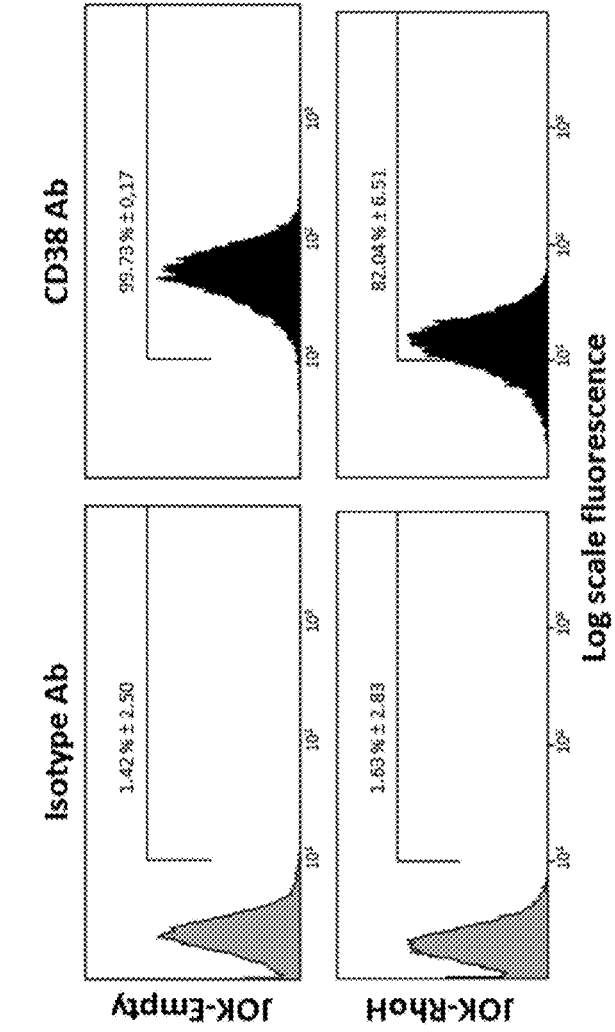

In previous studies, it was determined that HCL is characterized by under-expression of the intracellular signaling molecule RhoH (9). This low-level expression likely contributes to the pathogenesis of the disease by unleashing Ras signaling that ultimately results in aberrant transcription of the CD11c gene and consequent extravasation of the neoplastic lymphocytes (7, 9). Reconstitution of RhoH expression ameliorated HCL pathogenesis in a xenograft mouse model (9). However, transition of this therapeutic approach to the clinic is not likely to be immanent as targeting the reconstitution of an intracellular protein is immensely challenging. Therefore, a readily druggable surface protein that was dependent upon RhoH under-expression was sought. This was achieved using the cell lines JOK-Empty and JOK-RhoH (9). These lines are derived from the HCL cell-line JOK-1 and stably express either the parental vector pMEP4 or this same vector encoding RhoH. Comparison of the transcriptomes of these two derivatives by differential microarray analysis demonstrated that the mRNA encoding the surface protein CD38 was expressed in JOK-RhoH at 0.145 the level it was expressed in JOK-Empty (p=0.003). Repression of CD38 mRNA expression by RhoH reconstitution was confirmed by RT-PCR analysis (FIG. 1A). Repression of CD38 protein expression was demonstrated by western blotting (FIG. 1B). Finally, flow cytometry demonstrated that RhoH reconstitution repressed the surface expression of CD38 (FIG. 1C).

CD38 is Differentially Expressed Both by HCL Cell Lines and HCL Patients

Figure 2A:
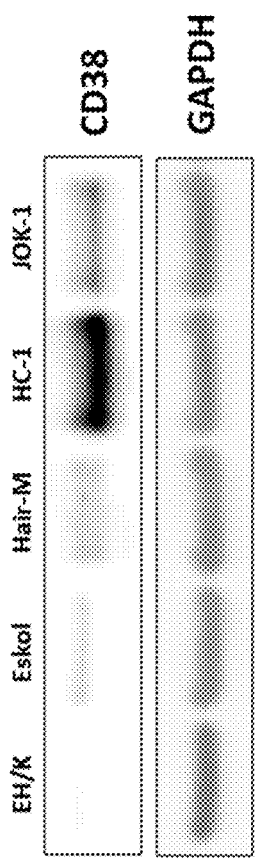
FIGS. 2A-2B show CD38 is differentially expressed by HCL cell lines and patients.
Figure 2B:
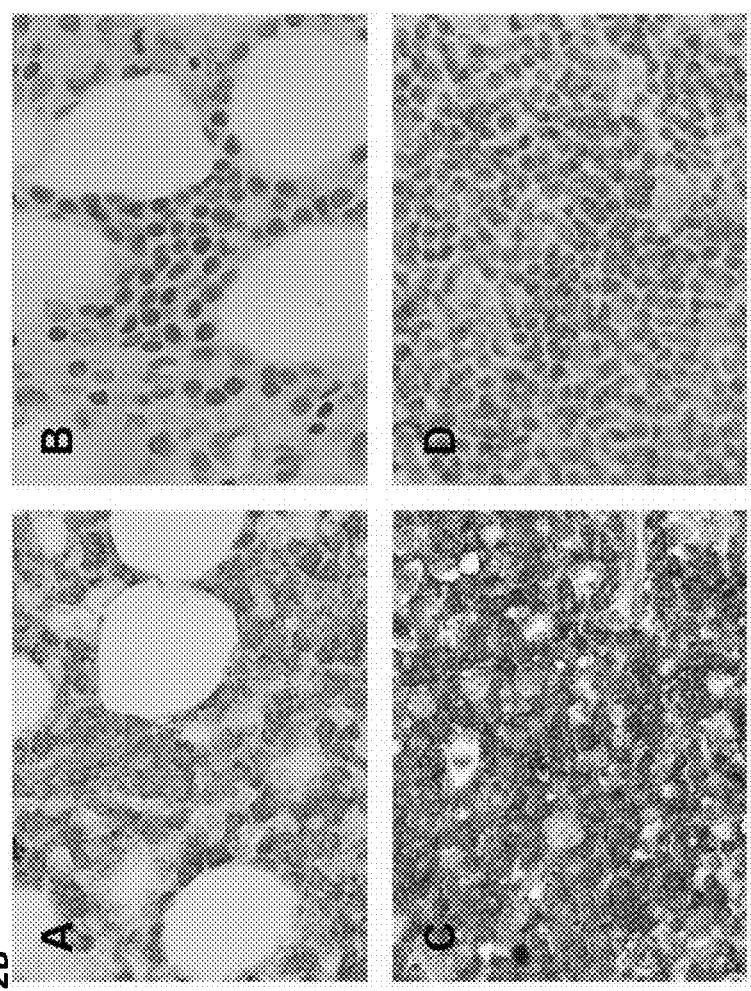

The expression of CD38 in HCL beyond JOK-1 was assessed initially by examining a range of different cell lines by western blotting (FIG. 2A). Such analysis demonstrated that while the HCL cell lines JOK-1, HC-1, Hair-M and Eskol are CD38-positive, the HCL line EH/K is negative. This finding of differential expression of CD38 in HCL was confirmed by analysis of HCL patients. Two of eight HCL patients diagnosed at Gundersen Health Center in the USA exhibited CD38 expression in bone marrow biopsies (FIG.

2B). In addition, examination of the clinical records of 43 HCL patients diagnosed at the Centre Hospitalier Universitaire de Caen in France revealed 16 were CD38-positive in the bone marrow and/or peripheral blood. Taken together, the results from the USA and France indicate that the neoplastic lymphocytes of approximately one third of HCL patients exhibit CD38 expression. This proportion is consistent with what has been reported for HCL patients in Sweden (15).

CD38 Expression is a Marker of Poor HCL Prognosis

Figure 3B:
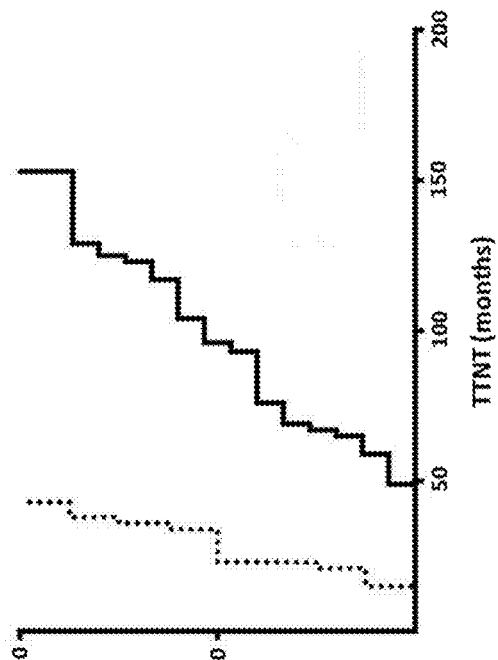
FIGS. 3A-3B show that CD38 is a marker of poor prognosis.
Figure 3A:
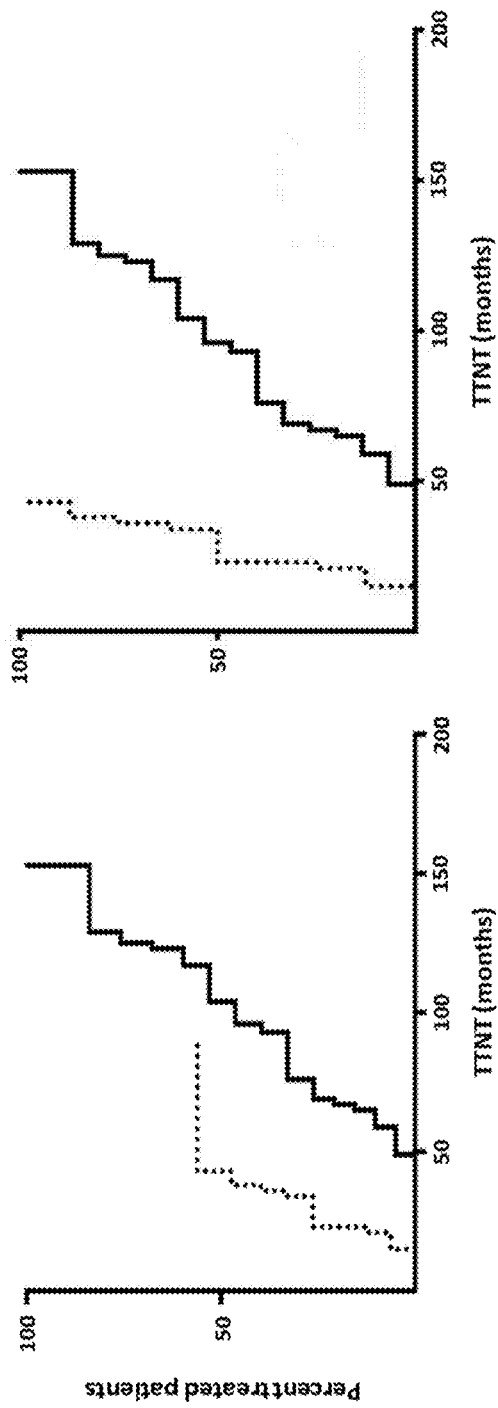

The impact of CD38 expression on clinical course was evaluated by retrospective analysis of the clinical records of the 43 patients diagnosed with classical HCL at the Centre Hospitalier Universitaire de Caen. Specifically, the time between the end of first-line therapy and the beginning of salvage therapy at first relapse was investigated. This interval was designated as the time to next treatment (TTNT). In the 43 cases, it was found that for the 27 patients who were CD38-negative, TTNT was 83 months, but for the 16 patients who were CD38-positive, TTNT was only 42 months (FIG. 3A). When the 23 of the 43 patients that relapsed were analyzed specifically, the difference in TTNT between CD38-negative and CD38-positive cases was even more dramatic. Here, TTNT of the 15 patients who were CD38-negative was 95 months, but only 24 months for the 8 patients who were CD38-positive (FIG. 3B).

CD38 Expression Promotes HCL Growth by Protecting Against Apoptosis

Figure 8:
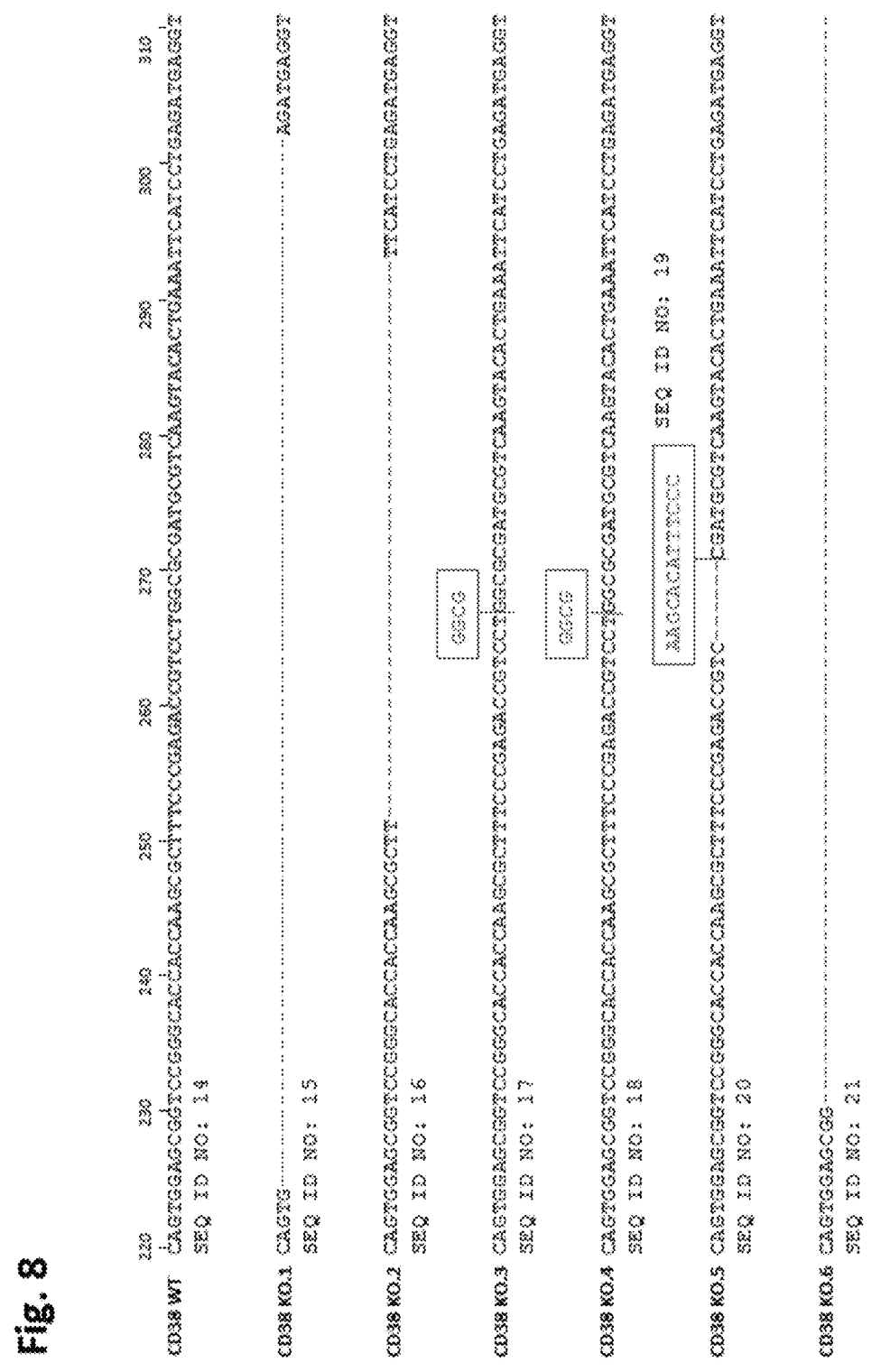

Clinical evidence indicates that CD38 expression in HCL correlates with poor prognosis. Next, whether CD38 expression represents a driver or a passenger in HCL pathogenesis was investigated. This was addressed by utilizing the HCL cell line JOK-1 that is CD38-positive (FIGS. 1B, 2A). Zinc Finger Nuclease technology produced pools of this line that either contained homozygous frame-shift mutations within the CD38 coding region or contained no mutations within this same region (FIG. 8). These pools were designated JOK-CD38-KO and JOK-CD38-WT, respectively. Comparison of the two pools demonstrated that, eight days after the initiation of cultures with equal numbers of cells, the number of JOK-CD38-KO cells was 36% fewer than JOK-CD38-WT (FIG. 4A). The rate at which cells grow in culture represents the sum of the balance between cell division and cell death. Therefore, which of these processes accounted for the difference in growth rate of JOK-CD38-KO and JOK-CD38-WT was investigated. Incorporation of 5-ethynyl-2'-deoxyuridine demonstrated that in cultures of JOK-CD38-KO the percentage of cells in the DNA synthesis phase of the cell cycle was not significantly different than that in cultures of JOK-CD38-WT (FIG. 4B). Consequently, CD38 expression appears not to influence HCL proliferation in vitro. However, in contrast, when apoptosis was assessed by cell-surface binding of annexin V and DNA accessibility to propidium iodide, the intrinsic apoptosis rate of JOK-CD38-KO after 72 hours of culture was found to be approximately one third higher than JOK-CD38-WT (FIG. 4C). Therefore, CD38 expression appears to enhance HCL growth not by effecting an increase in proliferation but rather by increasing cell survival.

CD38 Expression Promotes HCL Adhesion

Figure 5:
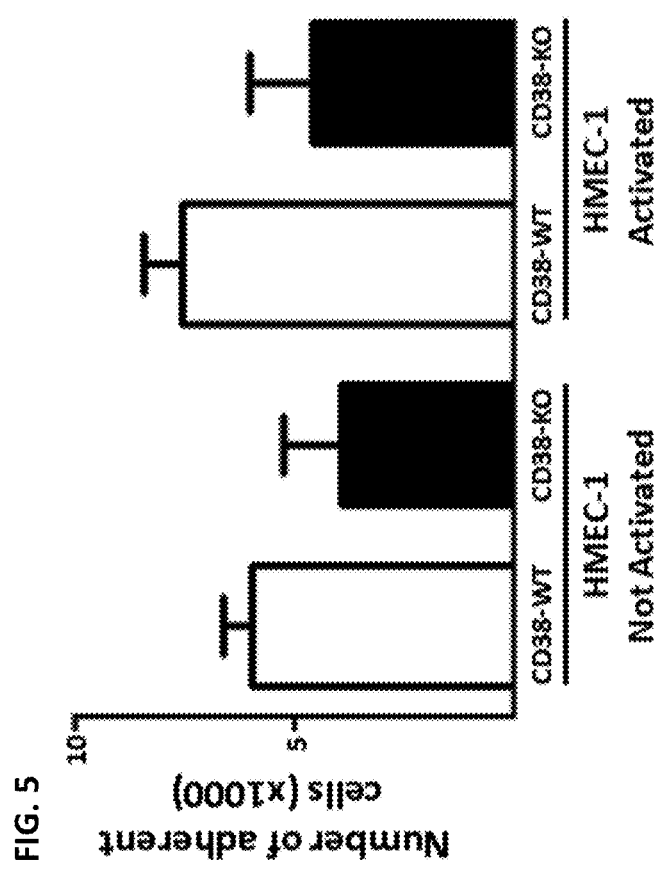
FIG. 5 shows CD38 promotes HCL adhesion. Confluent monolayers of human microvascular cells (HMEC-1) were prepared and either left not activated or activated with LPS. These monolayers were then incubated with JOK-CD38-WT (CD38-WT) or JOK-CD38-KO (CD38-KO) that had previously been labeled with the fluorescent marker BCECF-AM. After 1 hour non-adherent cells were washed off and the fluorescence intensity of monolayers measured. The fluorescence of monolayers that had not been incubated with cells was subtracted from this value to give a measure of the fluorescence acquired by monolayers specifically from the adherence of HCL cells. These specific fluorescence measures were then plotted on standard curves constructed from serial dilutions of a known number of the corresponding HCL cell line labeled with BCECF-AM. In this way, the number of adherent cells was calculated. Histograms represent the mean±s.d. of four experiments performed at minimum in triplicate. The adherence of JOK-CD38-KO to both not activated and activated endothelial cells was significantly lower than the adherence of JOK-CD38-WT (Paired Student t-test: P=0.0332 and 0.0126 respectively).

The adhesion of T cells and CLL B-lymphocytes to endothelial cells has previously been shown to be mediated by CD38 (16, 17). Therefore, the possibility that CD38 also contributes to the adhesive properties of HCL B-lymphocytes was investigated. Confluent monolayers of human microvascular endothelial cells were prepared and either activated with LPS or left untreated. The ability of JOK-CD38-KO and JOK-CD38-WT to adhere to these monolayers was then assessed (FIG. 5). This analysis demonstrated that JOK-CD38-KO was 34% less able to bind non-activated endothelial cells than JOK-CD38-WT and 39% less able to bind activated endothelial cells.

CD38 Effects Growth of HCL Tumors In Vivo

Figure 6:
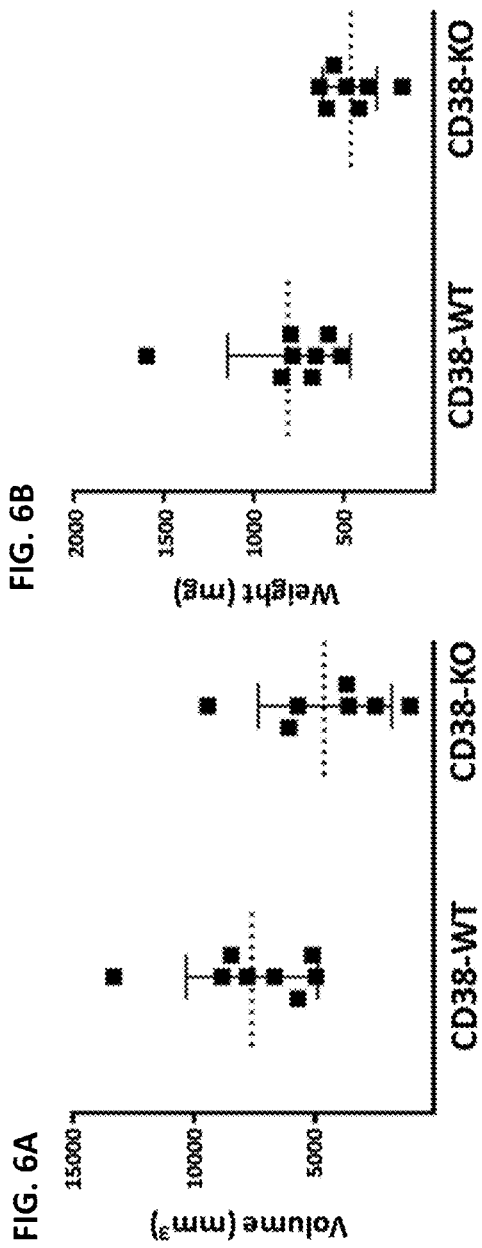
FIGS. 6A-6B show that CD38 promotes HCL growth in vivo.

Analyses performed in vitro indicate that CD38 drives HCL survival and adhesion (FIGS. 4C, 5). These results suggest CD38 expression may contribute to the pathogenesis of HCL in vivo. Therefore, to address this question, JOK-CD38-WT and JOK-CD38-KO were injected subcutaneously into immunodeficient mice. After 4 weeks, the resulting tumors were dissected, weighed, and their dimensions measured. This analysis demonstrated that the tumors originating from JOK-CD38-KO had volumes that were on average 40% smaller than those originating from JOK-CD38-WT (FIG. 6A). In addition, tumor weight was reduced on average by 43% (FIG. 6B). Therefore, these results support the hypothesis that CD38 influences HCL pathogenesis in vivo.

Targeting CD38 Regresses Pre-Existing HCL Tumors In Vivo

Figure 7:
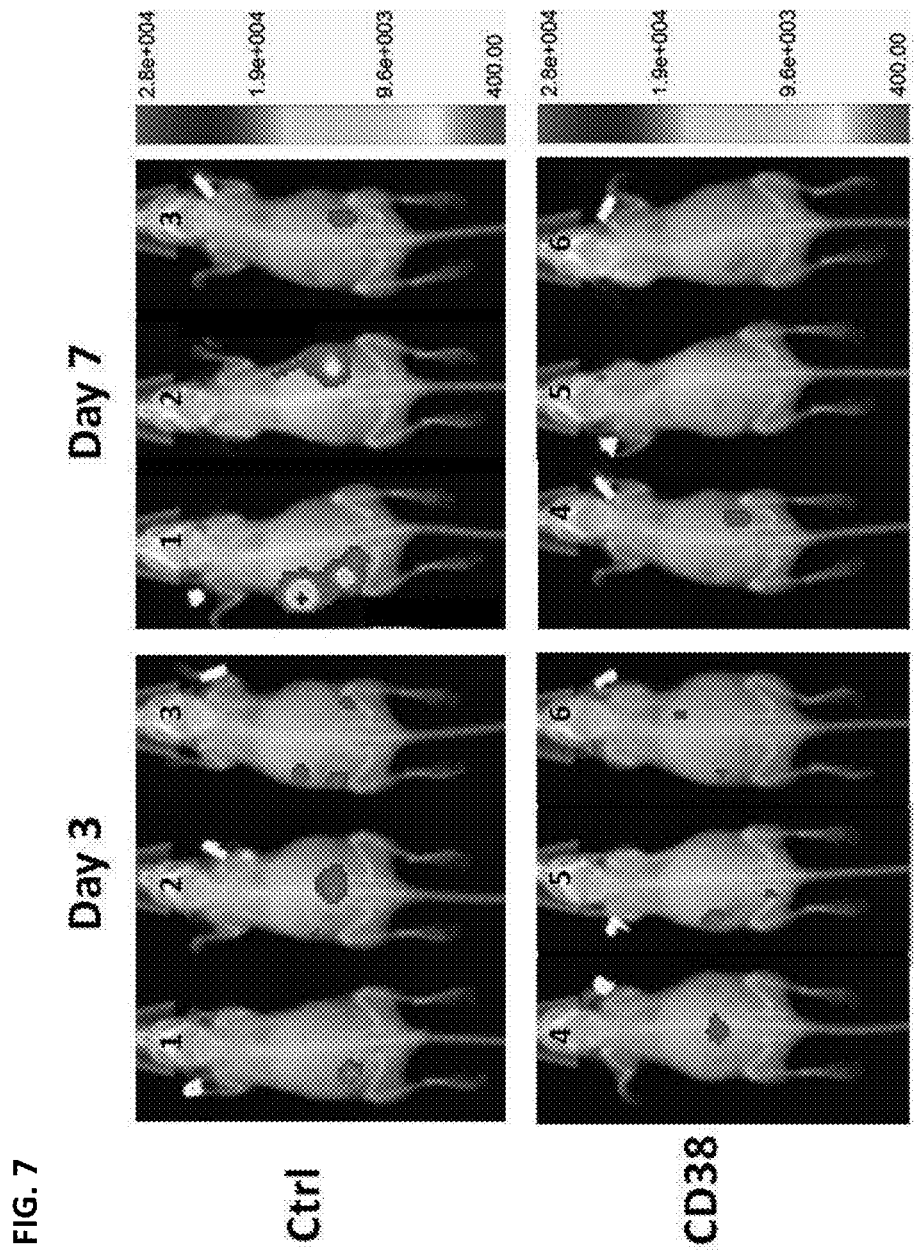
FIG. 7 shows targeting CD38 treats pre-existing HCL in vivo. JOK-1 cells were stably transfected with the plasmid pGL4.5[Luc2/CMV/Neo] that contains the firefly luciferase gene under control of the constitutive gene promoter of cytomegalovirus. This luciferase cell line was then injected into the peritoneum of mice of the strain Hsd:Athymic Nude-Foxn1$^{nu}$. After 3 days, mice were subjected to whole body imaging following intravenous injection of D-Luciferin. Those mice where tumor was detected were intraperitoneally injected at day 4 and day 6 with the anti-CD38 antibody SAR650984 or an IgG control antibody. At day 7, mice were again imaged. Depicted are superimposed luminescence and X-ray images of three mice injected with SAR650984 (CD38) and three injected with the control antibody (Ctrl).

Experiments performed with JOK-CD38-KO indicate that targeting CD38 expression in HCL may have therapeutic efficacy. This was tested using the parent of JOK-CD38-KO where CD38 expression remained intact. The parental line was engineered such that it constitutively produced luciferase and, therefore, could be visualized by luminescence in the presence of luciferin. This line was then injected into the peritoneum of immunodeficient mice and allowed to form tumors. These tumors were then treated with either a non-immune control antibody or the anti-CD38 antibody SAR650984 (18). Luminescence imaging demonstrated that tumors tended to continue to grow after treatment with the control antibody but tended to be reduced by treatment with SAR650984 (FIG. 7).

DISCUSSION

HCL is an indolent neoplasm predominantly of cells with a genetic signature related to memory B-lymphocytes (1, 19). A stubborn percentage of HCL cases are either resistant to available treatments or relapse with intractable disease (3, 4). HCL usually presents in late middle age. Therefore, in regions of the world such as North America and Western Europe with baby-boom generations reaching retirement, the absolute number of HCL patients in need of novel treatments is set to increase. Here, for the first time it is reported that targeting CD38 could represent one such novel therapy. Approximately one-third of HCL patients exhibit CD38 expression and that this expression correlates with poor prognosis. Evidence developed in vitro indicates that the molecular basis of this heightened pathogenesis is the ability of CD38 to effect increased lymphocyte survival and an increased ability to bind endothelium.

The natural history of CD38 expression in HCL bears a striking resemblance to that in CLL. Both are indolent neoplasms with phenotypes related to memory B-cells (19-21). Approximately one-third of both HCL and CLL patients are CD38-positive when the cut-off for positivity is set at 30% of the malignant clone (22-24). In both HCL and CLL, CD38 mediates adhesion to endothelial cells (16, 17). In both HCL and CLL, CD38 protects against apoptosis (25, 26). In both HCL and CLL, CD38-positivity is a negative prognostic indicator (22, 24, 27-31).

It is now widely accepted that in CLL there are dynamic shifts of neoplastic cells between the blood stream and lymphoid tissue. In the circulation, CLL cells manifest resistance to apoptosis but are compromised in their ability to proliferate, while in lymphoid tissue, they are susceptible to apoptosis or induced to proliferate (32-35). These findings indicate that the microenvironment of lymphoid tissue is necessary for CLL proliferation but not for apoptosis resistance (36). CD38 has been implicated in mediating both microenvironment-dependent CLL proliferation and microenvironment-independent survival (16, 37, 38). Extrapolating these roles of CD38 from CLL to HCL would provide an explanation for the observation that knockout of the CD38 gene fails to influence cell division in HCL mono-cultures but does compromise survival.

In addition to CLL, CD38 has previously been found to be expressed in a wide range of other hematologic malignancies including B-cell and T-cell acute lymphoblastic leukemia, multiple myeloma, B-cell non-Hodgkin's lymphoma, and acute myeloid leukemia (39-42). Targeting CD38 in xenograft models of these malignancies has been demonstrated to have therapeutic efficacy and trials are currently underway to determine clinical utility (43-50). The results reported here indicate that HCL should be added to the list of blood cancers where anti-CD38 therapy is being evaluated. However, since monotherapy often results in the evolution of resistant disease, combining CD38 targeting with existing HCL treatments such as purine analogues and agents that target CD20 and B-Raf might prove particularly beneficial.

Materials and Methods
Patient Material

Immunohistochemical analysis was performed on formalin-fixed paraffin-embedded bone marrow biopsies collected from patients diagnosed with either classical HCL or chronic lymphocytic leukemia (CLL) at the Gundersen Medical Center, La Crosse, Wis. (10, 11). The prognostic ability of CD38 was determined by examining the clinical records of 43 patients diagnosed with classical HCL at the Centre Hospitalier Universitaire de Caen, Caen, France. Nine of these patients scored 3 points and 34 patients scored 4 points on the Royal Marsden scoring system for HCL (12). Cases where multi-parameter flow cytometry showed that 30% or more of HCL cells exhibited CD38 expression were designated as being CD38-positive. First-line and salvage treatments were initiated when patients had platelet counts under $100 \times 10^9$/L, hemoglobin levels under 10 g/dL or absolute neutrophil count under $1 \times 10^9$/L.

Immunohistochemistry

Formalin-fixed paraffin-embedded blocks containing bone marrow biopsy specimens were serially sectioned at 4 µm and dried overnight on Colorfrost® Plus microscope slides (Thermo Fisher Scientific, Inc., Waltham, Mass.). Next, sample slides were deparaffinized and one slide from each block was stained with Hematoxylin and Eosin Y. The remaining slides were subjected to epitope retrieval using Epitope Retrieval Solution, pH 9 (Dako North America, Inc., Carpinteria, Calif.). Next, the slides were rocked with the Peroxidase Blocking reagent of the EnVision+ System-HRP (DAB) (Dako North America, Inc.) and then with Surfact-Amps® X-100 (Thermo Fisher Scientific, Inc.). One slide from each block was rocked with an IgG non-immune rabbit antibody (Epitomics, Inc., Burlingame, Calif.). One slide from each block was identically incubated with the rabbit monoclonal EPR4106 antibody that recognizes human CD38 (Abcam, Inc., Cambridge, Mass.). Serial rocking incubations were next performed with Labeled Polymer-HRP Anti-Rabbit, Wash Buffer and DAB+ Chromogen (Dako North America, Inc.). Finally, slides were counterstained with Hematoxylin and the tissue protected by glass coverslips mounted with Permount® (Thermo Fisher Scientific, Inc.).

Cell Culture

The hairy-cell line HC-1 was obtained from the Deutsche Sammlung von Mikroorganismen and Zellkulturen GmbH (DSMZ) (Braunschweig, Germany). The hairy-cell line EH was provided by Guy B. Faguet (Veterans Administration Medical Center, Augusta, Ga.). Subsequently the real identity of EH was found to be the hairy cell line HK (13). Therefore, herein the line is referred to as EH/K. The hairy-cell line ESKOL was provided by Edward F. Srour (Indiana University School of Medicine, Indianapolis, Ind.). The hairy-cell lines JOK-1, and Hair-M were provided by Jørn Koch (Aarhus University Hospital, Aarhus, Denmark). Human microvascular endothelial cells (HMEC-1) were provided by Laurent Plawinski (CNRS UMS 3408 Université de Caen, France). The HCL cell lines JOK-Empty and JOK-RhoH were obtained as previously described and grown in RPMI-1640 containing 10% (v/v) heat-inactivated fetal bovine serum (FBS), 100 units/ml penicillin, 100 µg/ml streptomycin and 150 µg/ml hygromycin B (Gibco Life Technologies, Corp., Saint-Aubin, France) (9). All other HCL cell lines were grown in this same medium lacking hygromycin B. HMEC-1 was grown in Medium 131 containing 100 units/ml penicillin, 100 µg/ml streptomycin and Microvascular Growth Supplement (MVGS) (Gibco Life Technologies, Corp.). In addition, surfaces on which HMEC-1 were grown were coated with Attachment Factor (AF) (Gibco Life Technologies, Corp.). Activation of HMEC-1 was achieved using 100 ng/ml lipopolysaccharide (LPS) (Sigma-Aldrich, Corp., Saint-Quentin Fallavier, France).

Generation of Stable Cell Line Pools

The plasmid pGL4.51[Luc2/CMV/Neo] contains the luciferase gene of *Photinus pyralis* under control of the constitutive gene promoter of cytomegalovirus (Promega, Corp., Madison, Wis., USA). This plasmid was linearized with the restriction endonuclease SalI and transfected into the HCL cell line JOK-1. The cell line pool JOK-Luc was subsequently selected by resistance to 1 mg/ml G418 (Sigma-Aldrich, Corp., St. Louis, Mo., USA). Knockout of the CD38 gene was engineered in the HCL cell line JOK-1 using a CompoZR Zinc Finger Nuclease (ZFN) kit (CKOZFND5725, Sigma-Aldrich, Corp.). Parental JOK-1 cells were transfected with each of the two ZFN plasmids in the kit and CD38-negative cells isolated by a BD FACSAria™ I cell sorter (Becton Dickinson, Franklin Lakes, N.J., USA) using a FITC-labeled mouse anti-human CD38 antibody and an isotype-matched non-immune FITC-labeled antibody (clones IB6 and IS6-11E5.11, respectively) (Miltenyi Biotec, Paris, France). CD38-negative cells were isolated as single clones in 96 multi-well culture plates using the auto-cloning module of the cell sorter. In the same way CD38-positive clones were isolated from the bulk of transfected parental JOK-1 cells. Next, the CD38 gene in each isolated clone was sequenced through the ZFN-targeted region (Table 1). The intended target sequences were 5'-CTTTCCCGAGACCGTCCT-3' (SEQ ID NO: 2) and 5'-GATGCGTCAAGTACACTGAA-3' (SEQ ID NO: 3) on the plus strand of the CD38 gene located on chromosome 4. However, on chromosomes 1, 5, 7 and 9 there are sequences that match these intended targets except for 8-9 nucleotides. Therefore, in order to validate that only the CD38 gene was targeted by the ZFN, genomic DNA was extracted from each of the clones comprising the cell line pools JOK-CD38-KO and JOK-CD38-WT. PCR was performed with the listed forward (F) and reverse (R) primer pairs to amplify regions of 300-500 nucleotides spanning each of the potential ZFN targets. The sequence of these regions was then determined. This analysis demonstrated that each of the clones comprising the pool JOK-CD38-WT contained only wild-type genomic sequences. This same analysis demonstrated that each of the clones comprising the pool JOK-CD38-KO contained disruptions of only the CD38 gene and not of any of the other potential ZFN targets.

TABLE 1

Genomic localization of target sequences potentially recognized by the ZFN used to generate the cell line pools JOK-CD38-KO and JOK-CD38-WT (the sequences, from top to bottom, correspond to SEQ ID NOs: 4-13)

| Target Name | Genomic Location | Intended Target Mismatches | PCR primers |
|---|---|---|---|
| On-Target CD38 | 4p15.32 | 0 | F: 5'-CAACTCTGTCTTGGC GTCAG-3'<br>R: 5'-GGACTCCCTACTCAG CACCA-3' |
| Off-Target n°1 | 1q23.3 | 8 | F: 5'-CAAAAGAGTGATGGG GTAGG-3'<br>R: 5'-TATTTATAGGCAAGG TGAGGAC-3' |
| Off-Target n°2 | 5p14.3 | 9 | F: 5'-CTGGGGAAACCTAAG AGATG-3'<br>R: 5'-GGCTCATGGAAGAAA ACTAAG-3' |
| Off-Target n°3 | 7q34 | 9 | F: 5'-TCTGCTGGGAGTAGG ATGC-3'<br>R: 5'-TGCTAACAATGCTGG GTCA-3' |
| Off-Target n°4 | 9p21.1 | 9 | F: 5'-TATGTACTGCCCAGG TCAAG-3'<br>R: 5'-TTTTTCTTTCTCACA CTGCC-3' |

Figure 9:
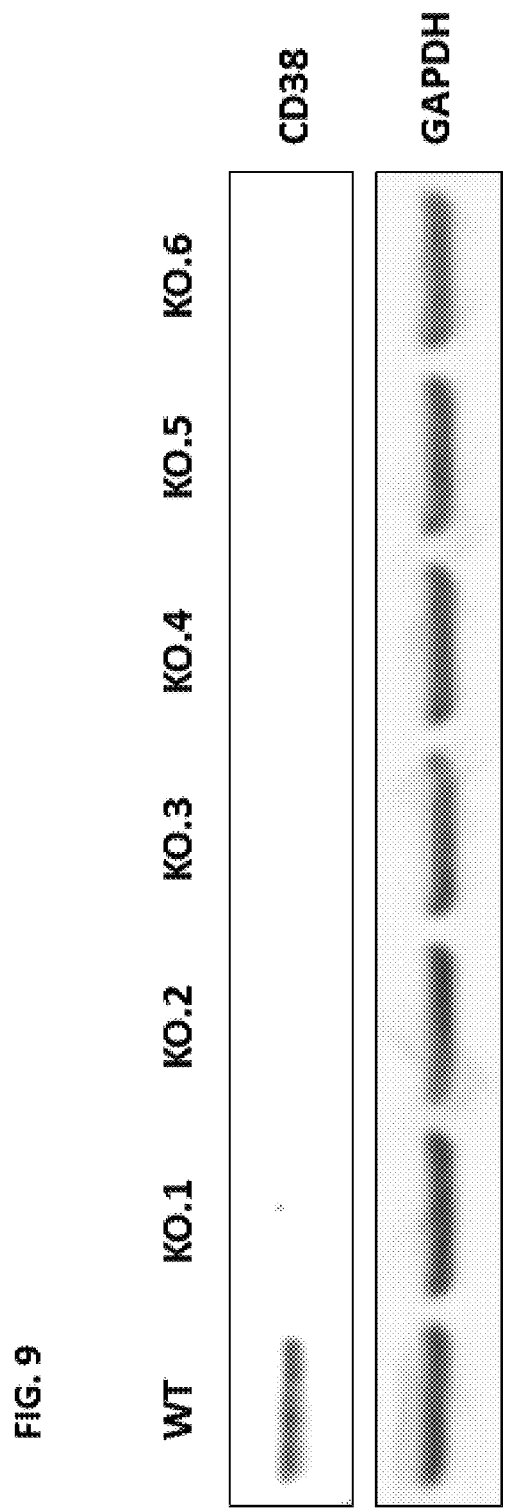
FIG. 9 shows a Western blot analysis of CD38 expression in total protein lysates prepared from the cell line pool JOK-CD38-WT (WT) and from each of the six individual clones that constitute the pool JOK-CD38-KO (KO.1-6). This analysis demonstrates robust expression of CD38 by JOK-CD38-WT, but absence of expression by each of the clones that were mixed to produce JOK-CD38-KO. An antibody against GAPDH was used in the control analysis of lysates.
Figure 10:
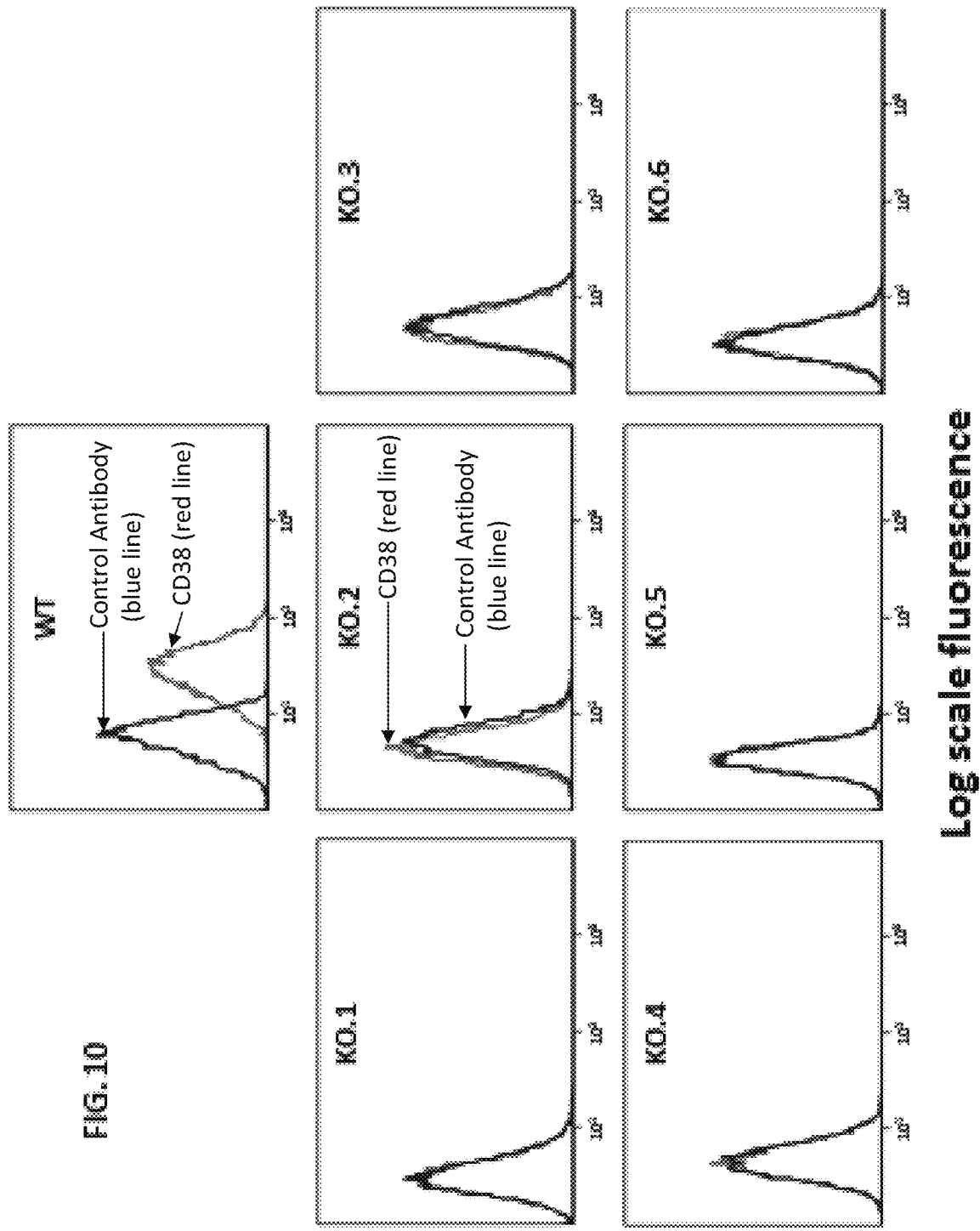
FIG. 10 shows a flow cytometric analysis of CD38 expression on the surface of the cell line pool JOK-CD38-WT (WT) and on each of the six individual clones that constitute the pool JOK-CD38-KO (KO.1-6). Analysis was performed using a FITC-conjugated antibody that specifically binds CD38 (red lines) or an isotype-matched control antibody (blue lines). Depicted are representative examples of flow patterns showing robust expression of CD38 on JOK-CD38-WT but absence of expression on each of the clones that were mixed to produce JOK-CD38-KO.

Six clones were identified that contained homozygous frame-shift mutations within the CD38 coding region (FIG. 8). Six clones were identified that contained no mutations within this same region. All validated clones were first cultured alone and then 106 cells of each were mixed together to produce the cell line pools JOK-CD38-WT and JOK-CD38-KO representing HCL where the CD38 gene is wild-type or mutated, respectively. Expression of CD38 in each of these pools was assessed by western blotting and flow cytometry (FIGS. 9-10).

Microarray Analysis

The transcriptomes of JOK-RhoH and JOK-Empty were compared as previously described using Human Whole Genome Agilent 44K 60-mer oligonucleotide microarrays and an Agilent DNA Microarray G2505B scanner (Agilent Technologies, Les Ulis, France) (14). Expression data was extracted by Feature Extraction Version 9.1.3.1 then analyzed by GeneSpring Version 7.3 (Agilent Technologies).

Quantitative RT-PCR

Total RNA from cell cultures was purified then reverse-transcribed into cDNA using Moloney murine lentivirus reverse transcriptase and random primers (Invitrogen, Life Technologies, Corp.) (9, 14). Next, 100 ng of the generated cDNA was subjected to quantitative PCR using the Taqman Universal Master Mix and the CD38 Gene Expression Assay Hs01120068_m1 containing a CD38-specific TaqMan probe and primers (Applied Biosystems, Life Technologies, Corp.). Linear regression curves constructed from the CD38-positive cell line HC-1 quantified CD38 expression levels which were then normalized against expression of ABL mRNA (9, 14). PCR was performed on an 7900HT Real-Time PCR System using the standard protocol of SDS 2.4 software (Applied Biosystems, Life Technologies, Corp.).

Western Blotting

Proteins were isolated from cell cultures using the M-PER® lysis reagent (Thermo-Fisher Scientific, Perbio Science, Brebières, France). Proteins were then reduced using Sample Reducing Agent (Life Technologies, Corp.), subjected to polyacrylamide gel electrophoresis and transferred to nitrocellulose filters. Next, filters were incubated with primary antibodies directed against human CD38, α-actin or glyceraldehyde 3-phosphate dehydrogenase (GAPDH). Specifically, the anti-CD38 antibody used was mouse monoclonal 22/CD38 (BD Pharmingen, Le Pont-de-Claix, France). Anti-α-actin was mouse monoclonal AC-15 (Sigma-Aldrich, Corp). Anti-GAPDH was rabbit polyclonal FL-335 (Santa Cruz Biotechnology, Inc.). Following incubation with primary antibodies, filters were washed and incubated with appropriate anti-mouse or anti-rabbit secondary antibodies conjugated with horseradish peroxidase (HRP) (Cell Signaling Technology, Inc., Ozyme, Montigny-le-Bretonneux, France). Filters were again washed and HRP visualized using the Amersham ECL Prime® Western Blotting System (GE Healthcare Europe, GmbH, Vélizy-Villacoublay, France).

Flow Cytometry

Flow cytometric analysis of JOK-Empty, JOK-RhoH, JOK-CD38-WT and JOK-CD38-KO was performed by incubating $5\times10^5$ cells with a FITC-conjugated version of the monoclonal antibody IB6 directed against CD38 (Miltenyi Biotec). The isotype-matched control for these experiments utilized a FITC-conjugated version of the IgG2b clone IS6-11E5.11 (Miltenyi Biotec). Following incubation with antibodies, cells were analyzed using a CyAn™ ADP flow cytometer equipped with Summit software 4.3 (Beckman Coulter, Inc., Fullerton, Calif., USA).

Cell-Cycle Assays

The percentage of cells in the S phase of the cell cycle was assessed using the Click-iT® EdU Alexa Fluor® 647 Flow Cytometry Assay Kit (Life Technologies, Corp.). The assay consisted of labeling $5\times10^5$ cells with 10 µM of 5-ethynyl-2'-deoxyuridine (EdU), fixation with Click-iT® fixative then permeabilization with Click-iT® saponin-based reagent. Next, intracellular EdU was conjugated with Alexa Fluor® 647 using the Click-iT® reaction cocktail. The percentage of cells that were positive for EdU-Alexa Fluor® 647 was determined by flow cytometry and taken as representing the proportion of the culture in S phase.

Apoptosis Assays

Cultures of JOK-CD38-WT or JOK-CD38-KO were initiated. After 72 hours, $5\times10^5$ cells were washed in ice-cold phosphate buffered saline (PBS) then incubated with FITC-conjugated Annexin V and propidium iodide (PI) (Beckman Coulter, Inc., Villepinte, France). The percentage of PI-positive cells that were also Annexin V-positive was determined by flow cytometry and taken as the proportion of the cultures that were undergoing apoptosis.

Heterotypic Adhesion Assays

The ability of JOK-CD38-WT or JOK-CD38-KO to adhere to HMEC-1 was assessed as previously described (9). Briefly, monolayers of HMEC-1 were produced in 96 multiwell tissue culture plates and either activated with 100 ng/ml of LPS or left untreated. JOK-CD38-WT or JOK-CD38-KO cultures were incubated with 5 µM BCECF-AM (Life Technologies, Corp.), washed, then $10^5$ of these labeled cells set onto the monolayers. Adhesion was allowed for 1 hour at 37° C., then monolayers were washed and fluorescence intensity measured at 535 nm using a Spectra-Max® i3 Multi-Mode Detection Platform (Molecular Devices, LLC, Sunnyvale, Calif.). All values were corrected by subtraction of the fluorescence intensity of monolayers incubated with wash buffer alone. These corrected values were then plotted against standard curves of fluorescence intensity constructed from serial dilutions of a known number of the corresponding HCL cell line labeled with BCECF-AM.

Mouse Husbandry

Mice utilized for subcutaneous xenografts of HCL were housed in sterilized GM500 ventilated cages on a Green Line® rack (Techniplast France S. A., Lyon). This housing system was kept in a barrier room accredited by the Direction Départementale de la Protection des Populations du Nord. Mice were monitored daily and sterile water and Rat & Souris No 1 Entretien® diet (SDS Special Diet Services France, Argenteuil) was provided ad libitum. Mice utilized for intraperitoneal xenografts of HCL were housed in sterilized Super Mouse 750™ Micro-Isolator™ ventilated cages on a RAIR Isosytem™ rack (Lab Products, Inc., Seaford, Del.). This housing system was kept in a barrier room accredited by AAALAC-I. Mice were monitored daily and sterile water and Teklad Global 18% Protein Rodent Diet™ (Harlan Laboratories, Inc) was provided ad libitum.

Xenograft Mouse Models

The role of CD38 in HCL was assessed using $5\times10^6$ of the cell line pools JOK-CD38-WT or JOK-CD38-KO injected subcutaneously into male or female mice that were 6-8 weeks old and of the strain NOD.Cg-Prkdc$^{scid}$ IL2rγ$^{tm1Wjl}$/SzJ (Jackson Laboratory, Bar Harbor, Me., USA). Four weeks after injection, mice were sacrificed and tumors dissected, weighed and measured with an electronic caliper. Tumor volumes were calculated according to the formula: $(4\times\pi\times L\times W\times T)/3$, where L is length, W is width and T is thickness. The therapeutic efficacy of targeting CD38 was assessed using $4\times10^6$ of the cell line pool JOK-Luc injected into the peritoneum of female mice that were 3-4 weeks old and of the strain Hsd:Athymic Nude-Foxn1$^{nu}$ (Harlan Laboratories, Inc., Indianapolis, Ind.). After 3 days mice were anesthetized and injected intravenously with 150 µl of Dulbecco's phosphate buffered saline containing 15 mg/ml D-Luciferin potassium salt (Regis Technologies, Inc., Morton Grove, Ill.). Superimposed luminescence and X-ray images were acquired using a MS FX PRO In Vivo Imaging System (Bruker Corp., Billerica, Mass.). The day after imaging, mice with visible tumors were injected intraperitoneally with 120 µl of phosphate buffered saline containing 1 mg/ml of either the humanized anti-CD38 antibody SAR650984 (Sanofi Oncology, Cambridge, Mass.) or a non-immune IgG1 kappa antibody purified from human myeloma plasma (Sigma-Aldrich, Corp.). Two days later the antibody injections were repeated and the following day mice were again imaged. Intraperitoneal xenograft protocols were approved by the Institutional Animal Care and Use Committee of the University of Wisconsin, La Crosse, Wis., USA. Subcutaneous xenograft protocols were approved by the Animal Care Ethical Committee, Nord-Pas-de-Calais, France.

SEQUENCES

| SEQ ID NO. | Sequence |
|---|---|
| 1 | MLSSIKCVLVGDSAVGKTSLLVRFTSETFPEAYKPTVYENTGVDV FMDGIQISLGLWDTAGNDAFRSIRPLSYQQADVVLMCYSVANHNS FLNLKNKWIGEIRSNLPCTPVLVVATQTDQREMGPHRASCVNAME GKKLAQDVRAKGYLECSALSNRGVQQVFECAVRTAVNQARRRNRR RLFSINECKIF |
| 2 | CTTTCCCGAGACCGTCCT |
| 3 | GATGCGTCAAGTACACTGAA |
| 4 | CAACTCTGTCTTGGCGTCAG |
| 5 | GGACTCCCTACTCAGCACCA |
| 6 | CAAAAGAGTGATGGGGTAGG |
| 7 | TATTTATAGGCAAGGTGAGGAC |
| 8 | CTGGGGAAACCTAAGAGATG |
| 9 | GGCTCATGGAAGAAAACTAAG |
| 10 | TCTGCTGGGAGTAGGATGC |
| 11 | TGCTAACAATGCTGGGTCA |
| 12 | TATGTACTGCCCAGGTCAAG |
| 13 | TTTTTCTTTCTCACACTGCC |
| 14 | CAGTGAGATGAGGT |
| 15 | CAGTGGAGCGGTCCGGGCACCACCAAGCGCTTTCCCGAGACCGTC CTGGCGCGATGCGTCAAGTACACTGAAATTCATCCTGAGATGAGG T |
| 16 | CAGTGGAGCGGTCCGGGCACCACCAAGCGCTTTTCATCCTGAGAT GAGGT |
| 17 | CAGTGGAGCGGTCCGGGCACCACCAAGCGCTTTCCCGAGACCGTC CTGGCGCGATGCGTCAAGTACACTGAAATTCATCCTGAGATGAGG T |
| 18 | CAGTGGAGCGGTCCGGGCACCACCAAGCGCTTTCCCGAGACCGTC CTGGCGCGATGCGTCAAGTACACTGAAATTCATCCTGAGATGAGG T |
| 19 | AAGCACATTTCCC |
| 20 | CAGTGGAGCGGTCCGGGCACCACCAAGCGCTTTCCCGAGACCGTC CGATGCGTCAAGTACACTGAAATTCATCCTGAGATGAGGT |
| 21 | CAGTGGAGCGG |

REFERENCES

1. Bouroncle B A, Wiseman B K, Doan C A. Leukemic reticuloendotheliosis. *Blood* 1958; 13: 609-630.
2. Robak T. Current treatment options in hairy cell leukemia and hairy cell leukemia variant. *Cancer Treat Rev* 2006; 32: 365-376.
3. Sári E, Nagy Z G, Baghy K, Rajnai H, Bodor C, Csomor J, et al. Treatment of refractory hairy cell leukemia with BRAF-inhibitor: lessons to be learnt. *Pathol Oncol Res* 2014; 20: 973-980.
4. Else M, Dearden C E, Matutes E, Garcia-Talavera J, Rohatiner A Z S, Johnson S A N, et al. Long-term follow-up of 233 patients with hairy cell leukaemia, treated initially with pentostatin or cladribine, at a median of 16 years from diagnosis. *Br J Haematol* 2009; 145: 733-740.
5. Schwarting R, Stein H, Wang C Y. The monoclonal antibodies α S-HCL (α Leu-14) and αS-HCL3 (α Leu-M5) allow the diagnosis of hairy cell leukemia. *Blood* 1985; 65: 974-983.
6. Shelley C S, Böttinger E P, Arnaout M A. Transcriptional regulation of α2 integrins. In: *Leukocyte adhesion: Basic and Clinical Aspects* (Elsevier Science Publishers B.V.) 1992; pp. 337-351.
7. Nicolaou F, Teodoridis J M, Park H, Georgakis A, Farokhzad O C., Bottinger E P, et al. CD11c gene expression in hairy-cell leukemia is dependent upon activation of the proto-oncogenes ras and junD. *Blood* 2003; 101: 4033-4041.
8. Li X, Bu X, Lu B, Avraham H, Flavell R A, Lim B. The hematopoietic-specific GTP-binding protein RhoH is GTPase deficient and modulates activities of other Rho GTPases by an inhibitory function. *Mol Cell Biol* 2002; 22:1158-1171.
9. Galiègue-Zouitina S, Delestré L, Dupont C, Troussard X, Shelley C S. Underexpression of RhoH in hairy cell leukemia. *Cancer Res* 2008; 68: 4531-4540.
10. Fu Q, Cash S E, Andersen J J, Kennedy C R, Oldenburg D G, Zander V B, et al. CD43 in the nucleus and cytoplasm of lung cancer is a potential therapeutic target. *Int J Cancer* 2013; 132: 1761-1770.
11. Fu Q, Cash S E, Andersen J J, Kennedy C R, Madadi A R, Raghavendra M, et al. Intracellular patterns of sialophorin expression define a new molecular classification of breast cancer and represent new targets for therapy. *Br J Cancer* 2014; 110: 146-155.
12. Matutes E, Morilla R, Owusu-Ankomah K, Houliham A, Meeus P, Catovsky D. The immunophenotype of hairy cell leukemia (HCL). Proposal for a scoring system to distinguish HCL from B-cell disorders with hairy or villous lymphocytes. *Leuk Lymphoma* 1994; 14 Suppl 1: 57-61.
13. Drexler H G, Dirks W G, Matsuo Y, MacLeod R A F. False leukemia-lymphoma cell lines: an update on over 500 cell lines. *Leukemia* 2003; 17: 416-426.
14. Delestré L, Berthon C, Quesnel B, Figeac M, Kerckaert J-P, Galiégue-Zouitina S, et al. Repression of the RHOH gene by JunD. *Biochem J* 2011; 437: 75-88.
15. Juliusson G, Lenkei R, Liliemark J. Flow cytometry of blood and bone marrow cells from patients with hairy cell leukemia: phenotype of hairy cells and lymphocyte subsets after treatment with 2-chlorodeoxyadenosine. *Blood* 1994; 83: 3672-3681.
16. Deaglio S, Mallone R, Baj G, Arnulfo A, Surico N, Dianzani U, et al. CD38/CD31, a receptor/ligand system ruling adhesion and signaling in human leukocytes. *Chem Immunol* 2000; 75: 99-120.
17. Patten P E, Buggins A G, Richards J, Wotherspoon A, Salisbury J, Mufti G J, et al. CD38 expression in chronic lymphocytic leukemia is regulated by the tumor microenvironment. *Blood* 2008; 111: 5173-5181.
18. Deckert J, Wetzel M C, Bartle L M, Skaletskaya A, Goldmacher V S, Vallée, F, et al. SAR650984, a novel humanized CD38-targeting antibody, demonstrates potent antitumor activity in models of multiple myeloma and other CD38+ hematologic malignancies. *Clin Cancer Res* 2014; 20: 4574-4583.
19. Basso K, Liso A, Tiacci E, Benedetti R, Pulsoni A, Foa R, et al. Gene expression profiling of hairy cell leukemia reveals a phenotype related to memory B cells with altered expression of chemokine and adhesion receptors. *J Exp Med* 2004; 199: 59-68.
20. Klein U, Tu Y, Stolovitzky G A, Mattioli M, Cattoretti G, Husson H, et al. Gene expression profiling of B cell chronic lymphocytic leukemia reveals a homogeneous phenotype related to memory B cells. *J Exp Med* 2001; 194: 1625-1638.
21. Rosenwald A, Alizadeh A A, Widhopf G, Simon R, Davis R E, Yu X, et al. Relation of gene expression phenotype to immunoglobulin mutation genotype in B cell chronic lymphocytic leukemia. *J Exp Med* 2001; 194: 1639-1648.
22. Damle R N, Wasil T, Fais F, Ghiotto F, Valetto A, Allen S L, et al. Ig V gene mutation status and CD38 expression as novel prognostic indicators in chronic lymphocytic leukemia. *Blood* 1999; 94: 1840-1847.
23. Deaglio S, Vaisitti T, Aydin S, Ferrero E, Malavasi F. In-tandem insight from basic science combined with clinical research: CD38 as both marker and key component of the pathogenetic network underlying chronic lymphocytic leukemia. *Blood* 2006; 108: 1135-1144.
24. Matrai Z. CD38 as a prognostic marker in CLL. *Hematology* 2005; 10: 39-46.
25. Deaglio S, Vaisitti T, Bergui L, Bonello L, Horenstein A L, Tamagnone L, et al. CD38 and CD100 lead a network of surface receptors relaying positive signals for B-CLL growth and survival. *Blood* 2005; 105: 3042-3050.
26. Pepper C, Ward R, Lin T T, Brennan P, Starczynski J, Musson M, et al. Highly purified CD38+ and CD38− sub-clones derived from the same chronic lymphocytic leukemia patient have distinct gene expression signatures despite their monoclonal origin. *Leukemia* 2007; 21: 687-696.
27. Del Poeta G, Maurillo L, Venditti A, Buccisano F, Epiceno A M, Capelli G, et al. Clinical significance of CD38 expression in chronic lymphocytic leukemia. *Blood* 2001; 98: 2633-2639.
28. Ibrahim S, Keating M, Do K A, O'Brien S, Huh Y O, Jilani I, et al. CD38 expression as an important prognostic factor in B-cell chronic lymphocytic leukemia. *Blood* 2001; 98: 181-186.
29. Jelinek D F, Tschumper R C, Geyer S M, Bone N D, Dewald G W, Hanson C A, et al. Analysis of clonal B-cell CD38 and immunoglobulin variable region sequence status in relation to clinical outcome for B-chronic lymphocytic leukaemia. *Br J Haematol* 2001; 115: 854-861.
30. Morabito F, Mangiola M, Oliva B, Stelitano C, Callea V, Deaglio S, et al. Peripheral blood CD38 expression predicts survival in B-cell chronic lymphocytic leukemia. *Leuk Res* 2001; 25: 927-932.
31. Durig J, Naschar M, Schmücker U, Renzing-Köhler K, Holier T, Hüttmann A, et al. CD38 expression is an important prognostic marker in chronic lymphocytic leukaemia. *Leukemia* 2002; 16: 30-35.
32. Burger J A, Ghia P, Rosenwald A, Caligaris-Cappio F. The microenvironment in mature B-cell malignancies: a target for new treatment strategies. *Blood* 2009; 114: 3367-3375.
33. Calissano C, Damle R N, Hayes G, Murphy E J, Hellerstein M K, Moreno C, et al. In vivo intraclonal and interclonal kinetic heterogeneity in B-cell chronic lymphocytic leukemia. *Blood* 2009; 114: 4832-4842.
34. Zenz T, Mertens D, Küppers R, Döhner H, Stilgenbauer S. From pathogenesis to treatment of chronic lymphocytic leukaemia. *Nat Rev Cancer* 2010; 10: 37-50.

35. Damle R N, Calissano C, Chiorazzi N. Chronic lymphocytic leukaemia: a disease of activated monoclonal B cells. *Best Pract Res Clin Haematol* 2010; 23: 33-45.
36. Deaglio S, Malavasi F. Chronic lymphocytic leukemia microenvironment: shifting the balance from apoptosis to proliferation. *Haematologica* 2009; 94: 752-756.
37. Malavasi F, Deaglio S, Damle R, Cutrona G, Ferrarini M, Chiorazzi N. CD38 and chronic lymphocytic leukemia: a decade later. *Blood* 2011; 118: 3470-3478.
38. Deaglio S, Vaisitti T, Zucchetto A, Gattei V, Malavasi F. CD38 as a molecular compass guiding topographical decisions of chronic lymphocytic leukemia cells. *Sem Cancer Biol* 2010; 20: 416-423.
39. Keyhani A, Huh Y O, Jendiroba D, Pagliaro L, Cortez J, Pierce S, et al. Increased CD38 expression is associated with favorable prognosis in adult acute leukemia. *Leuk Res* 2000; 24: 153-159.
40. Konopleva M, Rissling I, Andreeff M. CD38 in hematopoietic malignancies. *Chem Immunol* 2000; 75: 189-206.
41. Leo R, Boeker M, Peest D, Hein R, Bartl R, Gessner J E, et al. Multiparameter analyses of normal and malignant human plasma cells: CD38++, CD56+, CD54+, cIg+ is the common phenotype of myeloma cells. *Ann Hematol* 1992; 64: 132-139.
42. Schuurman H-J, Huppes W, Verdonck L F, van Baarlen J, van Unnik J A M. Immunophenotyping of non-Hodgkin's lymphoma. Correlation with relapse-free survival. *Am J Pathol* 1988; 131: 102-111.
43. Stevenson F K, Bell A J, Cusack R, Hamblin T J, Slade C J, Spellerberg M B, et al. Preliminary studies for an immunotherapeutic approach to the treatment of human myeloma using chimeric anti-CD38 antibody. *Blood* 1991; 77: 1071-1079.
44. Goldmacher V S, Bourret L A, Levine B A, Rasmussen R A, Pourshadi M, Lambert J M, et al. Anti-CD38-blocked ricin: an immunotoxin for the treatment of multiple myeloma. *Blood* 1994; 84: 3017-3025.
45. de Weers M, Tai Y T, van der Veer M S, Bakker J M, Vink T, Jacobs D C, et al. Daratumumab, a novel therapeutic human CD38 monoclonal antibody, induces killing of multiple myeloma and other hematological tumors. *J Immunol* 2011; 186: 1840-1848.
46. Chillemi A, Zaccarello G, Quarona V, Ferracin M, Ghimenti C, Massaia M, et al. Anti-CD38 antibody therapy: windows of opportunity yielded by the functional characteristics of the target molecule. *Mol Med* 2013; 19: 99-108.
47. Ellis J H, Barber K A, Tutt A, Hale C, Lewis A P, Glennie M J, et al. Engineered anti-CD38 monoclonal antibodies for immunotherapy of multiple myeloma. *J Immunol* 1995; 155: 925-937.
48. Mehta K, Ocanas L, Malavasi F, Marks J W, Rosenblum M G. retinoic acid-induced CD38 antigen as a target for immunotoxin-mediated killing of leukemia cells. *Mol Cancer Ther* 2004; 3: 345-352.
49. Flavell D J, Boehm D A, Emery L, Noss A, Ramsay A, Flavell S U. Therapy of human B-cell lymphoma bearing SCID mice is more effective with anti-CD19- and anti-CD38-saporin immunotoxins used in combination than with either immunotoxin used alone. *Int J Cancer* 1995; 62: 337-344.
50. Mihara K, Yanagihara K, Takigahira M, Kitanaka A, Imai C, Bhattacharyya J, et al. Synergistic persistent effect of T-cell immunotherapy with anti-CD19 or anti-CD38 chimeric receptor in conjunction with rituximab on B-cell non-Hodgkin lymphoma. *Br J Heamatol* 2010; 151: 37-46.

EQUIVALENTS

The foregoing written specification is considered to be sufficient to enable one ordinarily skilled in the art to practice the disclosure. The present disclosure is not to be limited in scope by examples provided, since the examples are intended as mere illustrations of one or more aspects of the disclosure. Other functionally equivalent embodiments are considered within the scope of the disclosure. Various modifications of the disclosure in addition to those shown and described herein will become apparent to those skilled in the art from the foregoing description. Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth or illustrated in the drawings. The disclosure is capable of other embodiments and of being practiced or of being carried out in various ways.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

All references, patents and patent applications that are recited in this application are incorporated by reference herein in their entirety.

I claim:

1. A method of identifying a hematopoietic disorder-associated molecule in a hematopoietic cell, the method comprises:
    identifying a hematopoietic cell having abnormal RhoH level,
    restoring RhoH level in the cell to a control level, and
    measuring a level of a molecule in the cell before and after restoring the level of RhoH in the cell to the control level, wherein a decrease in the level of the molecule in the cell after restoring the RhoH level in the cell to the control level indicates that the molecule is a hematopoietic disorder-associated molecule,
    wherein the hematopoietic disorder is an adult T-cell leukemia-lymphoma (ATLL), and the ATLL-associated molecule comprises CD194, CD82, CD83, CLIC4, GPR30, GPR56, GPR171 or TSPAN33.

2. A method of identifying a hematopoietic disorder-associated molecule in a hematopoietic cell, the method comprises:
    identifying a hematopoietic cell having abnormal RhoH level,
    restoring RhoH level in the cell to a control level, and
    measuring a level of a molecule in the cell before and after restoring the level of RhoH in the cell to the control level, wherein a decrease in the level of the molecule in the cell after restoring the RhoH level in the cell to the control level indicates that the molecule is a hematopoietic disorder-associated molecule,
    wherein the hematopoietic disorder is a hairy-cell leukemia (HCL), and the HCL-associated molecule comprises CD21, CD22, CD23, CD121b, CD150, CD307c, CSF1R, FCRL2, FCRL3, GPNMB, GPR30, ITGB7, KCNMA1 or TSPAN33.

* * * * *